United States Patent [19]
Oi et al.

[11] Patent Number: 5,840,917
[45] Date of Patent: Nov. 24, 1998

[54] PHOSPHORYLAMIDES, THEIR PREPARATION AND USE

[75] Inventors: Satoru Oi, Nara; Hideaki Nagaya; Nobuhiro Inatomi, both of Osaka; Masafumi Nakao, Ikoma; Hidefumi Yukimasa, Nara, all of Japan

[73] Assignee: Takeda Chemical Industries, Ltd., Osaka, Japan

[21] Appl. No.: 750,087

[22] PCT Filed: Sep. 25, 1996

[86] PCT No.: PCT/JP96/02769

§ 371 Date: Dec. 6, 1996

§ 102(e) Date: Dec. 6, 1996

[87] PCT Pub. No.: WO97/11705

PCT Pub. Date: Apr. 3, 1997

[30] Foreign Application Priority Data

Sep. 26, 1995 [JP] Japan ................................. 7-247929
Mar. 5, 1996 [JP] Japan ................................. 8-047454

[51] Int. Cl.$^6$ ........................... C07D 333/00; C07F 9/06; A61K 31/38; A61K 31/34

[52] U.S. Cl. ........................... 549/6; 549/218; 549/220; 558/185; 558/199; 558/200; 548/309.4; 548/180; 548/217; 514/448; 514/468; 514/471; 514/120; 514/137; 514/394; 514/367; 514/375

[58] Field of Search ........................ 549/6, 218; 514/448, 514/461, 471, 120, 137, 394, 367, 375; 558/185, 199, 200; 548/309.4, 180, 217

[56] References Cited

U.S. PATENT DOCUMENTS

| | | | |
|---|---|---|---|
| 2,769,013 | 10/1956 | LowenStein-Lom | 549/6 |
| 3,317,637 | 5/1967 | Brust . | |
| 4,182,881 | 1/1980 | Bayless et al. | 546/22 |
| 4,221,730 | 9/1980 | Alaimo et al. | 260/397.7 |
| 4,242,325 | 12/1980 | Bayless et al. | 424/210 |
| 4,454,126 | 6/1984 | Yamatsu et al. | 424/212 |
| 4,517,003 | 5/1985 | Kole et al. | 71/28 |
| 4,522,942 | 6/1985 | Kohsaka et al. | 514/95 |
| 4,528,020 | 7/1985 | Kole et al. | 71/28 |
| 4,584,132 | 4/1986 | Albrecht et al. | 260/239 |
| 4,629,491 | 12/1986 | Swerdloff et al. | 71/87 |
| 4,668,667 | 5/1987 | Moorehead et al. | 514/89 |
| 5,472,956 | 12/1995 | Borch et al. | 514/95 |

FOREIGN PATENT DOCUMENTS 42-7379  3/1967  Japan .

OTHER PUBLICATIONS

Rote Liste, 1991, p. 59048.
A. Colm et al., "Is Urease a Lethal Target for Therapy of *Helicobacter pylori*", Abstracts, Mirco. Ecol. Health Dis. No. 4, (Suppl.), p. S145, 1991.
T. Kühler et al., "Structure–Activity Relationship of Omeprazole and Analogues as *Helicobacter pylori* Urease Inhibitors", J. Med. Chem., No. 38, pp. 4906–4916, 1995.
L. Cates et al., "Phosphorus–Nitrogen Compounds VII. Urethan Derivatives", J. Pharm. Sci., No. 57, pp. 189–199, 1968.
W. Faraci et al., "Inhibition of *Helicobacter pylori* urease by phenyl phosphorodiamidates: mechanism of action", Bioorganic & Medicinal Chemistry, vol. 3, No. 5, pp. 605–610, 1995.
A. McColm et al., "Development of a $^{14}$C–urea breath test ferrets colonised with *Helicobacter mustelae*: effects of treatment with bismuth, antibiotics, and urease inhibitors", Gut, vol. 34, No. 2, pp. 181–186, 1993.
Chemical Abstracts (1982), 97(13): Abstract No. 110198f.

Primary Examiner—Deborah C. Lambkin
Attorney, Agent, or Firm—Wenderoth, Lind & Ponack,LLP

[57] ABSTRACT

A phosphorylamide derivative represented by the general formula (I):

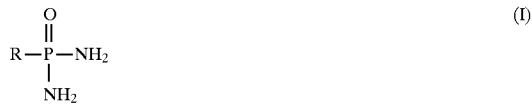

wherein R represents an amino group that may be substituted, or a salt thereof, possesses potent antibacterial activity against Helicobacter bacterium, especially *Helicobacter pylori*, and is useful for prevention or treatment of digestive diseases caused by Helicobacter bacterium, solely or in combination with an antacid or an acid secretion inhibitor.

44 Claims, No Drawings

PHOSPHORYLAMIDES, THEIR PREPARATION AND USE

This application is a 371 of PCT/JP96/02769 filed Sep. 25, 1996, published as WO97/11705 Apr. 3, 1997.

BACKGROUND OF THE INVENTION

1. Field of the Invention

The present invention relates to phosphorylamides, their preparation and use. More specifically this invention relates to a phosphorylamide derivative possessing excellent antibacterial activity based on excellent anti-urease activity, especially potent antibacterial activity against Helicobacter bacteria such as *Helicobacter pylori*, a method for producing the phosphorylamide derivative, and an anti-*Helicobacter pylori* agent which comprises the phosphorylamide derivative and antacid or an acid secretion inhibitor.

2. Background Art

Among the bacteria showing toxic action, *Helicobacter pylori* which is a gram-negative, slightly aerobic bacterium belonging to the genus Helicobacter is considered to be a major cause of recurrent gastritis, duodenal ulcer, gastric ulcer etc.

Helicobacter bacteria, especially *Helicobacter pylori*, possessing potent urease activity, reportedly survive in the stomach, in which they neutralize strong acidity around them by producing ammonia from urea.

Various diseases caused by *Helicobacter pylori* are now treated by double chemotherapy with a bismuth preparation and an antibiotic, or by triple chemotherapy with a bismuth preparation, metronidazole (U.S. Pat. No. 2,944,061) and either tetracycline (e.g., U.S. Pat. No. 2,712,517) or amoxicillin (U.S. Pat. No. 3,192,198). Metronidazole, an imidazole derivative possessing anti-*Helicobacter pylori* activity, is used in combination with an antibiotic. These bismuth preparations, antibiotics, metronidazole etc. are administered orally.

However, these bismuth preparations, antibiotics, metronidazole etc. must be administered at high daily doses to maintain sufficient concentrations to inhibit *Helicobacter pylori* proliferation at the sites of their proliferation, and this produces in many problems, including adverse effects such as vomiting and diarrhea.

On the other hand, some phosphorylamide derivatives are known to possess anti-urease activity (e.g., U.S. Pat. No. 3,317,637, U.S. Pat. No. 4,517,003, U.S. Pat. No. 4,528,020, EP 210703, U.S. Pat. No. 4,182,881, U.S. Pat. No. 4,221,730 Japanese Patent Unexamined Publication No. 99490/1983, Japanese Patent Examined Publication No. 7379/1967, U.S. Pat. No. 4,629,491 and J. Pharm. Sci., 189, 57 (1968)), but there is no disclosure that these phoaphorylamide derivatives exhibit antibacterial action, especially anti-*Helicobacter pylori* action, in vivo.

SUMMARY OF THE INVENTION

The present invention provides a phosphorylamide derivative or a salt thereof possessing excellent antibacterial activity, especially potent antibacterial activity against Helicobacter bacteria such as Helicobacter pylori, and an anti-*Helicobacter pylori* agent comprising the phosphorylamide derivative and antacid or an acid secretion inhibitor.

After extensive investigation in view of the above problem, the present inventors found that a phosphorylamide derivative possessing excellent anti-urease activity exhibits potent antibacterial action in vivo against bacteria (e.g., Helicobacter bacteria such as *Helicobacter pylori*) showing toxic action in the digestive tract. The inventors conducted further research based on this finding, and completed the present invention.

Accordingly, the present invention relates to:

(1) use of a compound represented by the general formula (I):

wherein R represents an amino group which may be substituted, or a pharmaceutically acceptable salt thereof, for the preparation of an anti-*Helicobacter pylori* agent which is used in combination with an antacid or an acid secretion inhibitor;

(2) use of the compound represented by the general formula (I) or a pharmaceutically acceptable salt thereof, for the preparation of an anti-*Helicobacter pylori* agent for prophylaxis of recurrence of ulcer in combination with an antacid or an acid secretion inhibitor;

(3) a combination preparation which contains the compound represented by the general formula (I) or a pharmaceutically acceptable salt thereof, and an antacid or an acid secretion inhibitor;

(4) a compound represented by the general formula (IA):

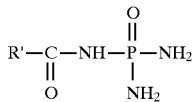

wherein R' represents (a) a heterocyclic group which may be substituted (except a furyl group which may be substituted, a pyridyl group which may be substituted and a 3-amino-2-oxo-1-azetidinyl group which may be substituted), (b) a hydrocarbon group substituted by a heterocyclic group which may be substituted (except a phenyl group substituted by a maleimido group which may be substituted), (c) a hydrocarbon group substituted by a phenoxy group which is substituted, (d) a hydrocarbon group substituted by a heterocyclic-thio group which may be substituted, or (e) an alkyl group substituted by an arylsulfonylamino group which may be substituted, or a salt thereof;

(5) a compound represented by the general formula (IA'):

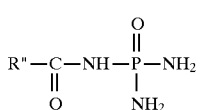

wherein R" represents a furyl group or a pyridyl group, each of which has 1 to 3 substituents selected from the group consisting of halogen, cyano, formyl, lower ($C_{1-3}$) alkyl which may be substituted by halogen, lower ($C_{1-3}$) alkoxy which may be substituted by halogen, (lower ($C_{1-3}$) alkoxy) carbonyl which may be substituted by halogen, or lower ($C_{1-3}$) alkylsulfonyl which may be substituted by halogen, or a salt thereof;

(6) a process for producing the compound of the general formula (IA) or a salt thereof, which comprises reacting a compound of the formula:

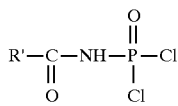

(IIIA)

wherein R' is as defined above, or a salt thereof, with ammonia;

(7) a process for producing the compound of the formula (IA') or a salt thereof,
which comprises reacting a compound of the formula:

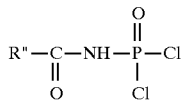

(IIIA')

wherein R" is as defined above, or a salt thereof, with ammonia;

(8) an anti-*Helicobacter pylori* agent which comprises the compound represented by the general formula (I) or a pharmaceutically acceptable salt thereof, and an antacid or an acid secretion inhibitor; and (9) a method for eradicating *Helicobacter pylori* from a mammal, which comprises administering to said mammal the compound represented by the general formula (I)or a pharmaceutically acceptable salt thereof, in combination with an antacid or an acid secretion inhibitor.

With respect to the above general formulas, the substituents in the "amino group that may be substituted," represented by R, are exemplified by (1) acyl groups, (2) carboxyl groups that may be esterified, and (3) hydrocarbon groups that may be substituted. The amino group may be substituted by 1 or 2 of these substituents, whether identical or not. The substituents are preferably an acyl group or a carboxyl group that may be substituted, and more preferably an acyl group.

(1) The acyl group as a substituent in the "amino group that may be substituted," represented by R, is exemplified by acyl groups derived from carboxylic acids, thiocarboxylic acids, sulfonic acids, sulfinic acids, carbamic acids, thiocarbamic acids etc., specifically those represented by the respective general formulas —$COR^1$, —$CSR^2$, —$SO_2R^3$, —$SOR^4$, —$CONHR^5$ or —$CSNHR^6$ ($R^1, R^2, R^3, R^4, R^5$ and $R^6$ independently represent a hydrogen atom, a hydrocarbon group that may be substituted or a heterocyclic group that may be substituted) etc. Preferable acyl groups include those derived from carboxylic acids (—$COR^1$) and those derived from sulfonic acids (—$SO_2R^3$), and those derived from carboxylic acids are more preferable.

The "hydrocarbon group that may be substituted," represented by $R^1, R^2, R^3, R^4, R^5$ or $R^6$, is exemplified by saturated or unsaturated aliphatic chain hydrocarbon groups, saturated or unsaturated alicyclic hydrocarbon groups and aryl groups.

Such saturated aliphatic hydrocarbon groups include linear or branched saturated aliphatic hydrocarbon groups having 1 to 10 carbon atoms (e.g., $C_{1-10}$ alkyl groups such as methyl, ethyl, propyl, isopropyl, butyl, isobutyl, sec-butyl, tert-butyl, pentyl, isopentyl, neopentyl, tert-pentyl, hexyl, isohexyl, heptyl and octyl), and linear or branched saturated aliphatic hydrocarbon groups having 1 to 6 carbon atoms are preferable.

Such unsaturated aliphatic hydrocarbon groups include linear or branched unsaturated aliphatic hydrocarbon groups having 2 to 10 carbon atoms (e.g., $C_{2-10}$ alkenyl groups such as ethenyl, 1-propenyl, 2-propenyl, 1-butenyl, 2-butenyl, 3-butenyl, 2-methyl-l-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl and 1-octenyl; $C_{2-10}$ alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl), and linear or branched unsaturated aliphatic hydrocarbon groups having 2 to 6 carbon atoms are preferable.

Such saturated alicyclic hydrocarbon groups include saturated alicyclic hydrocarbon groups having 3 to 12 carbon atoms (e.g., monocyclic or bicyclic $C_{3-12}$ cycloalkyl groups such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl), and saturated alicyclic hydrocarbon groups having 3 to 6 carbon atoms are preferable.

Such unsaturated alicyclic hydrocarbon groups include unsaturated alicyclic hydrocarbon groups having 5 to 12 carbon atoms (e.g., $C_{5-12}$ cycloalkenyl groups such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2-cyclopenten-1-yl, 3-cyclopenten-1-yl, 2-cyclohexen-1-yl and-3-cyclohexen-1-yl; $C_{5-12}$ cycloalkadienyl groups such as 2,4-cyclopentadien-1-yl, 2,4-cyclohexadien-1-yl and 2,5-cyclohexadien-1-yl and 2,4-cycloheptadienyl).

The hydrocarbon group in the "hydrocarbon group that may be substituted" may be a saturated aliphatic hydrocarbon group having 1 to 8 carbon atoms substituted by the above saturated or unsaturated alicyclic hydrocarbon group (e.g., $C_{3-7}$ cycloalkyl-$C_{1-8}$ alkyl groups and $C_{5-7}$ cycloalkenyl-$C_{1-8}$ alkyl groups, such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl), or the like.

Such aryl groups include monocyclic or fused polycyclic aromatic hydrocarbon ring groups having 6 to 14 carbon atoms. Such aromatic hydrocarbon ring groups include phenyl, 1- or 2-naphthyl, 1-, 2- or 9-anthryl, 1-, 2-, 3-, 4- or 9-phenanthryl, 1-, 2-, 4-, 5- or 6-azulenyl and acenaphthylenyl, and $C_{6-10}$ aryl groups such as phenyl, 1-naphthyl and 2-naphthyl are preferable.

The "hydrocarbon group that may be substituted" may have 1 to 3 optionally chosen substituents at any possible positions. Such substituents include (1) lower alkyl groups that may be substituted, (2) lower alkoxy groups that may be substituted, (3) aryl groups that may be substituted, (4) lower cycloalkyl or cycloalkenyl groups that may be substituted, (5) heterocyclic groups that may be substituted, (6) carboxyl groups that may be esterified, (7) carbamoyl groups that may be substituted, (8) amino groups that may be substituted, (9) hydroxyl groups that may be substituted, (10) thiol (mercapto) groups that may be substituted, (11) acyl groups, (12) halogens (e.g., fluorine, chlorine, bromine), (13) nitro, and (14) cyano.

The lower alkyl group in the lower alkyl group (1) that may be substituted, is exemplified by $C_{1-6}$ alkyl groups such as methyl, ethyl, propyl, isopropyl, butyl, isobutyl, sec-butyl, tert-butyl, pentyl, isopentyl, neopentyl, hexyl and isohexyl.

The lower alkoxy group in the lower alkoxy group (2) that may be substituted, is exemplified by $C_{1-6}$ alkoxy groups such as methoxy, ethoxy, propoxy, isopropoxy, butoxy, isobutoxy, sec-butoxy, tert-butoxy, pentoxy, isopentoxy, neopentoxy, hexyloxy and isohexyloxy.

Said lower alkyl group (1) and lower alkoxy group (2) may have 1 to 3 optionally chosen substituents at any possible positions. Such substituents include halogens (e.g., fluorine, chlorine, bromine) and lower ($C_{1-3}$) alkoxy groups (e.g., methoxy, ethoxy, propoxy).

The aryl group in the aryl group (3) that may be substituted, is exemplified by $C_{6-14}$ aryl groups such as phenyl, naphthyl, anthryl, phenanthryl and acenaphthylenyl, and phenyl, 1-naphthyl and 2-naphthyl are preferable among others.

The cycloalkyl group in the lower cycloalkyl group (4) that may be substituted, is exemplified by $C_{3-7}$ cycloalkyl groups such as cyclopropyl, cyclobutyl, cyclopentyl, cyclohexyl and cycloheptyl.

The cycloalkenyl group in the lower cycloalkenyl group (4) that may be substituted, is exemplified by $C_{3-6}$ cycloalkenyl groups such as cyclopropenyl, cyclobutenyl, cyclopentenyl and cyclohexenyl.

Said aryl group (3), said lower cycloalkyl group (4) or said lower cycloalkenyl group (4) may have 1 to 5, preferably 1 to 3, optionally chosen substituents at any possible positions, and these substituents include alkoxy groups (e.g., $C_{1-3}$ alkoxy groups such as methoxy, ethoxy and propoxy), halogen atoms (e.g., fluorine, chlorine, bromine, iodine), alkyl groups (e.g., $C_{1-3}$ alkyl groups such as methyl, ethyl and propyl), amino, nitro and cyano.

The heterocyclic group in the heterocyclic group (5) that may be substituted, is exemplified by aromatic heterocyclic groups and saturated or unsaturated non-aromatic heterocyclic groups (aliphatic heterocyclic groups) having at least 1 hetero atom selected from oxygen, sulfur and nitrogen as a ring-constituting atom (ring atom), and aromatic heterocyclic groups are preferable. Such aromatic heterocyclic groups include 5- to 7-membered aromatic heterocyclic groups containing 1 sulfur atom, nitrogen atom or oxygen atom, 5- or 6-membered aromatic heterocyclic groups containing 2 to 4 nitrogen atoms, and 5- or 6-membered aromatic heterocyclic groups containing 1 or 2 nitrogen atoms and 1 sulfur atom or oxygen atom. These aromatic heterocyclic groups may be fused with a 6-membered ring containing 2 or fewer nitrogen atoms, a benzene ring, or a 5-membered ring containing 1 sulfur atom. Such aromatic heterocyclic groups include aromatic monocyclic heterocyclic groups (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl) and aromatic fused heterocyclic groups (e.g., benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl), and preferable are furyl, fused furyl, thienyl, fused thienyl, indolyl, isoindolyl, pyrazinyl, pyridyl, pyrimidinyl, azolyl and fused azolyl groups thereof. The azolyl groups include 5-membered aromatic heterocyclic groups containing 1 to 4 nitrogen atoms (e.g., pyrrolyl, imidazolyl, pyrazolyl, triazolyl, tetrazolyl) and 5-membered aromatic heterocyclic groups containing 1 or 2 nitrogen atoms and 1 sulfur atom or oxygen atom (e.g., oxazolyl, isoxazolyl, thiazolyl, isothiazolyl), and the fused azolyl groups include groups formed by fusion of a benzene ring with a 5-membered aromatic heterocyclic ring containing 1 or 2 nitrogen atoms (e.g., benzimidazolyl) and groups formed by fusion of a benzene ring with a 5-membered aromatic heterocyclic ring containing 1 nitrogen atom and 1 sulfur atom or oxygen atom (e.g., benzoxazolyl, benzisoxazolyl, benzothiazolyl, benzisothiazolyl). Particular preferred are furyl, thienyl, indolyl, isoindolyl, pyrazinyl, pyridyl, pyrimidinyl, benzofuranyl, benzimidazolyl, benzoxazolyl, 1,2-benzisoxazolyl, benzothiazolyl, benzo[b] thienyl, oxazolyl and isoxazolyl, and furyl and thienyl are more preferred. Such non-aromatic heterocyclic groups include 5- to 7-membered non-aromatic heterocyclic groups containing 1 sulfur atom, nitrogen atom or oxygen atom, and 3- to 7-membered non-aromatic heterocyclic groups containing 1 nitrogen atom and 3 or fewer hetero atoms (e.g., nitrogen, oxygen and sulfur atoms), such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, homopiperidyl, pyrrolinyl and imidazolidinyl. These non-aromatic heterocyclic groups may be fused with a benzene ring, a 6-membered ring containing 2 or fewer nitrogen atoms, a 5-membered ring containing 1 sulfur atom, or the like. Such fused non-aromatic heterocyclic groups include chromanyl, isochromanyl, indolinyl, isoindolinyl, thiochromanyl and isothiochromanyl. The heterocyclic groups may have 1 to 3 optionally chosen substituents at any possible positions. Such substituents include alkoxy groups (e.g., $C_{1-4}$ alkoxy groups such as methoxy, ethoxy and propoxy) that may be substituted by 1 to 3 halogen atoms (e.g. fluorine, chlorine, bromine, iodine), halogen atoms (e.g., fluorine, chlorine, bromine, iodine), alkyl groups (e.g., $C_{1-4}$ alkyl groups such as methyl, ethyl and propyl) that may be substituted by 1 to 3 halogen atoms (e.g. fluorine, chlorine, bromine, iodine), aryl groups (e.g., $C_{6-10}$ aryl groups such as phenyl, 1-naphthyl and 2-naphthyl), and nitro.

The carboxyl group (6) that may be esterified include carboxyl groups, (lower ($C_{1-6}$) alkoxy)carbonyl groups (e.g., methoxycarbonyl, ethoxycarbonyl, propoxycarbonyl, isopropoxycarbonyl, butoxycarbonyl, isobutoxycarbonyl, tert-butoxycarbonyl, sec-butoxycarbonyl, pentyloxycarbonyl, isopentyloxycarbonyl, neopentyloxycarbonyl, tert-pentyloxycarbonyl, hexyloxycarbonyl), ($C_{6-10}$ aryl)oxycarbonyl groups (e.g., phenoxycarbonyl, 1-naphthoxycarbonyl) and ($C_{7-10}$ aralkyl) oxycarbonyl group (e.g., (phenyl-$C_{1-4}$ alkyl)oxycarbonyl groups such as benzyloxycarbonyl etc.), and the carboxyl group, methoxycarbonyl and ethoxycarbonyl are preferred.

The substituents in said carbamoyl group (7) that may be substituted, or in the amino group (8) that may be substituted, are exemplified by lower ($C_{1-6}$) alkyl groups that may be substituted (e.g., methyl, ethyl, propyl, isopropyl, butyl, isobutyl, sec-butyl, tert-butyl, pentyl, isopentyl, neopentyl, hexyl, isohexyl), $C_{3-6}$ cycloalkyl groups that may be substituted (e.g., cyclopropyl, cyclobutyl, cyclopentyl, cyclohexyl), $C_{6-10}$ aryl groups that may be substituted (e.g., phenyl, 1-naphthyl, 2-naphthyl), $C_{7-12}$ aralkyl groups that may be substituted (e.g., phenyl-$C_{1-4}$ alkyl groups such as benzyl and phenethyl, and naphthyl-$C_{1-2}$ alkyl groups), and $C_{6-10}$ arylsulfonyl groups that may be substituted (e.g., benzenesulfonyl, 1-naphthalenesulfonyl, 2-naphthalenesulfonyl), and 1 or 2 of these substituents, whether identical or not, may be present. The substituents in such lower ($C_{1-6}$) alkyl groups that may be substituted, $C_{3-6}$ cycloalkyl groups that may be substituted, $C_{6-10}$ aryl groups that may be substituted, $C_{7-12}$ aralkyl groups that may be substituted, and $C_{6-10}$ arylsulfonyl groups that may be substituted, include halogens (e.g., fluorine, chlorine, bromine), alkoxy groups (e.g., $C_{1-4}$ alkoxy groups such as methoxy, ethoxy and propoxy) that may be substituted by 1 to 3 halogens, alkyl groups (e.g., $C_{1-4}$ alkyl groups such as methyl, ethyl and propyl) that may be substituted by 1 to 3 halogens, and nitro, and 1 to 5 of these substituents may be present. Also, the amino group that may be substituted, may form a cyclic amino group resulting from binding of two substituents on the nitrogen atom with the nitrogen atom, and such cyclic amino groups include 1-azetidinyl, 1-pyrrolidinyl, piperidino, morpholino and 1-piperazinyl.

The substituents in said hydroxyl group (9) that may be substituted, and the thiol group (10) that may be substituted, are exemplified by hydrocarbon groups that may be substituted, and heterocyclic groups that may be substituted. The "hydrocarbon group that may be substituted" is exemplified by the same groups as those mentioned in the "hydrocarbon group that may be substituted," represented by $R^1, R^2, R^3, R^4, R^5$ or $R^6$ above, and preferable are lower ($C_{1-6}$) alkyl groups that may be substituted (e.g., methyl, ethyl, propyl, isopropyl, butyl, isobutyl, sec-butyl, tert-butyl, pentyl, isopentyl, neopentyl, hexyl, isohexyl), $C_{3-6}$ cycloalkyl groups that may be substituted (e.g., cyclopropyl, cyclobutyl, cyclopentyl, cyclohexyl), $C_{6-10}$ aryl groups that may be substituted (e.g., phenyl, 1-naphthyl, 2-naphthyl), and $C_{7-12}$ aralkyl groups (e.g., phenyl-$C_{1-4}$ alkyl groups such as benzyl and phenethyl, and naphthyl-$C_{1-2}$ alkyl groups). These lower ($C_{1-6}$) alkyl groups, $C_{3-6}$ cycloalkyl groups, $C_{6-10}$ aryl groups and $C_{7-12}$ aralkyl groups may have 1 to 5 optionally chosen substituents at any possible positions, and these substituents include halogens (e.g., fluorine, chlorine, bromine), alkoxy groups (e.g., $C_{1-4}$ alkoxy groups such as methoxy, ethoxy and propoxy) that may be substituted by 1 to 3 halogens, alkyl groups (e.g., $C_{1-4}$ alkyl groups such as methyl, ethyl and propyl) that may be substituted by 1 to 3 halogens, nitro, amino and cyano. The "heterocyclic group that may be substituted" is exemplified by the same groups as those mentioned below in the "heterocyclic group that may be substituted," represented by $R^1, R^2, R^3, R^4, R^5$ or $R^6$.

The acyl group (11) is exemplified by formyl groups, carbonyl groups substituted by a hydrocarbon group that may be substituted, sulfinyl groups substituted by a hydrocarbon group that may be substituted, and sulfonyl groups substituted by a hydrocarbon group that may be substituted. The "hydrocarbon group that may be substituted" is exemplified by the same groups as those mentioned in the "hydrocarbon group that may substituted," represented by $R^1, R^2, R^3, R^4, R^5$ or $R^6$ above, and preferable are lower ($C_{1-6}$) alkyl groups that may be substituted, $C_{3-6}$ cycloalkyl groups that may be substituted, $C_{6-10}$ aryl groups (e.g., phenyl, naphthyl) that may be substituted, and $C_{7-12}$ aralkyl groups (e.g., phenyl-$C_{1-4}$ alkyl groups, naphthyl-$C_{1-2}$ alkyl groups) that may be substituted. Preferable acyl groups include formyl groups, ($C_{1-6}$ alkyl)carbonyl groups, ($C_{3-6}$ cycloalkyl)carbonyl groups, ($C_{6-10}$ aryl)carbonyl groups, ($C_{7-12}$ aralkyl)carbonyl groups, ($C_{1-6}$ alkyl)sulfinyl groups ($C_{3-6}$ cycloalkyl)sulfinyl groups, ($C_{6-10}$ aryl)sulfinyl groups, ($C_{7-12}$ aralkyl)sulfinyl groups, ($C_{1-6}$ alkyl)sulfonyl groups, ($C_{3-6}$ cycloalkyl)sulfonyl groups, ($C_{6-10}$ aryl)sulfonyl groups and ($C_{7-12}$ aralkyl)sulfonyl groups. These acyl groups may have 1 to 5 optionally chosen substituents at any possible positions., and such substituents include halogens, alkoxy group (e.g., $C_{1-4}$ alkoxy groups) and alkyl groups (e.g., $C_{1-4}$ alkyl groups).

The heterocyclic group in the "heterocyclic group that may be substituted," represented by $R^1, R^2, R^3, R^4, R^5$ or $R^6$, is exemplified by aromatic heterocyclic groups and saturated or unsaturated non-aromatic heterocyclic groups (aliphatic heterocyclic groups) having at least 1 hetero atom selected from atoms of oxygen, sulfur and nitrogen as a ring-constituting atom (ring atom), and aromatic heterocyclic groups are preferred.

Such aromatic heterocyclic groups include 5- to 7-membered aromatic heterocyclic groups containing 1 sulfur atom, nitrogen atom or oxygen atom, 5- or 6-membered aromatic heterocyclic groups containing 2 to 4 nitrogen atoms, and 5- or 6-membered aromatic heterocyclic groups containing 1 or 2 nitrogen atoms and 1 sulfur atom or oxygen atom. These aromatic heterocyclic groups may be fused with a 6-membered ring containing 2 or fewer nitrogen atoms, a benzene ring, or a 5-membered ring containing 1 sulfur atom. Such aromatic heterocyclic groups include aromatic monocyclic heterocyclic groups (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl) and aromatic fused heterocyclic groups (e.g., benzofuranyl, isobenzofuranyl, benzo [b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo-[4,3-a]pyridyl and 1,2,4-triazolo[4,3-b]pyridazinyl), and furyl, thienyl, indolyl, isoindolyl, pyrazinyl, pyridyl, pyrimidinyl, azolyl and fused ring groups thereof are preferred. Particularly furyl, thienyl, indolyl, isoindolyl, pyrazinyl, pyridyl, pyrimidinyl, benzofuranyl, benzimidazolyl, benzoxazolyl, 1,2-benzisoxazolyl, benzothiazolyl, benzo[b]thienyl, oxazolyl and isoxazolyl are preferred, and furyl and thienyl are more preferred.

Such non-aromatic heterocyclic groups include 5- to 7-membered non-aromatic heterocyclic groups containing 1 sulfur atom, nitrogen atom or oxygen atom, and 3- to 7-membered non-aromatic heterocyclic groups containing 1 nitrogen atom and 3 or fewer hetero atoms (e.g., nitrogen, oxygen and sulfur atoms), such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, homopiperidyl, pyrrolinyl and imidazolidinyl. These non-aromatic heterocyclic groups may be fused with a benzene ring, a 6-membered ring containing 2 or fewer nitrogen atoms, a 5-membered ring containing 1 sulfur atom, or the like. Such fused non-aromatic heterocyclic groups include chromanyl, isochromanyl, indolinyl, isoindolinyl, thiochromanyl and isothiochromanyl.

The heterocyclic group in the "heterocyclic group that may be substituted," represented by $R^1, R^2, R^3, R^4, R^5$ or $R^6$ above, may have 1 to 4, preferably 1 to 3, optionally chosen substituents at any possible positions. Such substituents include (i) lower alkyl groups that may be substituted, (ii) lower alkoxy groups that may be substituted, (iii) aryl groups that may be substituted, (iv) lower cycloalkyl or cycloalkenyl groups that may be substituted, (v) heterocyclic groups that may be substituted, (vi) carboxyl groups that may be esterified, (vii) carbamoyl groups that may be substituted, (viii) amino groups that may be substituted, (ix) hydroxyl groups that may be substituted, (x) thiol groups that may be substituted, (xi) acyl groups, (xii) halogens (e.g., fluorine, chlorine, bromine), (xiii) nitro, and (xiv) cyano.

The lower alkyl group (i) that may be substituted, the lower alkoxy group (ii) that may be substituted, the aryl group (iii) that may be substituted, the lower cycloalkyl group or cycloalkenyl group (iv) that may be substituted, the heterocyclic group (v) that may be substituted, the carboxyl group (vi) that may be esterified, the carbamoyl group (vii) that may be substituted, the amino group (viii) that may be substituted, the hydroxyl group (ix) that may be substituted, the thiol group (x) that may be substituted, and the acyl group (xi), are exemplified by the same substituents as those mentioned in the substituents in the "heterocyclic group that may be substituted," represented by $R^1$, $R^2$, $R^3$, $R^4$, $R^5$ or $R^6$ above.

Particularly preferable for $R^1$, $R^2$, $R^3$, $R^4$, $R^5$ and $R^6$ are alkyl groups that may be substituted (preferably $C_{1-4}$ alkyl groups), alkenyl groups/that may be substituted (preferably $C_{2-4}$ alkenyl groups), aryl groups that may be substituted (preferably $C_{6-10}$ aryl groups such as phenyl, 1-naphthyl and 2-naphthyl), and aromatic heterocyclic groups that may be substituted (preferably furyl, benzofuranyl, thienyl, benzothienyl, indolyl, isoindolyl, pyrazinyl, pyridyl, pyrimidinyl, azolyl, or fused azolyl). These alkyl groups, alkenyl groups and aryl groups may have 1 to 3 (preferably 1 to 2) optionally chosen substituents at any possible positions. Preferable substituents include (1) lower ($C_{1-3}$) alkyl groups (e.g., methyl, ethyl, propyl, isopropyl) that may be substituted by 1 to 3 halogens (e.g., fluorine, chlorine, bromine, iodine), (2) lower ($C_{1-3}$) alkoxy groups (e.g., methoxy, ethoxy, propoxy, isopropoxy), (3) $C_{6-10}$ aryl groups (e.g., phenyl) that may be substituted by 1 to 3, preferably 1 to 2, substituents selected from halogens (e.g. fluorine, chlorine, bromine, iodine), amino, nitro and cyano, (4) $C_{6-10}$ aryloxy groups (e.g., phenoxy) that may be substituted 1 to 3, preferably 1 to 2, substituents selected from by lower ($C_{1-3}$) alkoxy groups (e.g., methoxy, ethoxy, propoxy, isopropoxy), halogens (e.g., fluorine, chlorine, bromine, iodine), nitro, cyano and amino, (5) heterocyclic groups (e.g., thienyl, benzimidazolyl, benzoxazolyl) that may be substituted by 1 to 3, preferably 1 to 2, halogens (e.g., fluorine, chlorine, bromine, iodine), (6) amino groups that may be substituted by a p-toluenesulfonyl group etc., (7) hydroxyl groups, (8) thiol groups that may be substituted by a $C_{6-10}$ aryl groups (e.g. phenyl) that may have 1 to 3 (preferably 1 to 2) substituents selected from halogens and lower ($C_{1-3}$) alkoxy groups, or by a heterocyclic group (e.g., benzoxazolyl, benzothiazolyl) that may have 1 to 3 (preferably 1 to 2) substituents selected from halogens and lower ($C_{1-3}$) alkoxy groups, (9) halogens (e.g., fluorine, chlorine, bromine), (10) nitro, and (11) cyano. These aromatic heterocyclic groups may have 1 to 3 (preferably 1 to 2) optionally chosen substituents at any possible positions. Preferable substituents include lower ($C_{1-3}$) alkyl groups that may be substituted by 1 to 3 halogens (e.g., methyl, ethyl, propyl, isopropyl, fluoromethyl, chloromethyl), $C_{6-10}$ aryl groups (e.g., phenyl), lower ($C_{1-3}$) alkoxy groups that may be substituted by 1 to 3 halogens (e.g., methoxy, ethoxy, propoxy, isopropoxy, fluoromethoxy, chloromethoxy), halogens (e.g., fluorine, chlorine, bromine), nitro, cyano, (lower $C_{1-6}$)alkyl)carbonyl groups and ($C_{1-6}$ alkyl)sulfonyl groups.

(2) The "hydrocarbon group that may be substituted" as a substituent for the "amino group that may be substituted,"
represented by R, is exemplified by the same groups as those mentioned in the "hydrocarbon group that may be substituted," represented by $R^1$, $R^2$, $R^3$, $R^4$, $R^5$ or $R^6$ above. Said hydrocarbon group may have 1 to 3 optionally chosen substituents at any possible positions. Such substituents include lower alkyl groups that may be substituted, lower alkoxy groups that may be substituted, aryl groups that may be substituted, lower cycloalkyl groups or cycloalkenyl groups that may be substituted, heterocyclic groups that may be substituted, carboxyl groups that may be esterified, carbamoyl groups that may be substituted, amino groups that may be substituted, hydroxyl groups that may be substituted, thiol groups that may be substituted, acyl groups, halogens (e.g., fluorine, chlorine, bromine), nitro, and cyano.

Such lower alkyl groups that may be substituted, lower alkoxy groups that may be substituted, aryl groups that may be substituted, lower cycloalkyl groups or cycloalkenyl groups that may be substituted, heterocyclic groups that may be substituted, carboxyl groups that may be esterified, carbamoyl groups that may be substituted, amino groups that may be substituted, hydroxyl groups that may be substituted, thiol groups that may be substituted, and acyl groups, are in the substituent in the "hydrocarbon group that may be substituted," represented by $R^1$, $R^2$, $R^3$, $R^4$, $R^5$ or $R^6$ above.

(3) The "carboxyl group that may be esterified" as a substituent in the "amino group that may be substituted," represented by R, is exemplified by groups represented by the general formula —COOR$^7$ ($R^7$ represents a hydrogen atom, a hydrocarbon group that may be substituted or a heterocyclic group that may be substituted).

Said hydrocarbon group is exemplified by the same groups as those mentioned in the "hydrocarbon group that may be substituted," represented by $R^1$, $R^2$, $R^3$, $R^4$, $R^5$ or $R^6$ above. Said hydrocarbon group may have 1 to 3 optionally chosen substituents at any possible positions. Such substituents include lower alkyl groups that may be substituted, lower alkoxy groups that may be substituted, aryl groups that may be substituted, lower cycloalkyl groups or cycloalkenyl groups that may be substituted, heterocyclic groups that may be substituted, carboxyl groups that may be esterified, carbamoyl groups that may be substituted, amino groups that may be substituted, hydroxyl groups that may be substituted, thiol groups that may be substituted, acyl groups, halogens (e.g., fluorine, chlorine, bromine), nitro, and cyano.

Such lower alkyl groups that may be substituted, lower alkoxy groups that may be substituted, aryl groups that may be substituted, lower cycloalkyl groups or cycloalkenyl groups that may be substituted, heterocyclic groups that may be substituted, carboxyl groups that may be esterified, carbamoyl groups that may be substituted, amino groups that may be substituted, hydroxyl groups that may be substituted, thiol groups that may be substituted, and acyl groups, are exemplified by the same substituents as those mentioned in the substituent in the "hydrocarbon group that may be substituted," represented by $R^1$, $R^2$, $R^3$, $R^4$, $R^5$ or $R^6$ above.

Said heterocyclic group is exemplified by the same groups as those mentioned in the heterocyclic group in the "heterocyclic group that may be substituted," represented by $R^1$, $R^2$, $R^3$, $R^4$, $R^5$ or $R^6$ above. Said heterocyclic group may have 1 to 3 optionally chosen substituents at any possible positions. Such substituents include lower alkyl groups that may be substituted, lower alkoxy groups that may be substituted, aryl groups that may be substituted, lower cycloalkyl groups or cycloalkenyl groups that may be substituted, heterocyclic groups that may be substituted, carboxyl groups that may be esterified, carbamoyl groups that may be substituted, amino groups that may be substituted, hydroxyl groups that may be substituted, thiol groups that may be substituted, acyl groups, halogens (e.g., fluorine, chlorine, bromine), nitro, and cyano.

Such lower alkyl groups that may be substituted, lower alkoxy groups that may be substituted, aryl groups that may be substituted, lower cycloalkyl groups or cycloalkenyl groups that may be substituted, heterocyclic groups that may be substituted, carboxyl groups that may be esterified, carbamoyl groups that may be substituted, amino groups that may be substituted, hydroxyl groups that may be substituted, thiol groups that may be substituted, and acyl groups, are exemplified by the same substituents as those mentioned in the substituent in the "hydrocarbon group that may be substituted," represented by $R^1$, $R^2$, $R^3$, $R^4$, $R^5$ or $R^6$ above.

Preferably groups for $R^7$ include lower ($C_{1-6}$) alkyl groups that may be substituted, lower ($C_{3-6}$) cycloalkyl groups, $C_{6-10}$ aryl groups, and $C_{7-12}$ aralkyl groups, and lower ($C_{1-3}$) alkyl groups are more preferable.

Such lower ($C_{1-6}$) alkyl groups include methyl, ethyl, propyl, isopropyl, butyl, isobutyl, sec-butyl, tert-butyl, pentyl, isopentyl, neopentyl, hexyl and isohexyl.

Such lower ($C_{3-6}$) cycloalkyl groups include cyclopropyl, cyclobutyl, cyclopentyl and cyclohexyl.

Such $C_{6-10}$ aryl groups include phenyl, 1-naphthyl and 2-naphthyl.

Such $C_{7-12}$ aralkyl groups include phenyl-$C_{1-4}$ alkyl groups such as benzyl and phenethyl, and naphthyl-$C_{1-2}$ alkyl groups.

These lower ($C_{1-6}$) alkyl groups, lower ($C_{3-6}$) cycloalkyl groups, $C_{6-10}$ aryl groups and $C_{7-12}$ aralkyl groups may have 1 to 3 optionally chosen substituents at any possible positions, and these substituents include halogens (e.g., fluorine, chlorine, bromine).

With respect to the general formula (I) above, R is preferably a group represented by the formula:

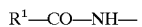

or

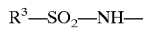

wherein $R^1$ and $R^3$ have the same meanings as defined above, and the former is more preferable.

Particularly preferable is a compound represented by formula (IA):

wherein R' represents (a) a heterocyclic group that may be substituted (excluding a furyl that may be substituted, a pyridyl group that may be substituted and a 3-amino-2-oxo-1-azetidinyl group which may be substituted) [hereinafter referred to as group Ra], (b) a hydrocarbon group substituted by a heterocyclic group that may be substituted (except a phenyl group substituted by a maleimido group which may be substituted) [hereinafter referred to as group Rb], (c) a hydrocarbon group substituted by a substituted phenoxy group [hereinafter referred to as group Rc], or (d) a hydrocarbon group substituted by a heterocyclic-thio group that may be substituted [hereinafter referred to as group Rd], or (e) an alkyl group substituted by an arylsulfonylamino group that may be substituted [hereinafter referred to as group Re]; or a compound represented by in formula (IA'):

wherein R" represents a furyl or pyridyl group having 1 to 3 substituents selected from halogens, cyano, formyl, lower ($C_{1-3}$) alkyl groups (e.g., methyl, ethyl, propyl) that may be substituted by 1 to 3 halogens (e.g., fluorine, chlorine, bromine, iodine), lower ($C_{13}$) alkoxy groups (e.g., methoxy, ethoxy, propoxy) that may be substituted by 1 to 3 halogens (e.g., fluorine, chlorine, bromine, iodine), (lower ($C_{1-3}$) alkoxy) carbonyl groups (e.g., methoxycarbonyl, ethoxycarbonyl, propoxycarbonyl) that may be substituted by 1 to 3 halogens (e.g., fluorine, chlorine, bromine, iodine), and lower ($C_{1-3}$) alkylsulfonyl groups (e.g., methylsulfonyl, ethylsulfonyl, propyl- sulfonyl) that may be substituted by 1 to 3 halogens (e.g., fluorine, chlorine, bromine, iodine).

With respect to the formula (IA), the heterocyclic group in the "heterocyclic group that may be substituted," represented by Ra, is exemplified by the same groups as those mentioned to exemplify the "heterocyclic group that may be substituted," represented by $R^1$, $R^2$, $R^3$, $R^4$, $R^5$ or $R^6$ above, and preferable are thienyl (2- or 3-thienyl), azolyl [e.g., oxazolyl (e.g., 2-, 4- or 5-oxazolyl), isoxazolyl (e.g., 3-, 4- or 5-isoxazolyl)], fused ring groups of thienyl or azolyl [e.g., benzothienyl (e.g., 2- or 3-benzo[b]thienyl), benzoxazolyl (e.g., 2-, 5- or 6-benz[d]oxazolyl), benzothiazolyl (e.g., 2-benzo[d]thiazolyl)] and fused furanyl groups [e.g., benzofuranyl (e.g., 2- or 3-benzo[b]furanyl)].

The heterocyclic group in the "heterocyclic group that may be substituted," represented by Ra, may have 1 to 3 (preferably 1 to 2) optionally chosen substituents at any possible positions. These substituents are exemplified by the same groups as those mentioned in the substituent to the "heterocyclic group that may be substituted," represented by $R^1$, $R^2$, $R^3$, $R^4$, $R^5$ or $R^6$ above, and preferable are lower ($C_{1-3}$) alkyl groups (e.g., methyl, ethyl, propyl, isopropyl, fluoromethyl, chloromethyl) that may be substituted by 1 to 3 halogens (e.g., fluorine, chlorine, bromine, iodine), $C_{6-10}$ aryl groups (e.g., phenyl), lower ($C_{1-3}$) alkoxy groups (e.g., methoxy, ethoxy, propoxy, isopropoxy, fluoromethoxy, chloromethoxy) that may be substituted by 1 to 3 halogens (e.g., fluorine, chlorine, bromine, iodine), halogens (e.g., fluorine, chlorine, bromine), nitro, cyano, ($C_{1-6}$ alkyl) carbonyl groups and ($C_{1-6}$ alkyl)sulfonyl groups.

Ra is preferably a thienyl group that may be substituted, and more preferably a thienyl group that may be substituted by a $C_{1-3}$ alkyl group.

The hydrocarbon group in the "hydrocarbon group substituted by a heterocyclic group that may be substituted," represented by Rb above, is exemplified by the same groups as those mentioned in the hydrocarbon group in the "hydrocarbon group that may be substituted," represented by $R^1$, $R^2$, $R^3$, $R^4$, $R^5$ or $R^6$ above. Said hydrocarbon group has, at any possible position, at least 1 heterocyclic group that may be substituted. Such heterocyclic groups that may be substituted are exemplified by the same groups as those mentioned in the "heterocyclic group that may be substituted" as a substituent to the "hydrocarbon group that may be substituted," represented by $R^1$, $R^2$, $R^3$, $R^4$, $R^5$ or $R^6$ above. Said hydrocarbon group may have optionally chosen substituents at any possible positions, in addition to the heterocyclic group that may be substituted, but the total number of substituents in said hydrocarbon group is preferably 1 to 3 (more preferably 1 to 2). Such substituents are exemplified by the same groups as those mentioned in the substituent to the "hydrocarbon group that may be substituted," represented by $R^1$, $R^2$, $R^3$, $R^4$, $R^5$ or $R^6$ above.

Rb is preferably a hydrocarbon group substituted by an aromatic heterocyclic group that may be substituted [e.g., thienyl (e.g., 2- or 3-thienyl), furyl (e.g., 2- or 3-furyl), azolyl [e.g., oxazolyl (e.g., 2-, 4- or 5-oxazolyl), isoxazolyl (e.g., 3-, 4- or 5-isoxazolyl)], fused ring groups of thienyl, furyl or azolyl [benzothienyl (e.g., 2- or 3-benzo[b]thienyl), benzofuranyl (e.g., 2- or 3-benzo[b]furanyl), benzoxazolyl (e.g., 2-, 5- or 6-benz[d]oxazolyl), benzisoxazolyl (e.g., 3-, 4- or 5-benz[d]isoxazolyl), benzothiazolyl (e.g., 2-benzo[d]-thiazolyl), benzimidazolyl (e.g., 1-benz[d]imidazolyl)]]. More preferable is a hydrocarbon group substituted by a thienyl or furyl group that may be substituted. Preferable hydrocarbon groups include $C_{1-10}$ alkyl groups (preferably $C_{1-3}$ alkyl groups such as methyl, ethyl and propyl) and $C_{2-10}$ alkenyl groups (preferably $C_{2-4}$ alkenyls such as ethenyl). Said aromatic heterocyclic group may have 1 to 3 optionally chosen substituents at any possible positions, and preferable substituents include lower ($C_{1-3}$) alkyl groups (e.g., methyl, ethyl, propyl, isopropyl, fluoromethyl, chloromethyl) that may be substituted by 1 to 3 halogens (e.g., fluorine, chlorine, bromine, iodine), $C_{6-10}$ aryl groups (e.g., phenyl), lower ($C_{1-3}$) alkoxy groups (e.g., methoxy, ethoxy, propoxy, isopropoxy, fluoromethoxy, chloromethoxy) that may be substituted by 1 to 3 halogens (e.g., fluorine, chlorine, bromine, iodine), halogens (e.g., fluorine, chlorine, bromine, iodine), and nitro. The hydrocarbon group may have a substituent such as a cyano group in addition to the aromatic heterocyclic group that may be substituted.

The "hydrocarbon group substituted for by a substituted phenoxy group," represented by Rc above, is exemplified by hydrocarbon groups substituted by a phenoxy group that is substituted by 1 to 3 substituents selected from an alkoxy group (e.g., $C_{1-3}$ alkoxy groups such as methoxy, ethoxy, propoxy and isopropoxy) that may be substituted by 1 to 3 halogens (e.g., fluorine, chlorine, bromine, iodine), a nitro group, a halogen (e.g., fluorine, chlorine, bromine, iodine), a cyano group, an amino group and an alkyl group (e.g., $C_{1-3}$ alkyl groups such as methyl, ethyl, propyl and isopropyl) that may be substituted by 1 to 3 halogens (e.g., fluorine, chlorine, bromine, iodine).

The hydrocarbon group in the "hydrocarbon group substituted by a substituted phenoxy group," represented by Rc above, is exemplified by the same hydrocarbon groups as those mentioned in the hydrocarbon group in the "hydrocarbon group substituted by a substituted phenoxy group," represented by Rb. Said hydrocarbon group is preferably a lower ($C_{1-6}$) alkyl group. Said hydrocarbon group may have 1 to 2 optionally chosen substituents at any possible positions, in addition to the substituted phenoxy group. Such substituents are exemplified by the same groups as those mentioned in the substituent to the "hydrocarbon group that may be substituted," represented by $R^1$, $R^2$, $R^3$, $R^4$, $R^5$ or $R^6$ above.

The hydrocarbon group in the "hydrocarbon group substituted by a heterocyclic-thio group that may be substituted," represented by Rd above, is exemplified by the same groups as those mentioned in the hydrocarbon group in the "hydrocarbon group that may be substituted," represented by $R^1$, $R^2$, $R^3$, $R^4$, $R^5$ or $R^6$ above. Said hydrocarbon group has, at any possible position, at least 1 "heterocyclic-thio group that may be substituted". The heterocyclic ring that may be substituted in said "heterocyclic-thio group that may be substituted" is exemplified by the same groups as those mentioned in the "heterocyclic group that may be substituted" as a substituent to the "hydrocarbon group that may be substituted," represented by $R^1$, $R^2$, $R^3$, $R^4$, $R^5$ or $R^6$ above. Said hydrocarbon group may have optionally chosen substituents at any possible positions, in addition to the heterocyclic-thio group that may be substituted, but the total number of substituents in said hydrocarbon group is preferably 1 to 3 (more preferably 1 to 2). Such substituents are exemplified by the same groups as those mentioned in the substituent to the "hydrocarbon group that may be substituted," represented by $R^1$, $R^2$, $R^3$, $R^4$, $R^5$ or $R^6$ above.

Rd is preferably a hydrocarbon group substituted by a thiol (mercapto) group that is substituted by an aromatic heterocyclic group that may be substituted [e.g., thienyl (e.g., 2- or 3-thienyl), furyl (e.g., 2- or 3-furyl), azolyl [e.g., oxazolyl (e.g., 2-, 4- or 5-oxazolyl), isoxazolyl (e.g., 3-, 4- or 5-isoxazolyl)], fused ring groups of thienyl, furyl or azolyl [e.g., benzothienyl (e.g., 2- or 3-benzo[b]thienyl), benzofuranyl (e.g., 2- or 3-benzo[b]furanyl), benzoxazolyl (e.g., 2-, 5- or 6-benz-[d]oxazolyl), benzisoxazolyl (e.g., 3-, 4- or 5-benz[d]isoxazolyl), benzothiazolyl (e.g., 2-benzo[d] thiazolyl) benzimidazolyl (e.g., 1-benz[d]imidazolyl)]]. Preferable hydrocarbon groups include $C_{1-10}$ alkyl groups (preferably $C_{1-3}$ alkyl groups such as methyl, ethyl and propyl) and $C_{2-10}$ alkenyl group (preferably $C_{2-4}$ alkenyl groups such as ethenyl). The aromatic heterocyclic group in said aromatic heterocyclic group that may be substituted may have, at any possible positions, 1 to 3 (preferably 1 to 2) optionally chosen substituents. Preferable substituents include lower ($C_{1-3}$) alkyl groups (e.g., methyl, ethyl, propyl, isopropyl) that may be substituted by 1 to 3 halogens, $C_{6-10}$ aryl groups (e.g., phenyl), lower ($C_{1-3}$) alkoxy groups (e.g., methoxy, ethoxy, propoxy, isopropoxy) that may be substituted by 1 to 3 halogens, halogens (e.g., fluorine, chlorine, bromine, iodine) and nitro.

The "alkyl group substituted by an arylsulfonylamino group that may be substituted," represented by Re above, is exemplified by $C_{1-10}$ alkyl groups (preferably $C_{1-3}$ alkyl groups such as methyl, ethyl and propyl) substituted by a $C_{6-10}$ aryl (e.g., phenyl, naphthyl)-sulfonylamino group. Said "alkyl group substituted by an arylsulfonylamino group that may be substituted" may have, at any possible positions, 1 to 3 (preferably 1 to 2) optionally chosen substituents. Preferable substituents include lower ($C_{1-3}$) alkyl groups (e.g., methyl, ethyl, propyl, isopropyl) that may be substituted by 1 to 3 halogens, $C_{6-10}$ aryl groups (e.g., phenyl), lower ($C_{1-3}$) alkoxy groups (e.g., methoxy, ethoxy, propoxy, isopropoxy) that may be substituted by 1 to 3 halogens, halogens (e.g., fluorine, chlorine, bromine, iodine) and nitro.

With respect to the formula (IA), R' is preferably a thienyl group that may have 1 to 3 (preferably 1 to 2) substituents selected from a $C_{1-3}$ alkyl group which may be substituted by 1 to 3 halogens, a $C_{1-3}$ alkoxy group, a halogen atom, a nitro group, a cyano group, a ($C_{1-6}$ alkyl)carbonyl group and a ($C_{1-6}$ alkyl)sulfonyl group, and more preferably a thienyl group that may be substituted by a $C_{1-3}$ alkyl group.

With respect to the formula (IA'), R" is preferably a furyl group substituted by a halogen atom (e.g., fluorine, chlorine, bromine, iodine). R" is also preferably a furyl group substituted by a $C_{1-3}$ alkyl group.

In the present invention, the salt of the compound represented by the general formula (I), (IA) or (IA') is preferably a pharmaceutically acceptable salt, exemplified by salts with inorganic bases, salts with organic bases, salts with inorganic acids, salts with organic acids and salts with basic or acidic amino acids. Preferable salts with inorganic bases include alkali metal salts such as sodium salt and potassium salt; alkaline earth metal salts such as calcium salt and magnesium salt; and aluminum salt. Preferable salts with organic bases include ammonium salts and salts with trimethylamine, triethylamine, pyridine, picoline, ethanolamine, diethanolamine, triethanolamine, dicyclohexylamine and N,N'-dibenzylethylenediamine. Preferable salts with inorganic acids include salts with hydrochloric acid, hydrobromic acid, nitric acid, sulfuric acid and phosphoric acid. Preferable salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. Preferable salts with basic amino acids include salts with arginine, lysine and ornithine. Preferable salts with acidic amino acids include salts with aspartic acid and glutamic acid. These salts can be obtained by conventional methods. Hydrates and non-hydrates of the compound represented by the general formula (I), (IA) or (IA') are included in the scope of the present invention.

The salt of the compound represented by the general formula (II) or (III) below is exemplified by the same kinds of salts as those mentioned as the salt of the compound represented by the general formula (I) above.

Production methods for compounds of the present invention are hereinafter described.

The desired compound can be produced by reacting a compound represented by the formula (II):

wherein the symbol has the same meanings as defined above, or a salt thereof, with phosphorus pentachloride, then reacting the resulting compound or a salt thereof with formic acid to yield a compound represented by the formula (III):

wherein the symbol has the same meanings as defined above, or a salt thereof, and then reacting it with ammonia.

The desired compound can also be produced by reacting a compound represented by the formula (II) or a salt thereof with phosphorus oxychloride to yield a compound represented by the formula (III) or a salt thereof, and reacting it with ammonia.

In the reaction of a compound represented by the formula (II) or a salt thereof with phosphorus pentachloride or phosphorus oxychloride, any solvent can be used, as long as it does not interfere the reaction, and such a solvent includes halogenated solvents such as carbon tetrachloride, chloroform, dichloromethane and 1,2-dichloroethane, ether solvents such as dioxane, tetrahydrofuran and diethyl ether, and hydrocarbon solvents such as benzene and toluene, and the reaction temperature is about −50° to 100° C., preferably about −20° to 80° C. The amount of phosphorus pentachloride or phosphorus oxychloride used is 1 to 10 mole equivalents, preferably 0.5 to 2 mole equivalents, per mole of the compound represented by the formula (II) or salt thereof. In the reaction with formic acid of the compound or its salt obtained by reacting the compound represented by the formula (II) or its salt with phosphorus pentachloride, halogenated solvents, ether solvents and hydrocarbon solvents as those mentioned above can be used. The reaction temperature is about −50° to 50° C., preferably about 0° to 30° C. The amount of formic acid used is 0.5 to 10 mole equivalents, preferably 1 to 3 mole equivalents, per mole of the compound obtained by reacting the compound represented by the formula (II) or its salt with phosphorus pentachloride. In the reaction of the compound represented by the formula (III) or its salt with ammonia, halogenated solvents, ether solvents and hydrocarbon solvents as those mentioned above can be used. The reaction temperature is about −50° to 50° C., preferably about −20° to 10° C.

The compound (I) or its salt may be isolated and purified by known separation and purification methods such as concentration, concentration under reduced pressure, distillation, fractional distillation, solvent extraction, chromatography, crystallization and recrystallization.

In the compounds or salts thereof to be used for the above reactions, a protecting group may be used for an amino group, carboxyl group or hydroxyl group not involved in the reaction. The addition and removal of the protecting group can be achieved by known means.

Useful amino group-protecting groups include formyl, and $C_{1-6}$ alkylcarbonyl (e.g., acetyl, propionyl), phenylcarbonyl, $C_{1-6}$ alkyl-oxycarbonyl (e.g., methoxycarbonyl, ethoxycarbonyl), phenyloxycarbonyl, $C_{7-10}$ aralkyloxy-carbonyl (e.g., phenyl-$C_{1-4}$ alkyloxy-carbonyl such as benzyloxycarbonyl), trityl, phthaloyl and N,N-dimethylaminomethylene that may be substituted. Useful substituents to these protecting groups include halogen atoms (e.g., fluorine, chlorine, bromine, iodine), formyl, $C_{1-6}$ alkyl-carbonyl (e.g., acetyl, propionyl, valeryl) and nitro groups, and the number of substituents is about 1 to 3.

Useful carboxyl group-protecting groups include $C_{1-6}$ alkyl (e.g., methyl, ethyl, propyl, isopropyl, butyl, tert-butyl), phenyl, trityl and silyl that may be substituted. Useful substituents to these protecting groups include halogen atoms (e.g., fluorine, chlorine, bromine, iodine), formyl, $C_{1-6}$ alkyl-carbonyls (e.g., acetyl, propionyl, valeryl) and nitro groups, and the number of substituents is about 1 to 3.

Useful hydroxyl group-protecting groups include $C_{1-6}$ alkyl (e.g., methyl, ethyl, propyl, isopropyl, butyl, tert-butyl), phenyl, $C_{7-10}$ aralkyl (e.g., phenyl-$C_{1-4}$ alkyl such as benzyl), formyl, $C_{1-6}$ alkyl-carbonyl (e.g., acetyl, propionyl), phenyloxycarbonyl, benzoyl, ($C_{7-10}$ aralkyloxy) carbonyl (e.g., phenyl-$C_{1-4}$ alkyloxy-carbonyl such as benzyloxycarbonyl), pyranyl, furanyl and silyl that may be substituted. Useful substituents to these protecting groups include halogen atoms (e.g., fluorine, chlorine, bromine, iodine), $C_{1-6}$ alkyl (e.g., methyl, ethyl, propyl), phenyl, $C_{7-10}$ aralkyl (e.g., phenyl-$C_{1-4}$ alkyl such as benzyl) and nitro groups, and the number of substituents is about 1 to 4.

Protecting groups can be removed by per se known methods or similar methods thereto, such as treatment with acid, base, reducing agent, ultraviolet rays, hydrazine, phenylhydrazine, sodium N-methyldithiocarbamate, tetrabutylammonium fluoride, palladium acetate etc.

The anti-Helicobacter agent of the present invention is characterized by containing of a compound represented by the general formula (I), (IA) or (IA') or a pharmaceutically acceptable salt thereof (hereinafter referred to as a compound represented by the general formula (I) or salt thereof).

The anti-Helicobacter agent of the present invention can be produced by known preparation methods of pharmaceutical formulation, except that a compound represented by the general formula (I) or the salt is incorporated.

The anti-Helicobacter agent of the present invention can be used orally or non-orally by inhalation, by rectal administration or by local administration. For example, it can be used in a form of powder, granule, tablet, pill, capsule, injectable preparation, syrup, emulsion, elixir, suspension, solutions etc., and it may contain at least one compound represented by the general formula (I) or a salt thereof singly or in combination with a pharmaceutically acceptable carrier. When the anti-Helicobacter agent of the present invention is formulated with a carrier, the content of the compound represented by the general formula (I) or its salt may be chosen as appropriate depending upon the preparation, but normally 1 to 100% by weight, preferably 1 to 20% by weight.

The pharmaceutically acceptable carriers include various organic or inorganic carrier substances commonly used as pharmaceutical materials, including excipients, lubricants, binders and disintegrating agents for solid preparations, and solvents, solubilizers, suspending agents, isotonizing agents, buffers and soothing agents for liquid preparations. Other pharmaceutical additives such as preservatives, antioxidants, coloring agents and sweetening agents may be used when necessary.

Preferable excipients include lactose, sucrose, D-mannitol, starch, crystalline cellulose and light silicic anhydride.

Preferable lubricants include magnesium stearate, calcium stearate, talc and colloidal silica.

Preferable binders include crystallinecellulose, sucrose, D-mannitol, dextrin, hydroxypropylcellulose, hydroxypropyl methylcellulose and polyvinylpyrrolidone.

Preferable disintegrating agents include starch, carboxymethylcellulose, carboxymethylcellulose calcium, croscarmellose sodium and carboxymethyl starch sodium.

Preferable solvents include water for injection, alcohol, propylene glycol, macrogol, sesame oil and corn oil.

Preferable solubilizers include polyethyleneglycol, propylene glycol, D-mannitol, benzyl benzoate, ethanol, Tris-aminomethane, cholesterol, triethanolamine, sodium carbonate and sodium citrate.

Preferable suspending agents include surfactants such as stearyltriethanolamine, sodium lauryl sulfate, laurylaminopropionic acid, lecithin, benzalkonium chloride, benzethonium chloride and glycerol monostearate; and hydro- philic polymers such as polyvinyl alcohol, polyvinylpyrrolidone, carboxymethylcellulose sodium, methylcellulose, hydroxymethylcellulose, hydroxyethylcellulose and hydroxypropylcellulose.

Preferable isotonizing agents include sodium chloride, glycerol and D-mannitol.

Preferable buffers include buffer solutions of phosphates, acetates, carbonates and citrates.

Preferable soothing agents include benzyl alcohol.

Preferable preservatives include p-oxybenzoic acid esters, chlorobutanol, benzyl alcohol, phenethyl alcohol, dehydroacetic acid and sorbic acid.

Preferable antioxidants include sulfites and ascorbic acid.

Pharmaceutical compositions can be prepared as pharmaceutical preparations by ordinary methods. In the present specification, "non-oral" includes subcutaneous injection, intravenous injection, intramuscular injection, intraperitoneal injection and drip infusion. Injectable preparations, e.g., aqueous or oily suspensions for aseptic injection, can be prepared by methods known in relevant fields, using an appropriate dispersing agent or wetting agent and a suspending agent. The aseptic injectable preparation thus obtained may be an aseptically injectable solution or suspension in a diluent or solvent which permits non-toxic non-oral administration, such as an aqueous solution. Acceptable vehicles or solvents include water, Ringer's solution and isotonic saline. It is also possible to use aseptic non-volatile oils as solvents or suspending media. For this purpose any non-volatile oil or fatty acid can be used, including natural, synthetic or semi-synthetic fatty oils or fatty acids, and natural, synthetic or semi-synthetic mono- or di- or tri-glycerides.

Suppositories for rectal administration may be pro- duced by mixing the drug with an appropriate non-irritative shaping agent, such as cacao butter or polyethyleneglycol, which is solid at atmospheric temperature and which is liquid at intestinal temperature and melts and releases the drug in the rectum.

Solid dosage forms for oral administration include the above-mentioned forms such as powders, granules, tablets, pills and capsules. In these dosage forms, the active ingredient compound may be mixed with at least one additive such as sucrose, lactose, cellulose sugar, mannitol, maltitol, dextran, starch, agar, alginate, chitin, chitosan, pectin, gum tragacanth, gum arabic, gelatin, collagen, casein, albumin, synthetic or semi-synthetic polymer or glyceride. Such dosage forms may additionally contain additives as usual, including inert diluents, lubricants such as magnesium stearate, preservatives such as paraben and sorbic acid, antioxidants such as ascorbic acid, $\alpha$-tocopherol and cysteine, disintegrating agents, binders, thickening agents, buffers, sweeteners, flavoring agents and perfumes. Tablets and pills may be produced with enteric coating. Liquid dosage forms for oral administration include pharmaceutically acceptable emulsions, syrups, elixirs, suspensions and solutions, and may contain inert diluents, such as water, commonly used in relevant fields.

The anti-Helicobacter agent of the present invention may also be an enteric preparation (preferably enteric preparation for oral administration).

The dose for a particular patient is determined ac- cording to age, body weight, general health status, sex, dietary status, administration time, method of administration, excretion rate, drug combination, severity of the illness being treated and other factors.

Since the compound represented by the general formula (I) or its salt exhibits antibacterial action, especially against Helicobacter bacteria, based on urease inhibitory activity, it is useful in the prevention or treatment of digestive diseases presumably caused by Helicobacter bacteria, such as gastritis, duodenal ulcer, gastric ulcer and chronic gastritis. Since significant correlation between Helicobacter bacteria, especially *Helicobacter pylori*, and gastric cancer has recently been suggested, this compound is also expected to be useful in the prevention of gastric cancer. Furthermore, the compound represented by the general formula (I) or its salt is of low toxicity and can be safely used.

Because the anti-Helicobacter agent of the present invention possesses antibacterial activity against Helicobacter bacteria, it exhibits anti-Helicobacter action against Helicobacter bacteria which exhibit toxic action in the digestive tract. The digestive tract is exemplified by the stomach and duodenal. A Helicobacter bacterium exhibiting toxic action in the digestive tract is *Helicobacter pylori*.

The daily dose of the anti-Helicobacter agent of the present invention is chosen as appropriate, depending on type and symptoms of ulcer, but the compound represented by the general formula (I) or its salt may be administered at about 0.1 to 10 g/day, preferably 0.2 to 2 g/day per adult (50 kg) by oral administration, and about 0.01 to 1 g/day, preferably 0.02 to 0.5 g/day by non-oral administration. The dose per administration is determined taking into consideration such daily doses, dosage forms etc. Administration frequency is not limited, but preferably 1 to 5 times/day, more preferably 1 to 3 times/day.

The anti-Helicobacter agent of the present invention may contain antacids, acid secretion inhibitors etc. to prevent decomposition of its active ingredient, i.e., the compound represented by the general formula (I) or its salt, by acid under acidic conditions such as the intragastric environment.

Such antacids include aluminum hydroxide gel, sodium bicarbonate, aminoacetic acid, aluminum silicate, magnesium metasilicic aluminate, magnesium silicate, magnesium oxide, magnesium hydroxide, magnesium carbonate and calcium carbonate.

Such acid secretion inhibitors include proton pump inhibitors and histamine $H_2$ blockers. The term proton pump inhibitor is defined as a drug that suppresses acid secretion by directly or indirectly inhibiting H/K-ATPase, which functions as a proton pump in gastric mucosal membrane acid secreting cells (parietal cells). Examples of such drugs include omeprazole, lansoprazole, pantoprazole, pariprazole sodium, leminoprazole, TY-11345, TU-199, FPL-65372, BY-686, tannic acid, ellagic acid, Ebselen, AHR-9294, Cassigarol-A, Bafilomycin, Y-25942, Xanthoangelol E, SKF-96356, epigallocatechin gallate, WY-27198, T-330 and SK&F-20054.

Example of proton pump inhibitors include benzimidazole compounds, which exhibits proton pump inhibiting action and are of low toxicity. Preferable benzimidazole compounds include 2-[(pyridyl)-methylsulfinyl or -methylthio]benzimidazole, derivatives thereof and salts thereof. More preferable are a compound represented by the following general formula (a) and a salt thereof:

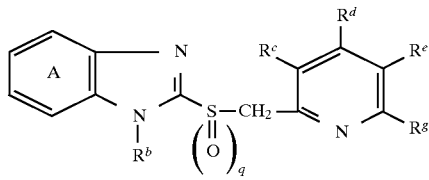

wherein ring A may be substituted; $R^b$ represents a hydrogen atom, an alkyl group, an acyl group, a carbalkoxy group, a carbamoyl group, an alkylcarbamoyl group, a dialkylcarbamoyl group or an alkylsulfonyl group; $R^c$, $R^e$ and $R^g$ independently represent a hydrogen atom, an alkyl group, an alkoxy group or an alkoxyalkoxy group; $R^d$ represents a hydrogen atom, an alkyl group or a group represented by the formula —$OR^f$ or —$SR^f$ ($R^f$ represents a hydrocarbon group that may be substituted); and q represents 0 or 1.

The benzimidazole compounds are described in Japanese Patent Unexamined Publication Nos. 62275/1977, 141783/1979, 53406/1982, 135881/1983, 192880/1983, 181277/1984, 50978/1986, 116576/1987, 277322/1987, 258320/1987, 258316/1987, 6270/1989, 79177/1989, 59043/1993, 111980/1987 and 117268/1993, and European Patent Publication Nos. 166287 and 519365, for instance.

With respect to general formula (α) above, the substituents to ring A include halogen atoms, alkyl groups that may be substituted, cycloalkyl groups that may be substituted, alkenyl groups that may be substituted, alkoxy groups that may be substituted, cyano groups, carboxy groups, carbalkoxy groups, carbalkoxyalkyl groups, carbamoyl groups, carbamoylalkyl groups, hydroxy groups, hydroxyalkyl groups, acyl groups, carbamoyloxy groups, nitro groups, acyloxy groups, aryl groups, aryloxy groups, alkylthio groups and alkylsulfinyl groups.

The above-mentioned substituents are described below.

Halogen atoms include fluorine, chlorine, bromine and iodine. Of these halogen atoms, fluorine and chlorine are preferred, and fluorine is more preferred.

The alkyl group in the alkyl group mthat may be substituted is exemplified by linear or branched alkyl groups having 1 to 10 carbon atoms (e.g., methyl, ethyl, n-propyl, isopropyl, n-butyl, isobutyl, sec-butyl, tert-butyl, n-pentyl, isopentyl, neopentyl, hexyl, heptyl, octyl, nonyl, decyl). Of these alkyl groups, linear or branched alkyl groups having 1 to 6 carbon atoms are preferred, and those having 1 to 3 carbon atoms are more preferred. Substituents said alkyl group include halogens, nitro, amino groups (which may have 1 to 2 alkyl groups, acyl groups etc. as substituents), cyano groups, hydroxy groups, carboxy groups, amidino groups, guanidino groups and carbamoyl groups.

The cycloalkyl group in the cycloalkyl group that may be substituted for is exemplified by cycloalkyl groups having 3 to 7 carbon atoms. Specifically, such cycloalkyl groups include cyclopropyl, cyclobutyl, cyclopentyl, cyclohexyl and cycloheptyl. Said cycloalkyl group may have substituents, exemplified by halogens, nitro groups, amino groups (which may have 1 to 2 alkyl groups, acyl groups etc. as substituents), cyano groups, hydroxyl groups, carboxyl groups, amidino groups, guanidino groups and carbamoyl groups.

The alkenyl group in the alkenyl group that may be substituted for is preferably exemplified by linear or branched alkenyl groups having 2 to 16 carbon atoms. Specifically, such alkenyl groups include allyl, vinyl, crotyl, 2-penten-1-yl, 3-penten-1-yl, 2-hexen-1-yl, 3-hexen-1-yl, 2-methyl-2-propen-1-yl and 3-methyl-2-buten-1-yl. Of these alkenyl groups, linear or branched alkenyl groups having 2 to 6 carbon atoms are preferred, and those having 2 to 4 carbon atoms are more preferred. Said alkenyl group may have substituents, exemplified by halogens, nitro groups, amino groups (which may have 1 to 2 alkyl groups, acyl groups etc. as substituents), cyano groups, amidino groups and guanidino groups. Said alkenyl group includes isomers (E- and Z-isomers) with respect to double bond.

The alkoxy group in the alkoxy group that may be substituted is exemplified by alkoxy groups having 1 to 10 carbon atoms. Specifically, such alkoxy groups include methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, cyclobutoxy, cyclopentoxy and cyclohexyloxy. Of these alkoxy groups, those having 1 to 6 carbon atoms are preferred, and those having 1 to 3 carbon atoms are more preferred. Said alkoxy group may have substituents, exemplified by halogens, nitro groups, amino groups (which may have 1 to 2 alkyl groups, acyl groups etc. as substituents), amidino groups, guanidino groups, $C_{1-4}$ alkoxy groups and $C_{6-10}$ aryl groups such as phenyl and naphthyl (which may have 1 to 3 halogens, $C_{1-4}$ alkyl groups, $C_{1-4}$ alkoxy groups etc. as substituents).

The substituent halogen to the above-mentioned alkyl groups, cycloalkyl groups, alkenyl groups and alkoxy groups includes chlorine, bromine, fluorine and iodine.

The alkyl group in the alkylamino group as a substituent to the above-mentioned alkyl groups, cycloalkyl groups, alkenyl groups and alkoxy groups is preferably a linear or branched alkyl group having 1 to 6 carbon atoms. Such alkyl groups include methyl, ethyl, n-propyl, isopropyl, n-butyl, isobutyl, tert-butyl, sec-butyl, n-pentyl, isopentyl, n-hexyl and isohexyl. Of these alkyl groups, linear or branched alkyl groups having 1 to 4 carbon atoms are more preferred.

The acyl group in the acylamino group as a substituent to the above-mentioned alkyl groups, cycloalkyl groups, alkenyl groups and alkoxy groups is exemplified by acyl groups derived from organic carboxylic acids. Of these acyl groups, alkanoyl groups having 1 to 6 carbon atoms are preferred. Such acyl groups include formyl, acetyl, propionyl, butyryl, isobutyryl, valeryl, isovaleryl, pivaloyl and hexanoyl, and alkanoyl groups having 1 to 4 carbon atoms are more preferred.

The number of substituents to the above-mentioned alkyl groups, cycloalkyl groups, alkenyl groups and alkoxy groups is 1 to 6, preferably 1 to 3.

Substituted alkyl groups include trifluoromethyl, trifluoroethyl, difluoromethyl, trichloromethyl, hydroxymethyl, 1-hydroxyethyl, 2-hydroxyethyl, methoxyethyl, ethoxyethyl, 1-methoxyethyl, 2-methoxyethyl, 2,2-dimethoxy-ethyl, 2,2-diethoxyethyl and 2-diethylphosphorylethyl. Of these groups, difluoromethyl, trifluoromethyl and hydroxymethyl are preferred, and trifluoromethyl is more preferred.

Substituted cycloalkyl groups include 2-aminocyclopropan-1-yl, 4-hydroxycyclopentan-1-yl and 2,2-difluoro-cyclopentan-1-yl.

Substituted alkenyl groups include 2,2-dichlorovinyl, 3-hydroxy-2-propen-1-yl and 2-methoxyvinyl.

Substituted alkoxy groups include difluoromethoxy, trifluoromethoxy, 2,2,2-trifluoroethoxy, 2-methoxyethoxy, 4-chlorobenzyloxy and 2-(3,4-dimethoxyphenyl)ethoxy. Of these alkoxy groups, difluoromethoxy is preferred.

The alkoxy group in the carbalkoxy group (alkoxycarbonyl group) is exemplified by alkoxy groups having 1 to 7 carbon atoms (e.g., methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy).

The alkoxy group in the carbalkoxyalkyl group (alkoxycarbonylalkyl group) is exemplified by alkoxy groups having 1 to 4 carbon atoms (e.g., methoxy, ethoxy, n-propoxy, isopropoxy, n-butoxy, isobutoxy, sec-butoxy, tert-butoxy), and the alkyl group is exemplified by alkyl groups having 1 to 4 carbon atoms (e.g., methyl, ethyl, n-propyl, isopropyl, n-butyl, isobutyl, sec-butyl, tert-butyl). Examples of such carbalkoxyalkyl groups include carbomethoxymethyl (methoxycarbonylmethyl), 2-carbomethoxyethyl (2-methoxycarbonylethyl), 2-carbomethoxypropyl (2-methoxycarbonylpropyl), carbethoxymethyl (ethoxycarbonylmethyl), 2-carbethoxyethyl (2-ethoxycarbonylethyl), 1-carbomethoxypropyl (1-methoxycarbonylpropyl), carbopropoxymethyl (propoxycarbonylmethyl) and carbobutoxymethyl (butoxycarbonylmethyl).

The alkyl group in the carbamoylalkyl group is exemplified by alkyl groups having 1 to 4 carbon atoms (e.g., methyl, ethyl, n-propyl, isopropyl, n-butyl, isobutyl, sec-butyl, tert-butyl).

The alkyl group in the hydroxyalkyl group is exemplified by alkyl groups having 1 to 7 carbon atoms (e.g., methyl, ethyl, n-propyl, isopropyl, n-butyl, isobutyl, sec-butyl, tert-butyl, n-pentyl, isopentyl, neopentyl, hexyl, heptyl).

The acyl group and the acyl group in the acyloxy group are exemplified by alkanoyl groups having 1 to 4 carbon atoms, including formyl, acetyl, propionyl, butyryl and isobutyryl.

The aryl group and the aryl group in the aryloxy group are exemplified by aryl groups having 6 to 12 carbon atoms (e.g., phenyl, naphthyl).

The alkyl group in the alkylthio group and alkylsulfinyl group is exemplified by alkyl groups having 1 to 6 carbon atoms (e.g., methyl, ethyl, n-propyl, isopropyl, n- butyl, isobutyl, sec-butyl, tert-butyl, n-pentyl, isopentyl, neopentyl, hexyl).

The number of substituents to the substituted ring A is preferably 1 to 4, and more preferably 1 to 2. The positions of substituents on the benzene ring include 4-and 5-positions (4- and 5-positions of benzimidazole skeleton), and 5-position is preferable.

Preferred examples of ring A include benzene ring which may be substituted by a halogen atom, an alkyl group that may be substituted, a cycloalkyl group that may be substituted, an alkenyl group that may be substituted, an alkoxy group that may be substituted, or the like.

The alkyl group represented by $R^b$ is exemplified by alkyl groups having 1 to 5 carbon atoms (e.g., methyl, ethyl, n-propyl, isopropyl, n-butyl, isobutyl, sec-butyl, tert-butyl, n-pentyl, isopentyl, neopentyl); the acyl group is exemplified by acyl groups having 1 to 4 carbon atoms (e.g., alkanoyl groups having 1 to 4 carbon atoms); the alkoxy group in the carbalkoxy group (alkoxycarbonyl group) is exemplified by alkoxy groups having 1 to 4 carbon atoms (e.g., methoxy, ethoxy, propoxy, butoxy, isobutoxy, sec-butoxy); the alkyl group in the alkylcarbamoyl group and the dialkylcarbamoyl group is exemplified by alkyl groups having 1 to 4 carbon atoms (e.g., methyl, ethyl, n-propyl, isopropyl, n-butyl, isobutyl, sec-butyl, tert-butyl); and the alkyl group of the alkylsulfonyl group is exemplified by the above-mentioned alkyl groups having 1 to 4 carbon atoms. $R^b$ is preferably a hydrogen atom.

The alkyl group represented by $R^c$, $R^e$ or $R^g$ is exemplified by linear or branched alkyl groups having 1 to 10 carbon atoms (e.g., methyl, ethyl, n-propyl, isopropyl, n-butyl, isobutyl, sec-butyl, tert-butyl, n-pentyl, isopentyl, neopentyl, hexyl, heptyl, octyl, nonyl, decyl). Of these alkyl groups, linear or branched alkyl groups having 1 to 6 carbon atoms are preferred, and linear or branched alkyl groups having 1 to 3 carbon atoms are more preferred.

The alkoxy group represented by $R^c$, $R^e$ or $R^g$ is exemplified by alkoxy groups having 1 to 10 carbon atoms (e.g., methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy). Of these alkoxy groups, alkoxy groups having 1 to 6 carbon atoms are preferred, and alkoxy groups having 1 to 3 carbon atoms are more preferred.

Each of the alkoxy groups of the alkoxyalkoxy group represented by $R^c$, $R^e$ or $R^g$ is exemplified by alkoxy groups having 1 to 4 carbon atoms (e.g., methoxy, ethoxy, n-propoxy, isopropoxy, n-butoxy, isobutoxy, sec-butoxy, tert-butoxy).

$R^c$ is preferably a hydrogen atom, an alkyl group or an alkoxy group. $R^e$ is preferably a hydrogen atom, an alkyl group or an alkoxy group. $R^g$ is preferably a hydrogen atom.

The alkyl group represented by $R^d$ is exemplified by alkyl groups having 1 to 4 carbon atoms (e.g. methyl, ethyl, n-propyl, isopropyl, n-butyl, isobutyl, sec-butyl, tert-butyl).

The hydrocarbon group that may be substituted, represented by $R^f$, is exemplified by hydrocarbon groups having 1 to 13 carbon atoms, including linear or branched alkyl groups having 1 to 6 carbon atoms (e.g., methyl, ethyl, propyl, isopropyl, butyl, isobutyl, sec-butyl, pentyl, isopentyl, hexyl); alkenyl groups having 2 to 6 carbon atoms (e.g., vinyl, allyl, 2-butenyl, methylallyl, 3-buten-yl, 2-pentenyl, 4-pentenyl, 5-hexenyl); alkynyl groups having 2 to 6 carbon atoms (e.g., ethynyl, propargyl, 2-butyn-1-yl, 3-butyn-2-yl, 1-pentyn-3-yl, 3-pentyn-1-yl, 4-pentyn-2-yl, 3-hexyn-1-yl); cycloalkyl groups having 3 to 6 carbon atoms (e.g., cyclopropyl, cyclobutyl, cyclopentyl, cyclohexyl); cycloalkenyl groups having 3 to 6 carbon atoms (e.g., cyclobutenyl, cyclopentenyl, cyclohexenyl, cyclohexadienyl); aralkyl groups having 7 to 13 carbon atoms (e.g., phenyl-$C_{1-6}$ alkyl groups such as benzyl, 1-phenethyl and 2-phenethyl, naphthyl-$C_{1-3}$ alkyl groups); and aryl groups having 6 to 10 carbon atoms (e.g., phenyl, naphthyl). Of these groups, linear or branched alkyl groups having 1 to 6 carbon atoms (e.g., methyl, ethyl, propyl, isopropyl, butyl, isobutyl, sec-butyl, pentyl, isopentyl, hexyl) are preferred, and linear or branched alkyl groups having 1 to 4 carbon atoms are more preferable.

The substituent in the substituted hydrocarbon group is exemplified by $C_{6-10}$ aryl groups (e.g., phenyl, naphthyl), amino groups, $C_{1-6}$ alkylamino groups (e.g., methylamino, ethylamino, isopropylamino), di-$C_{1-6}$ alkylamino groups (e.g., dimethylamino, diethylamino), N-$C_{7-14}$ aralkyl-N-$C_{3-6}$ cycloalkylamino groups (e.g., N-($C_{6-10}$ aryl-$C_{1-4}$ alkyl)-N-$C_{3-6}$ cycloalkylamino groups such as N-benzyl-N-cyclohexylamino), N-$C_{7-14}$ aralkyl-N-$C_{1-6}$ alkylamino groups (e.g., N-($C_{6-10}$ aryl-$C_{1-4}$ alkyl)-N-$C_{1-6}$ alkylamino such as N-(1-naphthylmethyl)-N-ethylamino), azido groups, nitro groups, halogens (e.g., fluorine, chlorine, bromine, iodine), hydroxyl groups, $C_{1-4}$ alkoxy groups (e.g., methoxy, ethoxy, propoxy, butoxy), $C_{6-10}$ aryloxy groups (e.g., phenoxy, naphthyloxy), $C_{1-6}$ alkylthio groups (e.g., methylthio, ethylthio, propylthio), $C_{6-10}$ arylthio groups (e.g., phenylthio, naphthylthio), cyano groups, carbamoyl groups, carboxyl groups, $C_{1-4}$ alkoxycarbonyl groups (e.g., methoxycarbonyl, ethoxycarbonyl), $C_{7-11}$ aryloxycarbonyl groups (e.g., phenoxycarbonyl, 1-naphthyloxycarbonyl, 2-naphthyloxycarbonyl), carboxy-$C_{1-4}$ alkoxy groups (e.g., carboxymethoxy, 2-carboxyethoxy), $C_{1-6}$ alkanoyl groups (e.g., formyl, acetyl, propionyl, isopropionyl, butyryl, pentanoyl, hexanoyl), $C_{7-11}$ aroyl groups (e.g., benzoyl, 1-naphthoyl, 2-naphthoyl), $C_{6-10}$ arylsulfonyl groups (e.g., benzenesulfonyl, 1-naphthylsulfonyl, 2-naphthylsulfonyl), $C_{1-6}$ alkylsulfinyl groups (e.g., methylsulfinyl, ethylsulfinyl), $C_6$-10 arylsulfinyl groups (e.g., benzenesulfinyl, 1-naphthylsulfinyl, 2-naphthylsulfinyl), $C_{1-6}$ alkylsulfonyl groups (e.g., methylsulfonyl, ethylsulfonyl), 5- or 6-membered heterocyclic groups containing 1 to 4 hetero atoms (e.g., nitrogen, oxygen, sulfur) (e.g., 2-furyl, 2-thienyl, 4-thiazolyl, 4-imidazolyl, 4-pyridyl, 1,3,4-thiadiazol-2-yl, 1-methyl-5-tetrazolyl), 5- or 6-membered heterocyclic-carbonyl groups containing 1 to 4 hetero atoms (e.g., nitrogen, oxygen, sulfur) (e.g., 2-furoyl, 2-thenoyl, nicotinoyl, isonicotinoyl), and 5- or 6-membered heterocyclic-thio groups containing 1 to 4 hetero atoms (e.g., nitrogen, oxygen, sulfur) (e.g., 4-pyridylthio, 2-pyrimidylthio, 1,3,4-thiadiazol-2-ylthio, 1-methyl-5-tetrazolylthio). The heterocyclic-thio group may be fused with the benzene ring to form a bicyclic fused ring-thio group (e.g., 2-benzothiazolylthio, 8-quinolylthio). Of these substituents, halogens (e.g., fluorine, chlorine, bromine, iodine), hydroxyl groups and $C_{1-4}$ alkoxy groups (e.g., methoxy, ethoxy, propoxy, butoxy) are preferred.

The number of such substituents is 1 to 5, preferably 1 to 3.

$R^d$ is preferably an alkoxy group that may be substituted or an alkoxyalkoxy group that may be substituted. Said alkoxy group that may be substituted is exemplified by alkoxy groups having 1 to 8 carbon atoms (e.g., methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy); each of the alkoxy groups in said alkoxyalkoxy group that may be substituted is exemplified by alkoxy groups having 1 to 4 carbon atoms (e.g., methoxy, ethoxy, n-propoxy, isopropoxy, n-butoxy, isobutoxy, sec-butoxy, tert-butoxy). $R_d$ is particularly preferably an alkoxy group having 1 to 8 carbon atoms, preferably 1 to 4 carbon atoms, which may be halogenated by 1 to 9 halogens, or an alkoxyalkoxy group which may be halogenated by 1 to 5 halogen atoms. Preferable alkoxy groups which may be halogenated include 2,2,2-trifluoroethoxy, 2,2,3,3,3-pentafluoropropoxy, 1-(trifluoromethyl)-2,2,2-trifluoroethoxy, 2,2,3,3-tetrafluoropropoxy, 2,2,3,3,4,4,4-heptafluorobutoxy, 2,2,3,3,4,4,5,5-octafluoropentoxy and methoxy. Preferable alkoxyalkoxy groups which may be halogenated include 3-methoxypropoxy.

q is preferably 1.

More specifically, the above-described benzimidazole compound is exemplified by a compound represented by the general formula (β):

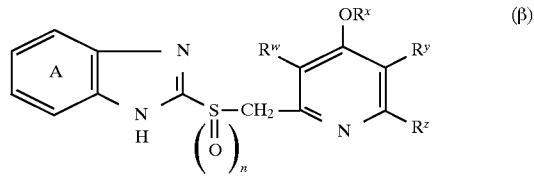

wherein ring A may be substituted; $R^W$, $R^Y$ and $R^Z$, whether identical or not, represent a hydrogen atom, an alkyl group or an alkoxy group; Rx represents a hydrocarbon group that may have substituents; and n represents 0 or 1.

With respect to the general formula (β) above, ring A is exemplified by the same rings as those mentioned as to ring A in the general formula (α) above.

The alkyl group represented by $R^W$, $R^Y$ or $R^Z$ is exemplified by linear or branched alkyl groups having 1 to 10 carbon atoms. Such alkyl groups include methyl, ethyl, n-propyl, isopropyl, n-butyl, isobutyl, sec-butyl, tert-butyl, n-pentyl, isopentyl, neopentyl, hexyl, heptyl, octyl, nonyl, and decyl. Of these alkyl groups, linear or branched alkyl groups having 1 to 6 carbon atoms are preferred, and those having 1 to 3 carbon atomsare more preferred.

The alkoxy group represented by $R^W$, $R^Y$ or $R^Z$ is exemplified by alkoxy groups having 1 to 10 carbon atoms. Such alkoxy groups include methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, cyclobutoxy, cyclopentoxy, and cyclohexyloxy. Of these alkoxy groups, alkoxy groups having 1 to 6 carbon atoms are preferred, and alkoxy groups having 1 to 3 carbon atoms are more preferred.

The hydrocarbon group that may be substituted, represented by $R^X$, is exemplified by the same groups mentioned as to the hydrocarbon group represented by $R^f$ above.

$R^W$ is preferably an alkyl group having 1 to 6 carbon atoms or an alkoxy group having 1 to 6 carbon atoms, and more preferably an alkyl group having 1 to 3 carbon atoms.

$R^Y$ is preferably a hydrogen atom or an alkyl group having 1 to 6 carbon atoms, more preferably a hydrogen atom.

$R^X$ is preferably an alkyl group having 1 to 6 carbon atoms, that may be substituted by 1) 1 to 5 halogens, 2) a hydroxyl, or 3) an alkoxy group having 1 to 4 carbon atoms, more preferably an alkyl group having 1 to 3 carbon atoms, that may be substituted by 1) 1 to 5 halogens or 2) an alkoxy group having 1 to 4 carbon atoms, $R^Z$ is preferably a hydrogen atom.

Examples of the above-described benzimidazole compound include 2-[2-[3-methyl-4-(2,2,3,3-tetrafluoropropoxy)pyridyl] methylthio]benzimidazole, 2-[2-[3-methyl-4-(2,2,2-trifluoroethoxy)pyridyl] methylsulfinyl]benzimidazole (lansoprazole), 2-[(2-pyridyl) methylsulfinyl]benzimidazole (timoprazole), 2-[2-(3,5-dimethyl-4-methoxypyridyl)methylsulfinyl]-5-methoxy-1H-benzimidazole (omeprazole), 2-[2-[4-(3-methoxypropoxy)-3-methylpyridyl]methylsulfinyl]-1H-benzimidazole sodium salt and 2-[2-(3,4-dimethoxy) pyridyl]methylsulfinyll-5-difluoromethoxy-1H-benzimidazole (panthoprazole).

The above-described benzimidazole compounds or their salts can be produced by, for example, the above-mentioned known methods described in Japanese and European Patent Publications, or similar methods thereto.

Preferably, the salt of a benzimidazole compound is used as a pharmaceutically acceptable salt. Useful pharmaceutically acceptable salts include salts with inorganic bases, salts with organic bases and salts with basic amino acids. Useful inorganic bases include alkali metals (e.g., sodium, potassium); alkaline earth metals (e.g., calcium, magnesium). Useful organic bases include trimethylamine, triethylamine, pyridine, picoline, N,N-dibenzylethylenediamine, ethanolamine, diethanolamine, trishydroxymethylaminomethane and dicyclohexylamine. Useful basic amino acids include arginine and lysine.

These salts are produced by per se known methods, e.g., those described in Japanese Patent Unexamined Publication Nos. 79177/1989 and 167587/1984, or similar methods thereto.

Such histamine $H_2$ blockers as the acid secretion inhibitors include 2-cyano-1-methyl-3-[2-[[(5-methylimidazol-4-yl)methyl]thio]ethyl]guanidine (cimetidine), N-[2-[[5-[(dimethylamino)methyl]furfuryl]-thio]ethyl]-N'-methyl-2-nitro-1,1-ethenediamine (ranitidine) and (±)-2-(furfurylsulfinyl)-N-[4-[4-(piperidinylmethyl)-2-pyridyl]oxy-(z)-2-butenyl]acetamide (loctidine).

As stated above, the present invention also relates to a pharmaceutical against Helicobacter bacteria characterized by combined use with antacids, acid secretion inhibitors etc. to prevent decomposition of its active ingredient, i.e., the compound represented by the general formula (I) or its salt, under acidic conditions such as the intragastric environment.

The above-mentioned pharmaceutical against Helicobacter bacteria, characterized by combined use of the compound represented by the general formula (I) or its salt with an antacid or acid secretion inhibitor, is not limited to limitation as to form of use, as long as it comprises a combination of the compound represented by the general formula (I) or its salt with an antacid or acid secretion inhibitor. For example, (A) the compound represented by the general formula (I) or its salt and (B) an antacid or acid secretion inhibitor may be separately formulated in the respective ordinary dosage forms, or may be a composition prepared by combining both in advance.

For example, the pharmaceutical against Helicobacter bacteria of the present invention may be produced as a single preparation prepared by mixing the compound represented by the general formula (I) or its salt with an antacid or acid secretion inhibitor by a known manufacturing method of pharmaceutical using a pharmaceutically acceptable diluent, excipient etc. when desired, or as separate preparations prepared from the respective components using a pharmaceutically acceptable diluent, excipient etc. when desired, or as a combination preparation (set, kit, pack) by packing the separately prepared preparations into the same container. For example, the pharmaceutical against Helicobacter bacteria of the present invention is used as (1) a combination preparation in which a pharmaceutical containing the compound represented by the general formula (I) or its salt and a pharmaceutical containing an antacid or an acid secretion inhibitor are packed, or (2) a composition containing the compound represented by the general formula (I) or its salt and an antacid or acid secretion inhibitor.

The pharmaceutical against Helicobacter bacteria of the present invention may also be a combination preparation or composition consisting of the compound represented by the general formula (I) or its salt and an antacid or acid secretion inhibitor.

Regarding the route of administration of the pharmaceutical against Helicobacter bacteria of the present invention, both oral and non-oral administrations (e.g., intravenous administration, subcutaneous administration, intramuscular administration) are applicable, in the same way as the above-described anti-Helicobacter agent. Specifically, the route is determined in consideration of the site of target ulcer etc.

When the compound represented by the general formula (I) or its salt and an antacid or acid secretion inhibitor are prepared as separate preparations, they may be administered to the same subject simultaneously or at a time interval via the same route or different routes.

In administering the pharmaceutical against Helicobacter bacteria of the present invention, the compound represented by the general formula (I) or its salt and an antacid or acid secretion inhibitor can be administered in dosage forms prepared by conventional methods in the same manner as the above-described anti-Helicobacter agent. For example, tablets and capsules are prepared using pharmaceutically acceptable carriers (e.g., lactose, corn starch, light silicic anhydride, microcrystalline cellulose, sucrose), binders (e.g., alpha starch, methylcellulose, carboxymethylcellulose, hydroxypropylcellulose, hydroxypropyl methylcellulose, polyvinylpyrrolidone), disintegrating agents (e.g., carboxymethylcellulose, starch, low-substituted hydroxypropylcellulose), surfactants [e.g., Tween 80 (Kao-Atlas), Pluronic F68 (Asahi Denka, Japan), polyoxy-ethylene-polyoxypropylene copolymer], antioxidants (e.g., L-cysteine, sodium sulfite, sodium ascorbate), lubricants (e.g., magnesium stearate, talc) and substances similar thereto. A solution for injection is produced by a conventional method using an aqueous solvent (e.g., distilled water, physiological saline, Ringer's solution) or an oily solvent (e.g., sesame oil, olive oil). One or more additives can be used if necessary. Such additives include solubilizers (e.g., sodium salicylate, sodium acetate), buffers (e.g., sodium citrate, glycerol), isotonizing agents (e.g., glucose, invert sugar), stabilizers (e.g., human serum albumin, polyethylene glycol), antiseptics (e.g., benzyl alcohol, phenol) and analgesics (e.g., benzalkonium chloride, procaine hydrochloride). A solid preparation for injection can be produced by a conventional method using diluents (e.g., distilled water, physiological saline, glucose), activators (e.g., carboxymethylcellulose, sodium alginate), antiseptics (e.g., benzyl alcohol, phenol) and analgesics (e.g.,-benzalkonium chloride, procaine hydrochloride).

In the case of an acid secretion inhibitor, the same methods as those described above are generally applicable, but it is preferable that the inhibitor be administered as granules with core coated with a dusting powder consisting of the inhibitor and low-substituted hydroxypropylcellulose by the method described in Japanese Patent Unexamined Publication No. 301816/1988, or a solid composition stabilized by the method described in Japanese Patent Unexamined Publication No. 163018/1991, i.e., by using a stabilizer consisting of a basic inorganic salt of magnesium and/or calcium.

Compositions for oral administration of the pharmaceutical against Helicobacter bacteria of the present invention include tablets, pills, granules, powders, capsules, syrups, emulsions and suspensions, in the same manner as the above-described anti-Helicobacter agent. Such compositions are produced by per se known methods, and lactose, starch, sucrose, magnesium stearate etc. are used as carriers or excipients.

Compositions for non-oral administration can be prepared as suppositories, externally applied preparations etc.

Examples of suppositories include rectal suppositories and vaginal suppositories, and examples of externally applied preparations include ointments (including creams), vaginal preparations, nasal preparations and transdermal preparations.

For example, suppositories can be obtained by preparing the composition of the present invention as oily or aqueous solid, semisolid or liquid suppositories.

The contents of the compound represented by the general formula (I) or its salt and an antacid or acid secretion inhibitor in the pharmaceutical against Helicobacter bacteria of the present invention may be chosen as appropriate depending upon formulation, but the content of the compound represented by the general formula (I) or its salt, for example, is about 1 to 20% by weight, preferably about 2 to 10% by weight. The antacid content is about 20 to 90% by weight, preferably about 30 to 80% by weight, and more preferably about 50 to 70% by weight, and the acid secretion inhibitor content is about 0.3 to 15% by weight, preferably about 1 to 10% by weight, and more preferably about 2 to 5% by weight.

The content ratio of the compound represented by the general formula (I) or its salt used, relative to the antacid and acid secretion inhibitor, varies among individual combinations. For example, when the compound represented by the general formula (I) or its salt is combined with an antacid, its content ratio is about 0.01 to 0.5 times (weight ratio), preferably about 0.1 to 0.3 times (weight ratio), that of the antacid; when the compound represented by the general formula (I) or its salt is combined with an acid secretion inhibitor, its content ratio is about 3 to 70 times (weight ratio), preferably about 7 to 30 times (weight ratio), that of the acid secretion inhibitor.

In the pharmaceutical against Helicobacter bacteria of the present invention, the compound represented by general formula (I) or its salt and an antacid or acid secretion inhibitor prepared as separate preparations can be administered to the same subject simultaneously. They can also administered to the same subject at a time interval. The administration frequencies of respective components may differ mutually. For example, the administration frequency of acid secretion inhibitor is preferably 1 to 2 times/day, more preferably 1 time/day, and the administration frequency of the compound represented by the general formula (I) or its salt is preferably 1 to 5 times/day, more preferably 1 to 3 times/day. The administration frequency of the antacid is preferably 1 to 5 times/day, more preferably 1 to 3 times/day.

In administering the pharmaceutical of the present invention, it is normally preferable that the compound represented by the general formula (I) or its salt be administered in a state in which acid secretion is suppressed by administration of acid secretion inhibitor (normally after 30 to 60 minutes following oral administration of acid secretion inhibitor). When acid secretion is continuously suppressed by administration of acid secretion inhibitor for consecutive days, the compound represented by the general formula (I) or its salt can be administered simultaneously with the administration of acid secretion inhibitor.

The dose of the pharmaceutical against Helicobacter bacteria of the present invention is chosen as appropriate, depending on type and symptoms of ulcer, but the compound represented by the general formula (I) or its salt is administered at about 0.1 to 10 g/day, preferably about 0.2 to 2 g/day per adult (50 kg) for oral administration, and about 0.01 to 1 g/day, preferably about 0.02 to 0.5 g/day for non-oral administration. The antacid is administered at about 1 to 30 g/day, preferably about 2 to 5 g/day per adult (50 kg) for oral administration, and the acid secretion inhibitor is administered at about 10 to 200 mg/day, preferably about 30 to 60 mg/day per adult (50 kg) for oral administration, and about 10 to 200 mg/day, preferably about 30 to 60 mg/day for non-oral administration. The dose per administration of each component is determined in consideration of such daily doses, dosage forms etc.

As stated above, the anti-Helicobacter agent and pharmaceutical against Helicobacter bacteria of the present invention are effective in the prevention or treatment of various digestive tract diseases (e.g., gastritis, duodenal ulcer, gastric ulcer, chronic gastritis) caused by bacteria showing toxic action in the digestive tract, particularly *Helicobacter pylori*.

The anti-Helicobacter agent and pharmaceutical against Helicobacter bacteria of the present invention are applicable to the prevention or treatment of ulcers in animals (e.g., mammals such as humans, dogs and cats) and particularly effective in the prevention or treatment of digestive ulcers in mammals, including humans. Such digestive ulcers include gastric ulcer, duodenal ulcer, reflux esophagitis, stomal ulcer and acute and chronic gastritis.

The anti-Helicobacter agent and pharmaceutical against Helicobacter bacteria of the present invention may further contain mucosa-protecting antiulcer drugs etc.

Such mucosa-protecting antiulcer drugs include (z)-7-[(1R,2R,3R)-2-[(E)-(3R)-3-hydroxy-4,4-dimethyl-1-octenyl]-3-methyl-5-oxocyclopentyl]-5-heptenoic acid (trimoprostil, ulstar), 1-butyric acid-7-(L-2-aminobutyric acid)-26-L-aspartic acid-27-L-valine-29-L-alanine calcitonin (Elcatonin) and 3-ethyl-7-isopropyl-1-azurenesulfonate sodium (egualen sodium).

DETAILED DESCRIPTION OF PREFFERED EMBODIMENT

The present invention is hereinafter described in more detail by means of, but not limited to, the following Reference Examples, Examples, Experimental Examples and Preparation Examples. In the description below, "room temperature" means about 15° to 30° C.

Reference Example 1

N-(Diaminophosphinyl)-4-fluorobenzamide (Flurofamide)

4-Fluorobenzamide (5 g) was suspended in chloroform (55 ml), and phosphorus pentachloride (7.5 g) was portionwise added. The mixture was heated under reflux for 2 hours, and cooled to room temperature, and then formic acid (1.7 g) was dropwise added. The resulting mixture was stirred at room temperature for 20 hours, and then ammonia gas was introduced into the mixture for 1 hour under ice-cooling. After the introduction, the mixture was stirred at room temperature. The precipitate was collected by filtration, washed with water and dried. The resulting solid was recrystallized from water to give N-(diaminophosphinyl)-4-fluorobenzamide (0.46 g) as colorless crystals.

mp 255°–257° C.

Elemental Analysis for $C_7H_9N_3O_2FP$

Calcd: C, 38.72; H, 4.18; N, 19.35. Found: C, 38.65; H, 4.08; N, 19.31.

Reference Example 2

N-(Diaminophosphinyl)-3-pyridinecarboxamide

3-Pyridinecarboxamide (5 g) was suspended in chloroform (55 ml), and phosphorus pentachloride (8.5 g) was added portionwise. The mixture was heated under reflux for 2 hours, and cooled to room temperature, and then formic acid (1.9 g) was added dropwise. The resulting mixture was stirred at room temperature for 20 hours, and then ammonia gas was introduced into the mixture for 1 hour. After the introduction, the mixture was stirred at room temperature for 1 hour. The precipitate was collected by filtration, washed with water and dried. The resulting solid was recrystallized from water to give N-(diaminophosphinyl)-3-pyridinecarboxamide (0.46 g) as colorless crystals.
mp 280°–283° C.
Elemental Analysis for $C_6H_9N_4O_2P$
Calcd: C, 36.01; H, 4.53; N, 27.99. Found: C, 35.71; H, 4.55; N, 27.91.

Reference Example 3

N-(Diaminophosphinyl)-4-nitrobenzamide

4-Nitrobenzamide (25.4 g) was suspended in carbon tetrachloride (150 ml), and phosphorus pentachloride (32.9 g) was added portionwise at 40° to 50° C. The mixture was stirred at 65° to 70° C. for about 50 minutes, and cooled to room temperature, and then formic acid (7 g) was added dropwise. The mixture was stirred at room temperature for 4 hours, and precipitated crystals were collected by filtration. The crystals were washed with carbon tetrachloride, and dried to give 40 g of crystals. The crystals (14.2 g) was suspended in chloroform (150 ml), and ammonia gas were introduced under ice-cooling for 30 minutes. After the introduction, the mixture was stirred at room temperature for 1.5 hour, and the precipitate was collected by filtration, washed with water and recrystallized from water to give N-(diaminophosphinyl)-4-nitrobenzamide (7 g) as colorless crystals.
mp 279°–285° C. (decomp.).
Elemental Analysis for $C_7H_9N_4O_4P$
Calcd: C, 34.44; H, 3.72; N, 22.95. Found: C, 34.33; H, 3.81; N, 22.63.

Reference Example 4

N-(Diaminophosphinyl)cinnamamide

Cinnamamide (10 g) was suspended in toluene (50 ml), and phosphorus pentachloride (15.6 g) was added portionwise. The mixture was stirred at 70° C for 25 minutes, and cooled to room temperature and then formic acid (3.1 g) was added dropwise. The resulting mixture was stirred at room temperature for 2 hours, and precipitated crystals were collected by filtration. The crystals were washed with toluene and dried to give 4.8 g of crystals. The crystals were dissolved in tetrahydrofuran (150 ml), and ammonia gas was introduced under ice-cooling for 30 minutes. After the introduction, the mixture was stirred at room temperature for 1 hour. The precipitate was collected by filtration, washed with water and dried. The resulting solid was recrystallized from methanol to give N-(diaminophosphinyl)cinnamamide (0.8 g) as colorless crystals.
mp 176°–178° C.
Elemental Analysis for $C_9H_{12}N_3O_2P$
Calcd: C, 48.00; H, 5.37; N, 18.66. Found: C, 47.94; H, 5.31; N, 18.62.

Reference Example 5 to 36

In the same manner as Reference Example 4, the following compounds were synthesized.

| Reference Example | Compound | mp (°C.) |
|---|---|---|
| 5 | N-(Diaminophosphinyl)-4-methylbenzenesulfonamide | 187–189 |
| 6 | N-(Diaminophosphinyl)-phenylacetamide | 255–257 |
| 7 | N-(Diaminophosphinyl)-4-chlorobenzamide | 185–189 |
| 8 | N-(Diaminophosphinyl)-3-fluorobenzamide | 260–265 |
| 9 | N-(Diaminophosphinyl)-2,6-difluorobenzamide | 279–296 |
| 10 | N-(Diaminophosphinyl)-2,4-difluorobenzamide | 167–169 |
| 11 | N-(Diaminophosphinyl)-4-chlorobenzenesulfonamide | 167–169 |
| 12 | N-(diaminophosphinyl)-4-methoxybenzamide | 290–295 |
| 13 | N-(Diaminophosphinyl)-benzenesulfonamide | 161–163 |
| 14 | N-(Diaminophosphinyl)-4-fluorobenzenesulfonamide | 164–166 |
| 15 | N-(Diaminophosphinyl)-4-methylbenzamide | 245–250 |
| 16 | N-(Diaminophosphinyl)-2-fluorobenzamide | 264–267 |
| 17 | N-(Diaminophosphinyl)-4-cyanobenzamide | 264–269 |
| 18 | N-(Diaminophosphinyl)-2-nitrobenzamide | 287–296 |
| 19 | N-(Diaminophosphinyl)-4-trifluoromethylbenzamide | 185–190 |
| 20 | N-(Diaminophosphinyl)-4-fluorocinnamamide | 288–290 |
| 21 | N-(Diaminophosphinyl)-3,5-difluorobenzamide | 217–218 |
| 22 | N-(Diaminophosphinyl)-4-bromobenzamide | 200 (decomp.) |
| 23 | N-(Diaminophosphinyl)-3-nitrobenzamide | 168–171 |
| 24 | N-(Diaminophosphinyl)-2-trifluoromethylbenzamide | 183–187 |
| 25 | N-(Diaminophosphinyl)-2-furancarboxamide | 171–173 |
| 26 | N-(Diaminophosphinyl)-1-naphthalenecarboxamide | 201–213 |
| 27 | N-(Diaminophosphinyl)-3-chlorobenzamide | 178–181 |
| 28 | N-(Diaminophosphinyl)-2-naphthalenecarboxamide | 202–208 |
| 29 | N-(Diaminophosphinyl)-3-furancarboxamide | 285–295 |
| 30 | N-(Diaminophosphinyl)-5-nitro-2-furancarboxamide | 176–178 |
| 31 | N-(Diaminophosphinyl)-4-chlorocinnamamide | 183–194 |
| 32 | N-(Diaminophosphinyl)-4-cyanocinnamamide | 182–186 |
| 33 | N-(Diaminophosphinyl)-2-nitrocinnamamide | 169–173 |
| 34 | N-(Diaminophosphinyl)-2,4-difluorocinnamamide | 174–179 |
| 35 | N-(Diaminophosphinyl)-3-fluorocinnamamide | 162–166 |
| 36 | N-(Diaminophosphinyl)-3,4-dichlorocinnamamide | 159–163 |

Reference Example 37

N-(Diaminophosphinyl)-3-phenylpropionamide

N-(Diaminophosphinyl)cinnamamide (1 g) was dissolved in methanol (200 ml), and 10% Pd—C (wet) (0.4 g) was added. The mixture was hydrogenated at room temperature under atmospheric pressure for 30 minutes, and the catalyst was removed by filtration and the filtrate was concentrated under reduced pressure. The precipitated crystals were collected by filtration, washed with diethyl ether and recrystallized from methanol to give the desired compound.
mp>300° C.
Elemental Analysis for $C_9H_{14}N_3O_2P$
Calcd: C, 47.58; H, 6.21; N, 18.49. Found: C, 47.39; HR, 6.14; N, 18.28.

Reference Example 38 to 44

In the same manner as Reference Example 37, the following compounds were synthesized.

| Reference Example | Compound | mp (°C.) |
|---|---|---|
| 38 | N-(Diaminophosphinyl)-3-(4-fluorophenyl)propionamide | 160–162 |
| 39 | N-(Diaminophosphinyl)-3-(4-chlorophenyl)propionamide | 151–157 |
| 40 | N-(Diaminophosphinyl)-3-(4-cyanophenyl)propionamide | 162–165 |
| 41 | N-(Diaminophosphinyl)-3-(2,4-difluorophenyl)propionamide | 170–175 |
| 42 | N-(Diaminophosphinyl)-3-(3-fluorophenyl) propionamide | 149–153 |
| 43 | N-(Diaminophosphinyl)-3-(2-aminophenyl) propionamide | 183–187 |
| 44 | N-(Diaminophosphinyl)-4-aminophenoxyacetamide | 158–165 |

Reference Example 45

4-Nitrophenoxyacetamide

A mixture of 4-nitrophenol (7.5 g), iodoacetamide (10 g), potassium carbonate (7.5 g) and dimethylformamide (50 ml) was stirred at 50° C. for 15 hours. The mixture was poured into ice-water, and extracted with ethyl acetate. The extract was washed with water and saturated aqueous sodium chloride, and dried over anhydrous magnesium sulfate, and then concentrated under reduced pressure. The residue was recrystallized from acetone-diisopropyl ether to give the desired compound (7.9 g) as colorless crystals.
m.p. 160°–161° C.

Reference Examples 46 to 59

In the same manner as Reference Example 45, the following compounds were synthesized.

| Reference Example | Compound | mp (°C.) |
|---|---|---|
| 46 | 4-Methoxyphenoxyacetamide | 116–117 |
| 47 | 4-Fluorophenoxyacetamide | 111–112 |
| 48 | 4-Chlorophenoxyacetamide | 142–143 |
| 49 | 2,3,5-Trimethylphenoxyacetamide | 138–139 |
| 50 | 4-Cyanophenoxyacetamide | 154–156 |
| 51 | 3-Chlorophenoxyacetamide | 128–129 |
| 52 | 2-Chlorophenoxyacetamide | 153–155 |
| 53 | 3-Fluorophenoxyacetamide | 112–113 |
| 54 | Phenylthioacetamide | 112–113 |
| 55 | 4-Fluorophenylthioacetamide | 122–123 |
| 56 | 2-Benzoxazolylthioacetamide | 162–164 |
| 57 | 2 Benzothiazolylthioacetamide | 144–147 |
| 58 | 5-Chloro-2-benzothiazolylthioacetamide | 180–183 |
| 59 | 5-Ethoxy-2-benzothiazolylthioacetamide | 132–137 |

Reference Example 60

2-Benzofurancarboxamide

2-Benzofurancarboxylic acid (6.0 g) was dissolved in tetrahydrofuran (50 ml), and N,N-dimethylformamide (3 drops) was added. Oxalyl chloride (4.0 g) was added dropwise at room temperature, and the mixture was stirred for 30 minutes. The reaction mixture was concentrated under reduced pressure, and the residue was dissolved in ethyl acetate (20 ml). The resulting solution was added dropwise to a mixture of 25% aqueous ammonia (30 ml) and ethyl acetate (100 ml) with stirring under ice-cooling. The resulting mixture was stirred at room temperature for 3 hours, and then the organic layer was collected. The organic layer was washed with water and saturated aqueous sodium chloride solution, and dried over anhydrous magnesium sulfate, and then concentrated under reduced pressure. The precipitated crystals were collected by filtration and washed with isopropyl ether to give 2- benzofurancarboxamide (4.5 g).
mp 165°–166° C.

Reference Examples 61–119

In the same manner as Reference Example 60, the following compounds were synthesized.

| Reference Example | Compound | mp (°C.) |
|---|---|---|
| 61 | 2-Methyl-5-benzoxazolecarboxamide | 236–238 |
| 62 | 3-(Chloro-2-benzoxazolyl)propenamide | 230 (decomp.) |
| 63 | 5-Methyl-3-phenyl-4-isoxazolecarboxamide | 215–216 |
| 64 | 3-(4-Bromo-2-thienyl)propenamide | 187–188 |
| 65 | 3-(2-Thienyl)propenamide | 158–159 |
| 66 | 2-Cyano-3-(2-thienyl)propenamide | 159–163 |
| 67 | 2-Thienylacetamide | 150–152 |
| 68 | 3-Thienylacetamide | 155–157 |
| 69 | 2-Thiophenecarboxamide | 181–183 |
| 70 | 3-Thiophenecarboxamide | 186–189 |
| 71 | 5-Chloro-2-thiophenecarboxamide | 102–104 |
| 72 | 5-Bromno-2-thiophenecarboxamide | 112–113 |
| 73 | 5-Methyl-2-thiophenecarboxamide | 125–128 |
| 74 | 4,5-Dibromo-2-thiophenecarboxamide | 172–175 |
| 75 | 4-Bromo-2-thiophenecarboxamide | 153–157 |
| 76 | 3-Methyl-2-thiophenecarboxamide | 124–127 |
| 77 | 5-Ethyl-2-thiophenecarboxamide | 145–147 |
| 78 | 5-Nitro-2-thiophenecarboxamide | 191–192 |
| 79 | 5-Bromo-3-thiophenecarboxamide | 100–101 |
| 80 | 5-Cyano-2-thiophenecarboxamide | 222–223[1] |
| 81 | 5-Difluoromethyl-2-thiophenecarboxamide | 137–138 |
| 82 | 3-Chloro-2-thiophenecarboxamide | 102–104 |
| 83 | 2-Methyl-3-thiophenecarboxamide | 137–138 |
| 84 | 3-Bromo-2-thiophenecarboxamide | 112–113 |
| 85 | 5-Acetyl-2-thiophenecarboxamide | 233–236 (decomp.) |
| 86 | 5-Methanesulfonyl-2-thiophenecarboxamide | 165–169 |
| 87 | 3-Difluoromethyl-2-thiophenecarboxamide | 143–144 |
| 88 | 2-Difluoromethyl-3-thiophenecarboxamide | 119–120 |
| 89 | 5-Nitro-3-thiophenecarboxamide | 163–165 |
| 90 | 5-Methoxy-2-thiophenecarboxamide | 158–160 |
| 91 | 3-Cyano-2-thiophenecarboxamide | 174–176 |
| 92 | 4-Methoxy-2-thiophenecarboxamide | 163–165 |
| 93 | 2,5-Dichloro-3-thiophenecarboxamide | 98–1OO |
| 94 | 2-Bromo-3-thiophenecarboxamide | 141–142 |
| 95 | 3-Ethyl-2-thiophenecarboxamide | 146–149 |
| 96 | 4-Methyl-2-thiophenecarboxamide | 109–114 |
| 97 | 5-Bromo-4-methyl-2-thiophenecarboxamide | 162–164 |
| 98 | 5-Chloro-3-thiophenecarboxamide | 138–139[2] |
| 99 | 5-Difluoromethyl-3-thiophenecarboxamide | 83–84 |
| 100 | 2,5-Dimethyl-3-thiophenecarboxamide | 137–138 |
| 101 | 5-Chloro-2-methyl-3-thiophenecarboxamide | 125–127[3] |
| 102 | 4-Chloro-5-methyl-3-thiophenecarboxamide | 136–137 |
| 103 | 5-Chloro-4-methyl-3-thiophenecarboxamide | 144–145 |
| 104 | 4,5-Dichloro-2-thiophenecarboxamide | 163–164 |
| 105 | 4-Bromo-3-thiophenecarboxamide | 151–153 |
| 106 | 2-Chloro-3-thiophenecarboxamide | 131–132 |
| 107 | 5-Bromo-2-furancarboxamide | 149–150 |
| 108 | 5-Chloro-2-furancarboxamide | 160–161 |
| 109 | 5-Bromo-3-furancarboxamide | 174–176 |
| 110 | 5-Methyl-2-furancarboxamide | 135–136 |

-continued

| Reference Example | Compound | mp (°C.) |
|---|---|---|
| 111 | 5-Ethyl-2-furancarboxamide | 107–109 |
| 112 | 2-Methyl-3-furancarboxamide | 87–88 |
| 113 | 2-Chloro-3-furancarboxamide | 104–105 |
| 114 | 5-Chloro-3-furancarboxamide | 180–181 |
| 115 | 5-Difluoromethyl-2-furancarboxamide | 80–81 |
| 116 | 2-Trifluoromethyl-5-methyl-3-furancarboxamide | 127–128 |
| 117 | 2,5-Dimethyl-3-furancarboxamide | 128–129 |
| 118 | 5-Chloro-2-methyl-3-furancarboxamide | 132–133 |
| 119 | 2-Ethyl-3-furancarboxamide | 67–69 |

1) 5-Cyano-2-thiophenecarboxamide

The compound of Reference Example 80 was synthesized by the following method.

5-Formyl-2-thiophenecarboxylic acid (2.64 g) (synthesized in accordance with the method described in Tetrahedron, 41, 3803 (1985)) was dissolved in tetrahydrofuran (30 ml), and N,N-dimethylformamide (3 drops) was added. Oxalyl chloride (2.2 ml) was added dropwise at room temperature, and the mixture was stirred for 2 hours. The reaction mixture was concentrated under reduced pressure and the concentrate was dissolved in ethyl acetate (50 ml). The resulting solution was added dropwise to a mixture of 25% aqueous ammonia (50 ml) and ethyl acetate (200 ml) with stirring under ice-cooling. The resulting mixture was stirred at room temperature, and then the organic layer was collected. The aqueous layer was extracted twice with ethyl acetate. The organic layers were combined, dried over magnesium sulfate and concentrated under reduced pressure to give 5-formyl-2-thiophenecarboxamide (1.77 g). A mixture of 5-formyl-2- thiophenecarboxamide (1.55 g), N,O-bis(trifluoroacetyl)hydroxyamine (3.5 g), pyridine (2 ml) and toluene (110 ml) was stirred under reflux for 1 hour, and then cooled, and concentrated under reduced pressure. The residue was purified by silica gel column chromatography to give 5-cyano-2-thiophenecarboxamide (0.6 g).

mp 222°–223° C.

2) 5-Chloro-3-thiophenecarboxamide

The compound of Reference Example 98 was synthesized by the following method.

3-Thiophenecarboxyalic acid ethyl ester (1.98 g) was dissolved in acetonitrile (30 ml), and sulfuryl chloride (1.5 ml) was added under ice-cooling. The mixture was stirred at 10° C. for 30 minutes, and then 10% aqueous sodium thiosulfate (100 ml) was added. The resulting mixture was stirred at room temperature for 2 hours, and then extracted with diethyl ether. The extract was washed with saturated aqueous sodium chloride solution, dried over anhydrous magnesium sulfate, and concentrated under reduced pressure to give a mixture of 5-chloro-3-thiophenecarboxylic acid ethyl ester and 2,5-dichloro-3-thiophenecarboxylic acid ethyl ester. This mixture was dissolved in a mixture of ethanol (15 ml) and tetrahydrofuran (15 ml), and 1N aqueous sodium hydroxide (20 ml) was added. The resulting mixture was stirred at room temperature, and then washed with diethyl ether. The aqueous layer was acidified with 1N hydrochloric acid and extracted with ethyl acetate. The extract was dried over anhydrous magnesium sulfate and concentrated under reduced pressure to give a mixture of 5-chloro-3-thiophenecarboxylic acid and 2,5-dichloro-3-thiophenecarboxylic acid (1.7 g). This mixture was suspended in toluene (15 ml), and oxalyl chloride (1.56 ml) was added dropwise. Further, N,N-dimethylformamide (1 drop) was added, and the reaction mixture was stirred at room temperature for 1 hour. The reaction mixture was concentrated under reduce pressure, and the concentrate was dissolved in ethyl acetate (10 ml). The resulting solution was added dropwise to a mixture of 25% aqueous ammonia (16 ml) and ethyl acetate (70 ml) with stirring under ice-cooling. The resulting mixture was stirred at room temperature for 10 minutes, and the organic layer was collected. The aqueous layer was extracted with ethyl acetate. The organic layers were combined, dried over anhydrous magnesium sulfate and concentrated under reduced pressure. The residue was purified by silica gel column chromatography to give 5-chloro-3-thiophenecarboxamide (0.76 g).

mp 138°–139° C.

3) 5-Chloro-2-methyl-3-thiophenecarboxamide

The compound of Reference Example 101 was synthesized by the following method.

2-Methyl-3-thiophenecarboxyalic acid (5.69 g) synthesized in the same manner as Reference Example 127 was dissolved in N,N-dimethylformamide (50 ml), and iodoethane (3.2 ml) and potassium carbonate (5.52 g) were added. The reaction mixture was stirred at room temperature for 15 hours, and poured into water, and then extracted with diethyl ether. The extract was washed with 5% aqueous potassium hydrogen sulfate, dried over anhydrous magnesium sulfate, and then concentrated under reduced pressure to give a crude product of 2-methyl-3-thiophenecarboxylic acid ethyl ester. This crude product of 2-methyl-3-thiophenecarboxylic acid ethyl ester was dissolved in acetonitrile (50 ml), and sulfuryl chloride (3.0 ml) in acetonitrile (20 ml) was added dropwise. The mixture was stirred for 1 hour under cooling over a water bath, and then 10% aqueous sodium thiosulfate (100 ml) was added. The mixture was stirred at room temperature for 2 hours, and extracted with diethyl ether. The extract was washed with saturated aqueous sodium chloride, dried over anhydrous magnesium sulfate, and concentrated under reduced pressure to give a crude product of 5-chloro-2-methyl-3-thiophenecarboxylic acid ethyl ester. This crude product was dissolved in a mixture of ethanol (25 ml) and tetrahydrofuran (25 ml), and 1N aqueous sodium hydroxide (50 ml) was added. The resulting mixture was stirred at 65° C. for 2 hours, and then washed with diethyl ether. The aqueous layer was acidified with 1N hydrochloric acid and extracted with ethyl acetate. The extract was dried over anhydrous magnesium sulfate and concentrated under reduced pressure to give a crude product of 5-chloro-2-methyl-3-thiophenecarboxylic acid. This crude product of 5-chloro-2-methyl-3-thiophenecarboxylic acid was suspended in toluene (50 ml), and oxalyl chloride (4.6 ml) was added dropwise. Further, N,N-dimethylformamide (3 drops) was added, and the reaction mixture was stirred at room temperature for 1 hours. The mixture was concentrated under reduced pressure, and the concentrate was dissolved in ethyl acetate (20 ml). The resulting solution was added dropwise to a mixture of 25% aqueous ammonia (56 ml) and ethyl acetate (150 ml) with stirring under ice-cooling. The mixture was stirred at room temperature for 10 minutes, and then the organic layer was collected. The aqueous layer was extracted with ethyl acetate. The organic layers were combined, dried over anhydrous magnesium sulfate and concentrated under reduced pressure. The residue was purified by silica gel column chromatography to give 5-chloro-2-methyl-3-thiophenecarboxamide (1.6 g)

mp 125°–127° C.

Reference Example 120

4,5-Dibromo-2-thiophenecarboxylic Acid

2-Thiophenecarboxylic acid (3.84 g) was added to bromine (9.3 ml), and the mixture was stirred at room temperature for 15 hours. An excess amount of bromine was neutralized with aqueous ammonium carbonate, and then the mixture was acidified with 1N hydrochloric acid. The precipitated crystals were collected by filtration, and dissolved in 1N sodium hydroxide. The mixture was acidified with 1N hydrochloric acid, dried over anhydrous magnesium sulfate, and concentrated under reduced pressure to give 4,5-dibromo-2-thiophenecarboxylic acid (7.48 g) as crystals.
mp 225°–227° C.

Reference Example 121

4-Bromo-2-thiophenecarboxylic Acid

Silver nitrate (1.7 g) was dissolved in water (40 ml), and sodium hydroxide (0.44 g) in water (1 ml) was added. Precipitated silver oxide was collected by filtration and suspended in 10% aqueous sodium hydroxide (20 ml). The resulting suspension was heated at 60° to 65° C., and 4-bromo-2-thiophenecarbaldehyde (1.91 g) was added dropwise. The mixture was stirred for 30 minutes, and precipitates were removed by filtration. The filtrate was washed with diethyl ether, and 1N hydrochloric acid was added to the aqueous layer to adjust the pH to 4. The aqueous layer was extracted with ethyl acetate, and the extract was dried over anhydrous magnesium sulfate and concentrated under reduced pressure to give 4-bromo-2-thiophenecarboxylic acid (1.39 g) as crystals.
mp 124°–126° C.

Reference Example 122

4-Ethyl-2-thiophenecarboxylic Acid 1,3-Dimethyl-2-(2-thienyl)imidazolidine (5.46 g) (synthesized in accordance with the method described in Tetrahedron, 41, 3803 (1985)) and N,N,N',N'-tetramethylethylenediamine (4.7 ml) were dissolved in tetrahydrofuran (150 ml). The mixture was cooled to −78° C., and n-butyllithium (1.6M in hexane, 19.5 ml) was slowly added dropwise. The mixture was stirred at the same temperature for 2 hours, and iodoethane (2.4 ml) was added. The mixture was slowly heated to room temperature and then stirred for 15 hours. The reaction mixture was concentrated under reduced pressure, and 10% sulfuric acid (200 ml) was added to the residue. The mixture was stirred for 24 hours and extracted with ethyl acetate. The organic layer was washed with water, dried over anhydrous magnesium sulfate and concentrated under reduced pressure. The residue was purified by silica gel column chromatography to give 5-ethyl-2-thiophenecarbaldehyde (1.68 g) as oil. 5-ethyl-2-thiophenecarbaldehyde (1.68 g) was dissolved in acetonitrile (20 ml), and sodium dihydrogen phosphate (0.54 g) in water (10 ml) and 30% hydrogen peroxide (2.0 ml) were added. Sodium chlorite (3.0 g) in water (20 ml) was then added dropwise under ice-cooling. The mixture was stirred at room temperature for 2 hours, alkalified with 1N sodium hydroxide and washed with diethyl ether. The aqueous layer was acidified with 1N hydrochloric acid and extracted with ethyl acetate. The extract was dried over anhydrous magnesium sulfate and concentrated under reduced pressure to give 5-ethyl-2-thiophenecarboxylic acid (1.48 g) as crystals.
mp 65°–66° C.

Reference Example 123

5-Nitro-2-thiophenecarboxylic Acid

5-Nitro-2-thiophenecarbaldehyde (7.86 g) was dissolved in acetonitrile (50 ml), and sodium dihydrogen phosphate (1.6 g) in water (20 ml) and 30% aqueous hydrogen peroxide (5.9 ml) were added. Furtherl sodium chlorite (8.0 g) in water (70 ml) was added dropwise under ice-cooling. The reaction mixture was stirred at room temperature for 2 hours, and then sodium thiosulfate was added to remove an excess amount of hydrogen peroxide. The mixture was alkalified with 1N sodium hydroxide and extracted with diethyl ether. The aqueous layer was acidified with 1N hydrochloric acid and extracted with ethyl acetate. The extract was dried over anhydrous magnesium sulfate and concentrated under reduced pressure to give 5-nitro-2-thiophenecarboxylic acid (7.83 g) as crystals.
mp 158°–159° C.

Reference Example 124

5-Bromo-3-thiophenecarboxylic Acid

A mixture of 3-thiophenecarboxylic acid (12.81 g), pyridinium bromide perbromide (35.54 g) and acetic acid (50 ml) was stirred at 45° C. for 48 hours. The mixture was poured into ice-water and precipitated crystals were collected by filtration. The crystals were dissolved in ethyl acetate, dried over anhydrous magnesium sulfate and concentrated under reduced pressure to give 5-bromo-3-thiophenecarboxylic acid (19.78 g) as crystals.
mp 137°–138° C.

Reference Example 125

5-Difluoromethyl-2-thiophenecarboxylic Acid

5-Formyl-2-thiophenecarboxylic acid methyl ester (1.7 g) (synthesized in accordance with the method described in J. Heterocyclic Chem., 28, 17 (1991)) in methylene chloride (10 ml) was slowly added dropwise to diethylaminosulfur trifluoride (DAST) (1.6 g) in methylene chloride (20 ml). The mixture was stirred at room temperature for 2 hours, and then diethylaminosulfur trifluoride (DAST) (0.5 g) was further added. The resulting mixture was stirred at room temperature for 1 hour, and water (10 ml) and saturated aqueous sodium bicarbonate (10 ml) were added. The resulting mixture was allowed to stand overnight. The organic layer was collected, washed with water, dried over anhydrous magnesium sulfate and concentrated under reduced pressure. The residue was purified by silica gel column chromatography to give 5-difluoromethyl-2-thiophenecarboxylic acid methyl ester (0.81 g). 5-Difluoromethyl-2-thiophenecarboxylic acid methyl ester (2.58 g) synthesized in this manner was dissolved in methanol (50 ml), and 1N sodium hydroxide (30 ml) was added. The mixture was stirred at room temperature for 2 hours and washed with diethyl ether. The aqueous layer was acidified with 1N hydrochloric acid and extracted with diethyl ether. The extract was dried over anhydrous magnesium sulfate and concentrated under reduced pressure to give 5-difluoromethyl-2-thiophenecarboxylic acid (2.13 g) as crystals.
mp 111°–112° C.

Reference Example 126

3-Chloro-2-thiophenecarboxylic Acid

This compound was synthesized in accordance with the method described in Heterocycles, 23, 1431 (1985).

Reference Example 127

2-Methyl-3-thiophenecarboxylic Acid

3-Thiophenecarboxylic acid (3.84 g) was dissolved in tetrahydrofuran (50 ml), and the mixture was cooled to −78°

C. n-Butyllithium (1.6M in hexane, 41.3 ml) was slowly added dropwise, and the mixture was stirred at the same temperature for 30 minutes. Iodomethane (3.7 ml) in tetrahydrofuran (10 ml) was added dropwise. The resulting mixture was heated to room temperature and stirred for 15 hours. The mixture was poured into water and washed with diethyl ether. The aqueous layer was acidified with 1N hydrochloric acid, and extracted with ethyl acetate. The extract was dried over anhydrous magnesium sulfate and concentrated under reduced pressure to give 2-methyl-3-thiophenecarboxylic acid (3.98 g) as crystals.
mp 71°–73° C.

Reference Example 128

3-Bromo-2-thiophenecarboxylic Acid

3-Amino-2-thiophenecarboxylic acid methyl ester (9.4 g) was suspended in hydrobromic acid (20 ml), and the mixture was stirred at room temperature for 30 minutes. The mixture was cooled to 0° C., and sodium nitrite (4.2 g) in water (10 ml) was added dropwise below 10° C. The mixture was stirred for 1 hour, and then poured into copper (I) bromide (9.06 g) in hydrobromic acid (25 ml). The resulting mixture was stirred at 60° C. for 1 hour and extracted with diethyl ether. The extract was dried over anhydrous magnesium sulfate and concentrated under reduced pressure and distilled under reduced pressure to give 3-bromo-2-thiophenecarboxylic acid methyl ester (7.99 g) as crystals.
bp 101° C./8 mmHg, mp 47°–48° C.

3-Bromo-2-thiophenecarboxylic acid methyl ester (7.74 g) was dissolved in a mixture of methanol (35 ml) and tetrahydrofuran (35 ml), and 1N aqueous sodium hydroxide (53 ml) was added. The mixture was stirred at room temperature for 2 hours and washed with diethyl ether. The aqueous layer was acidified with 1N hydrochloric acid and extracted with ethyl acetate. The extract was dried over anhydrous magnesium sulfate and concentrated under reduced pressure to give 3-bromo-2-thiophenecarboxylic acid (7.05 g) as crystals.
mp 200°–201° C.

Reference Example 129

5-Acetyl-2-thiophenecarboxylic Acid

2-Methyl-2-(2-thienyl)-1,3-dioxolan (6.6 g) (synthesized in accordance with the method described in Tetrahedron, 41, 3803 (1985)) was dissolved in tetrahydrofuran (200 ml), and N,N,N', N'-tetramethylethylenediamine (5.87 ml) was added. The mixture was cooled to −78° C., and n-butyllithium (1.6M in hexane, 25 ml) was slowly added dropwise. The mixture was stirred at the same temperature for 2 hours, and warmed slowly to room temperature for a period of 2 hours with introducing carbon dioxide gas. The reaction mixture was concentrated under reduced pressure, and 2N hydrochloric acid (200 ml) was added. The mixture was stirred for 3 hours, and precipitated crystals were collected by filtration, washed with water and dried to give 5-acetyl-2-thiophenecarboxylic acid (3.87 g) as crystals.
mp 283° C.

Reference Example 130

5-Methanesulfonyl-2-thiophenecarboxylic Acid

5-Methylthio-2-thiophenecarbaldehyde (4.48 g) (synthesized in accordance with the method described in Tetrahydron, 41, 3803 (1985)) was dissolved in acetonitrile (20 ml), and sodium dihydrogen phosphate (1.2 g) in water (10 ml) and 30% aqueous hydrogen peroxide (3.5 ml) were added. Further sodium chlorite (3.85 g) in water (10 ml) was added dropwise under ice-cooling. The mixture was stirred at room temperature for 15 hours, and sodium sulfite (1 g) was added. The mixture was alkalified with 1N aqueous sodium hydroxide and extracted with diethyl ether. The aqueous layer was acidified with 1N hydrochloric acid and extracted with ethyl acetate. The extract was dried over anhydrous magnesium sulfate and concentrated under reduced pressure. The residue was recrystallized from ethyl acetate-diisopropyl ether to give 5-methanesulfonyl-2-thiphenecarboxylic acid (1.73 g) as crystals.
mp 190°–194° C.

Reference Example 131

3-Difluoromethyl-2-thiophenecarboxylic Acid

3-Thiophenecarbaldehyde (22.43 g) was dissolved in toluene (200 ml) and N,N'-dimethylethylenediamine (22.3 ml) was added. The mixture was stirred for 16 hours with removing azeotropic water under reflux by Dean-stark trap. The reaction mixture was concentrated under reduced pressure and the residue was distilled under reduced pressure to give 1,3-dimethyl-2-(3-thienyl)imidazolidine (5.88 g).
bp 63°–64° C./0.8 mmHg, mp 112°–113° C.

1,3-Dimethyl-2-(3-thienyl)imidazolidine (9.06 g) synthesized in this manner was dissolved in tetrahydrofuran (100 ml), and N,N,N',N'-tetramethylethylenediamine (7.85 ml) was added. The mixture was cooled to −78° C., and n-butyllithium (1.6M in hexane, 32.5 ml) was slowly added dropwise. The mixture was stirred at the same temperature for 2 hours and poured into a mixture of dry ice and diethyl ether. The resulting mixture was warmed to room temperature with stirring, and concentrated under reduced pressure. 10% Sulfuric acid (100 ml) was added to the residue, and the mixture was stirred for 15 hours and extracted with diethyl ether. The diethyl ether layer was extracted with 1N aqueous sodium hydroxide, and the aqueous layer was washed with diethyl ether, acidified with 1N hydrochloric acid and extracted with ethyl acetate. The extract was dried over anhydrous magnesium sulfate and concentrated under reduced pressure to give 3-formyl-2-thiophenecarboxyalic acid (5.92 g) as crystals.
mp 119°–120° C.

3-Formyl-2-thiophenecarboxylic acid (3.12 g) was dissolved in N,N-dimethylformamide (30 ml), and iodoethane (1.76 ml) and potassium carbonate (2.76 g) were added. The mixture was stirred at room temperature for 15 hours and poured into water. The mixture was extracted with ethyl acetate, washed with 5% aqueous potassium hydrogen sulfate, dried over anhydrous magnesium sulfate and concentrated under reduced pressure. The residue was subjected to silica gel column chromatography, and the desired fractions were concentrated under reduced pressure to give 3-formyl-2-thiophenecarboxylic acid ethyl ester (2.91 g). 3-Formyl-2-thiphenecarboxylic acid ethyl ester (1.84 g) in methylene chloride (10 ml) was slowly added dropwise to diethylaminosulfur trifluoride (DAST) (1.45 ml) in methylene chloride (10 ml) at room temperature. The mixture was stirred at room temperature for 3 hours, and saturated aqueous sodium bicarbonate was added. The organic layer was collected, dried over anhydrous magnesium sulfate and concentrated under reduced pressure. The residue was purified by silica gel column chromatography to give 3-difluoromethyl-2-thiophenecarboxylic acid ethyl ester (1.58 g). 3-Difluoromethyl-2-thiophenecarboxylic acid ethyl ester was dissolved in a mixture of ethanol (10 ml) and tetrahydrofuran (10 ml), and 1N aqueous sodium hydroxide (11 ml) was added. The mixture was stirred at room temperature for 2 hours and washed with diethyl ether. The aqueous layer was acidified with 1N hydrochloric acid and extracted with ethyl acetate. The extract was dried over anhydrous magnesium sulfate and concentrated under reduced ppressure to give 3-difluoromethyl-2-thiophenecarboxylic acid (1.12 g) as crystals.
mp 119°–120° C.

Reference Example 132

2-Difluoromethyl-3-thiphenecarboxylic Acid

3-Thiophenecarboxylic acid (3.48 g) was dissolved in tetrahydrofuran (50 ml), and N,N,N',N'-tetramethylethylenediamine (10 ml) was added. The mixture was cooled to −78° C., and n-butyllithium (1.6M in hexane, 41.3 ml) was slowly added dropwise. The mixture was stirred at the same temperature for 1 hour, and N,N-dimethylformamide (4.6 ml) was added dropwise. The mixture was warmed to room temperature and stirred for 15 hours. The reaction mixture was acidified with 1N hydrochloric acid and extracted with ethyl acetate. The extract was dried over anhydrous magnesium sulfate and concentrated under reduced pressure. The residue was purified by silica gel column chromatography to give a mixture of 2-formyl-3-thiophenecarboxylic acid and 5-formyl-3-thiophenecarboxylic acid (2.11 g). This mixture was dissolved in N,N-dimethylformamide (30 ml), and iodoethane (0.95 ml) and potassium carbonate (1.66 g) were added. The reaction mixture was stirred at room temperature for 15 hours, poured into water and extracted with diethyl ether. The extract was washed with 5% aqueous potassium hydrogen sulfate, dried over anhydrous magnesium sulfate and concentrated under reduced pressure. The residue was subjected to silica gel column chromatography, and the desired fractions were concentrated under reduced pressure to give 2-formyl-3-thiophenecarboxylic acid ethyl ester (1.75 g). 2-Formyl-3-thiophenecarboxylic acid ethyl ester (1.66 g) in methylene chloride (20 ml) was slowly added dropwise to diethylaminosulfur trifluoride (DAST) (1.32 ml) in methylene chloride (10 ml) at room temperature. The mixture was stirred at room temperature for 15 hours, and saturated aqueous sodium bicarbonate was added. The organic layer was collected, dried over anhydrous magnesium sulfate and concentrated under reduced pressure. The residue was purified by silica gel column chromatography to give 2-difluoromethyl-3-thiophenecarboxylic acid ethyl ester (1.08 g). 2-Difluoromethyl-3-thiophenecarboxylic acid ethyl ester was dissolved in a mixture of ethanol (10 ml) and tetrahydrofuran (10 ml), and 1N aqueous sodium hydroxide (7.8 ml) was added. The mixture was stirred at room temperature for 1 hour and washed with diethyl ether. The aqueous layer was acidified with 1N hydrochloric acid and extracted with ethyl acetate. The extract was dried over anhydrous magnesium sulfate and concentrated under reduced pressure to give 2-difluoromethyl-3-thiophenecarboxylic acid (0.88 g) as crystals.
mp 127°–128° C.

Reference Example 133

5-Nitro-3-thiophenecarboxylic Acid

3-Thiophenecarboxylic acid (5.12 g) was added portionwise to a mixture of nitric acid (20 ml) and sulfuric acid (11.5 ml) below 5° C. The mixture was stirred at the same temperature for 30 minutes, and poured into ice water. The mixture was alkalified with 1N sodium hydroxide and washed with diethyl ether. The aqueous layer was acidified with 1N hydrochloric acid and extracted with ethyl acetate. The extract was dried over anhydrous magnesium sulfate and concentrated under reduced pressure. The residue was recrystallized from ethyl acetate to give 5-nitro-3-thiophenecarboxylic acid (4.45 g) as crystals.
mp 117°–118° C.

Reference Example 134

5-Methoxy-2-thiophenecarboxylic Acid

2-Methoxythiophene (4.0 ml) was dissolved in tetrahydrofuran (50 ml), and the mixture was cooled to −78° C. n-Butyllithium (1.6M in hexane, 31 ml) was slowly added dropwise, and the mixture was stirred at the same temperature for 1 hour. The mixture was poured into a mixture of dry ice and diethyl ether, and warmed to room temperature with stirring. The solvent was distilled off, and the residue was acidified with 1N hydrochloric acid. The mixture was extracted with ethyl acetate. The extract was dried over anhydrous magnesium sulfate and concentrated under reduced pressure to give 5-methoxy-2-thiophenecarboxylic acid (5.62 g).
mp 167°–168° C.

Reference Example 135

3-Cyano-2-thiophenecarboxylic Acid

3-Formyl-2-thiophenecarboxylic acid (4.68 g) was dissolved in N,N-dimethylformamide (30 ml), and benzyl bromide (3.9 ml) and potassium carbonate (4.15 g) were added. The mixture was stirred at room temperature for 15 hours, poured into water, and then extracted with diethyl ether. The extract was washed with 5% potassium hydrogen sulfate, dried over anhydrous magnesium sulfate and concentrated under reduced pressure. The residue was subjected to silica gel column chromatography, and the desired fractions were concentrated under reduced pressure to give 3-formyl-2-thiophenecarboxylic acid benzyl ester (2.65 g). 3-Formyl-2-thiophenecarboxylic acid benzyl ester (2.65 g) was dissolved in ethanol (50 ml), and hydroxylamine hydrochloride (0.83 g) and pyridine (0.97 ml) were added. The mixture was stirred under reflux for 3 hours, and concentrated under reduced pressure. The residue was poured into water, and extracted with diethyl ether. The extract was dried over anhydrous magnesium sulfate and concentrated under reduced pressure to give 3-aldoxime-2-thiophenecarboxylic acid benzyl ester (2.61 g). This product was dissolved in acetic anhydride (20 ml), and the mixture was stirred at 160° C. for 10 hours. The mixture was cooled, poured into water (100 ml) and extracted with diethyl ether. The extract was washed with saturated aqueous sodium bicarbonate, dried over anhydrous magnesium sulfate and concentrated under reduced pressure. The residue was purified by silica gel column chromatography to give 3-cyano-2-thiophenecarboxylic acid benzyl ester (2.01 g). This product was dissolved in tetrahydrofuran (40 ml), and 5% Pd—C (wet) (0.25 g) was added. The mixture was hydrogenated at room temperature under atmospheric pressure for 72 hours. The catalyst was removed by filtration and the filtrate was concentrated under reduced pressure to give 3-cyano-2-thiophenecarboxylic acid (0.98 g) as crystals.
mp 204°–205° C.

Reference Example 136

4-Methoxy-2-thiophenecarboxylic Acid

3-Methoxythiophene (4.0 ml) was dissolved in tetrahydrofuran (50 ml), and the mixture was cooled to −78° C.

n-Butyllithium (1.6M in hexane, 19.5 ml) was slowly added dropwise, and the mixture was stirred at the same temperature for 1 hour. The mixture was poured into a mixture of dry ice and diethyl ether, and warmed to room temperature with stirring. The solvent was distilled off, and the residue was acidified with 1N hydrochloric acid and extracted with ethyl acetate. The extract was dried over anhydrous magnesium sulfate and concentrated under reduced pressure to give a mixture of 3-methoxy-2-thiophenecarboxylic acid and 4-methoxy-2-thiophenecarboxylic acid (6.0 g). This mixture was dissolved in N,N-dimethylformamide (50 ml), and iodothane (3.0 ml) and potassium carbonate (5.25 g) were added. The mixture was stirred at room temperature for 15 hours, poured into water and extracted with diethyl ether. The extract was washed with 5% aqueous potassium hydrogen sulfate, dried over anhydrous magnesium sulfate and concentrated under reduced pressure. The residue was subjected to silica gel column chromatography, and the desired fractions were concentrated under reduced pressure to give 4-methoxy-2-thiophenecarboxylic acid ethyl ester (2.69 g) and 3-methoxy-2-thiophenecarboxylic acid ethyl ester (3.98 g). 4-Methoxy-2-thiophenecarboxylic acid ethyl ester (2.69 g) was dissolved in a mixture of ethanol (25 ml) and tetrahydrofuran (25 ml), and 1N aqueous sodium hydroxide (22 ml) was added. The mixture was stirred at room temperature for 3 hours and washed with diethyl ether. The aqueous layer was acidified with 1N hydrochloric acid and extracted with ethyl acetate. The extract was dried over anhydrous magnesium sulfate and concentrated under reduced pressure to give 4-methoxy-2-thiophenecarboxylaic acid (2.11 g) as crystals.
mp 172°–173° C.

Reference Example 137

2,5-Dichloro-3-thiophenecarboxylic Acid

3-Thiophenecarboxylic acid ethyl ester (1.56 g) was dissolved in acetonitrile (30 ml), and sulfuryl chloride (5.36 g) was added. The mixture was stirred at room temperature for 4 hours, and 10% aqueous sodium thiosulfate (100 ml) was added. The mixture was stirred for 15 minutes and extracted with diethyl ether. The extract was washed with saturated aqueous sodium chloride, dried over anhydrous magnesium sulfate and concentrated under reduced pressure to give 2,5-dichloro-3-thiophenecarboxylic acid ethyl ester (2.3 g). 2,5-Dichloro-3-thiophenecarboxylic acid ethyl ester (2.25 g) was dissolved in a mixture of ethanol (10 ml) and tetrahydrofuran (10 ml), and 1N aqueous sodium hydroxide (20 ml) was added. The mixture was stirred at room temperature for 2 hours and washed with diethyl ether. The aqueous layer was acidified with 1N hydrochloric acid and extracted with ethyl acetate. The extract was dried over anhydrous magnesium sulfate and concentrated under reduced pressure to give 2,5-dichloro-3-thiophenecarboxylic acid (1.89 g) as crystals.
mp 140°–141° C.

Reference Example 138

2-Bromo-3-thiophenecarboxylic Acid

A mixture of 2-bromo-3-methylthiophene (17.7 g), N-bromosuccinimide (17.7 g), 2,2'-azobis(isobutyronitrile) (0.32 g) and carbon tetrachloride (200 ml) was stirred for 4 hours under reflux. The mixture was concentrated under reduced pressure and the residue was purified by silica gel column chromatography to give 3-bromomethyl-2-bromothiophene (12.56 g). A suspension of 3-bromomethyl-2-bromothiophene (6.30 g), potassium acetate (9.8 g) in acetone (100 ml) was stirred at room temperature for 3 hours. The mixture was poured into water and extracted with ethyl acetate. The extract was dried over anhydrous magnesium sulfate and concentrated under reduced pressure to give a crude product of 3-acetoxymethyl-2-bromothiophene (5.8 g). This crude product was dissolved in tetrahydrofuran (50 ml), and 1N aqueous sodium hydroxide (50 ml) and ethanol (20 ml) were added. The mixture was stirred at room temperature for 2 hours and washed with diethyl ether. The aqueous layer was acidified with 1N hydrochloric acid and extracted with ethyl acetate. the extract was dried over anhydrous magnesium sulfate and concentrated under reduced pressure to give a crude product of 3-hydroxymethyl-2-bromothiophene (4.6 g). This crude product of 3-hydroxymethyl-2-bromothiophene was dissolved in methylene chloride (100 ml), manganese dioxide (15 g) was added. The mixture was stirred at room temperature for 6 hours, and insoluble substances were removed by filtration. The filtrate was concentrated under reduced pressure to give a crude product of 2-bromo-3-thiophenecarbaldehyde (3.92 g). The crude product of 2-bromo-3-thiophenecarbaldehyde was dissolved in acetonitrile (50 ml), and sodium dihydrogen phosphate (1.0 g) in water (15 ml) and 30% aqueous hydrogen peroxide (2.5 ml) were added. Further, sodium chlorite (2.7 g) in water (30 ml) was added dropwise under ice-cooling. The mixture was stirred at room temperature for 2 hours, alkalified with 1N aqueous sodium hydroxide (2.7 g) and washed with diethyl ether. The aqueous layer was acidified with 1N hydrochloric acid and extracted with ethyl acetate. The extract was dried over anhydrous magnesium sulfate and concentrated under reduced pressure to give 2-bromo-3-thiophenecarboxylic acid (2.89 g) as crystals.
mp 151°–154° C.

Reference Example 139

3-Ethyl-2-thiophenecarboxylic Acid

A mixture of 3-acetylthiophene (20 g), ethyleneglycol (10.54 g), p-toluenesulfonic acid (0.15 g) and toluene (200 ml) was stirred for 16 hours under reflux with removing azeotropic water by Dean-Stark trap. The mixture was cooled, washed with water, dried over anhydrous magnesium sulfate and concentrated under reduced pressure. The residue was purified by silica gel column chromatography to give 2-methyl-2-(3-thienyl)-1,3-dioxolan (12.6 g). 2-Methyl-2-(3-methyl-2-(3-thienyl)-1,3-dioxolan (12.0 g) was dissolved in tetrahydrofuran (200 ml), and N,N,N',N'-tetramethylethylenediamine (1.3 ml) was added. The mixture was cooled to -78° C, and n-butyllithium (1.6M in hexane, 49 ml) was slowly added dropwise. The mixture was stirred at the same temperature for 2 hours, and then warmed slowly to room temperature for a period of 2 hours with introducing carbon dioxide gas. The reaction mixture was concentrated under reduced pressure, and 2N hydrochloric acid (200 ml) was added. The mixture was stirred for 3 hours, and precipitated crystals were collected by filtration, washed with water and dried to give 3-acetyl-2-thiophenecarboxylic acid (10 g) as crystals.
mp 155°–156° C.

3-Acetyl-2-thiophenecarboxylic acid (3.0 g) was dissolved in N,N-dimethylformamide (50 ml), and iodomethane (4.0 ml) and potassium carbonate (6.0 g) were added. The mixture was stirred at room temperature for 3 hours, poured into water and extracted with ethyl acetate. The extract was dried over anhydrous magnesium sulfate and concentrated under reduced pressure to give 3-acetyl-2-thiophenecarboxylic acid methyl ester (3.07 g) as crystals. mp 59°–60° C.

3-Acetyl-2-thiophenecarboxylic acid methyl ester (3.87 g) synthesized in this manner was dissolved in methanol (50 ml), and sodium borohydride (0.95 g) was added under ice-cooling. The mixture was stirred at room temperature for 1 hour, and 1N hydrochloric acid (50 ml) was added. The mixture was extracted with ethyl acetate, and the extract was dried over anhydrous magnesium sulfate and concentrated under reduced pressure to give 3-(1-hydroxyethyl)-2-thiophenecarboxylic acid methyl ester (3.77 g). This product was dissolved in ethyl acetate (100 ml), and methanesulfonyl chloride (2.86 g), triethylamine (3.5 g) and dimethylaminopyridine (0.2 g) were added. The mixture was stirred at room temperature for 2 hours, and 1N hydrochloric acid (50 ml) was added. The mixture was extracted with ethyl acetate, and the extract was dried over anhydrous magnesium sulfate and concentrated under reduced pressure. The residue was dissolved in acetone (100 ml), and sodium iodide (10 g) was added. The mixture was stirred at room temperature for 2 hours, and insoluble substances were removed by filtration. The filtrate was concentrated under reduced pressure, and the residue was purified by silica gel column chromatography. The desired fractions were concentrated under reduced pressure to give 3-(1-iodoethyl)-2-thiophenecarboxylic acid methyl ester (3.0 g). 3-(1-iodoethyl)-2-thiophenecarboxylic acid methyl ester was dissolved in dimethylsulfoxide (10 ml), and sodium borohydride (0.4 g) was added at room temperature. The mixture was stirred for 1 hour, and 1N hydrochloric acid was added. The mixture was extracted with ethyl acetate, and the extract was dried over anhydrous magnesium sulfate and concentrated under reduced pressure. The residue was purified by silica gel column chromatography to give 3-ethyl-2-thiophenecarboxylic acid methyl ester (1.0 g). A mixture of 3-ethyl-2-thiophenecarboxylic acid methyl ester (1.0 g), 1N aqueous sodium hydroxide (15 ml), tetrahydrofuran (30 ml) and methanol (10 ml) was stirred at room temperature for 1 hour. The mixture was washed with diethyl ether, and the aqueous layer was acidified with 1N hydrochloric acid and extracted with diethyl ether. The extract was dried over anhydrous magnesium sulfate and concentrated under reduced pressure to give 3-ethyl-2-thiophenecarboxylic acid (0.9 g) as crystals. mp 106°–109° C.

Reference Example 140

4-Methyl-2-thiophenecarboxylic Acid

5-Bromo-4-methyl-2-thiophenecarboxylic acid (3.33 g) was dissolved in dimethylformamide (50 ml), and potassium carbonate (4.0 g) and iodomethane (4.0 ml) were added. The mixture was stirred at room temperature for 2 hours, diluted with ethyl acetate, washed with 1N hydrochloric acid, dried over anhydrous magnesium sulfate and concentrated under reduced pressure to give 5-bromo-4-methyl-2-thiophenecarboxylic acid methyl ester (3.47 g). A mixture of 5-bromo-4-methyl-2-thiophenecarboxylic acid methyl ester (2.36 g), zinc powder (1.65 g), acetic acid (10 ml) and water (10 ml) was stirred under reflux for 3 hours. Zinc powder (1 g) and acetic acid (10 ml) were further added. The mixture was stirred under reflux for 1 day, cooled, poured into concentrated aqueous ammonia and extracted with ethyl acetate. The extract was dried over anhydrous magnesium sulfate and concentrated under reduced pressure to give 4-methyl-2-thiophenecarboxylic acid methyl ester (1.42 g). 4-Methyl-2-thiophenecarboxylic acid methyl ester (1.42 g) was dissolved in a mixture of methanol (10 ml) and tetrahydrofuran (30 ml), and 1N aqueous sodium hydroxide (15 ml) was added. The mixture was stirred at room temperature for 1 hour and washed with diethyl ether. The aqueous layer was acidified with 1N hydrochloric acid and extracted with diethyl ether. The extract was dried over anhydrous magnesium sulfate and concentrated under reduced pressure to give 4-methyl-2-thiophenecarboxylic acid (1.16 g).

Reference Example 141

5-Bromo-4-methyl-2-thiophenecarboxylic Acid

Aluminum chloride (14.6 g) was added portionwise to 2-bromo-3-methylthiophene (8.85 g) and dichloromethyl methyl ether (6.27 g) in dichloromethane (100 ml) under ice-cooling. The mixture was stirred at room temperature for 1 hour and poured into ice water, acidified with 1N hydrochloric acid and extracted with ethyl acetate. The extract was washed with aqueous sodium chloride, dried over anhydrous magnesium sulfate and concentrated under reduced pressure. The residue was purified by silica gel column chromatography to give 5-bromo-4-methyl-2-thiophenecarbaldehyde (8.0 g). 5-Bromo-4-methyl-2-thiophenecarbaldehyde (6.18 g) was dissolved in acetonitrile (100 ml), and sodium dihydrogen phosphate (1.3 g) in water (20 ml) and 30% aqueous hydrogen peroxide (3.8 ml) were added. Further sodium chlorite (4.07 g) in water (50 ml) was added dropwise under ice-cooling. The mixture was stirred at room temperature for 2 hours, alkalified with 1N aqueous sodium hydroxide and washed with diethyl ether. The aqueous layer was acidified with 1N hydrochloric acid and extracted with ethyl acetate. The extract was dried over anhydrous magnesium sulfate and concentrated under reduced pressure to give 5-bromo-4-methyl-2-thiophenecarboxylic acid (6.01 g) as crystals. mp 159°–161° C.

Reference Example 142

5-Difluoromethyl-3-thiophenecarboxylic Acid

5-Bromo-3-thiophenecarboxylic acid (4.14 g) was dissolved in tetrahydrofuran (50 ml), and the mixture was cooled to -78° C. n-Butyllithium (1.6M in hexane, 27.5 ml) was slowly added dropwise. The resulting mixture was stirred at the same temperature for 1 hour, and N,N-dimethylformamide (3.1 ml) was added. The mixture was warmed slowly to room temperature and concentrated under reduced pressure. The concentrate was acidified with 1N hydrochloric acid and extracted with ethyl acetate. The extract was dried over anhydrous magnesium sulfate and concentrated under reduced pressure to give a crude product of 5-formyl-3-thiophenecarboxylic acid (3.12 g). 5-Formyl-3-thiophenecarboxylic acid (3.12 g) was dissolved in N,N-dimethylformamide (50 ml), and iodoethane (1.58 ml) and potassium carbonate (2.76 g) were added. The mixture was stirred at room temperature for 15 hours, poured into water and extracted with ethyl acetate. The extract was washed with 5 % potassium hydrogen sulfate, dried over anhydrous magnesium sulfate and concentrated under reduced pressure. The residue was subjected to silica gel column chromatography, and the desired fractions were concentrated under reduced pressure to give 5-formyl-3-thiophenecarboxylic acid ethyl ester (0.71 g). 5-Formyl-3-thiophenecarboxylic acid ethyl ester (1.47 g) synthesized in this manner in methylene chloride (10 ml) was slowly added dropwise to diethylaminosulfur trifluoride (DAST) (1.2 ml)

in methylene chloride (10 ml) at room temperature. The mixture was stirred at room temperature for 15 hours, and saturated aqueous sodium bicarbonate was added. The organic layer was collected, dried over anhydrous magnesium sulfate and concentrated under reduced pressure. The residue was purified by silica gel column chromatography to give 5-difluoromethyl-3-thiophenecarboxylic acid ethyl ester (0.7 g). 5-Difluoromethyl-3-thiophenecarboxylic acid ethyl ester was dissolved in a mixture of ethanol (5 ml) and tetrahydrofuran (5 ml), and 1N aqueous sodium hydroxide (5 ml) was added. The mixture was stirred at room temperature for 1 hour and washed with diethyl ether. The aqueous layer was acidified with 1N hydrochloric acid and extracted with ethyl acetate. The extract was dried over anhydrous magnesium sulfate and concentrated under reduced pressure to give 5-difluoromethyl-3-thiophenecarboxylic acid (0.58 g) as crystals.
mp 131°–132° C.

Reference Example 143

2,5-Dimethyl-3-thiophenecarboxylic Acid

Phosphorus oxychloride (10 ml) was slowly added dropwise to dimethylformamide (30 g) under ice-cooling, and 2,5-dimethylthiophene (11.2 g) was added. The mixture was stirred at 100° C. for 15 hours, poured into water and extracted with ethyl acetate. The extract was dried over anhydrous magnesium sulfate and concentrated under reduced pressure. The residue was purified by silica gel column chromatography to give 2,5-dimethyl-3-thiophenecarbaldehyde (1.41 g). 2,5-Dimethyl-3-thiophenecarbaldehyde (3.89 g) synthesized in this manner was dissolved in acetonitrile (30 ml), and sodium dihydrogen phosphate (1.2 g) in water (15 ml) and 30% aqueous hydrogen peroxide (3.5 ml) were added dropwise. The mixture was stirred at room temperature for 2 hours, alkalified with 1N aqueous sodium hydroxide and washed with diethyl ether. The aqueous layer was acidified with 1N hydrochloric acid and extracted with ethyl acetate. The extract was dried over anhydrous magnesium sulfate and concentrated under reduced pressure to give 2,5-dimethyl-3-thiophenecarboxylic acid (4.09 g) as crystals.
mp 113°–114° C.

Reference Example 144

4-Chloro-5-methyl-2-thiophenecarboxylic Acid

5-Methyl-2-thiophenecarboxylic acid (2.84 g) was dissolved in N,N-dimethylformamide (30 ml), and iodoethane (1.68 ml) and potassium carbonate (2.76 g) were added. The mixture was stirred at room temperature for 15 hours, poured into water and extracted with diethyl ether. The extract was washed with 5% aqueous potassium hydrogen sulfate, dried over anhydrous magnesium sulfate and concentrated under reduced pressure to give 2-methyl-3-thiophenecarboxylic acid ethyl ester (1.84 g). 5-Methyl-2-thiophenecarboxylic acid ethyl ester (1.84 g) was dissolved in acetonitrile (30 ml), and sulfuryl chloride (1.31 ml) in acetonitrile (20 ml) was added dropwise. The mixture was stirred for 1.5 hour over a water bath, and 10% aqueous sodium thiosulfate (100 ml) was added. The mixture was stirred at room temperature for 2 hours and extracted with diethyl ether. The extract was washed with saturated aqueous sodium chloride, dried over anhydrous magnesium sulfate and concentrated under reduced pressure. The residue was purified by silica gel column chromatography, and the desired fractions were concentrated under reduced pressure to give 4-chloro-5-methyl-2-thiophenecarboxylic acid ethyl ester (1.67 g). 4-Chloro-5-methyl-2-thiophenecarboxylic acid ethyl ester (1.67 g) was dissolved in a mixture of ethanol (10 ml) and tetrahydrofuran (10 ml), and 1N aqueous sodium hydroxide (16 ml) was added. The mixture was stirred at 60° C. for 2 hours and washed with diethyl ether. The aqueous layer was acidified with 1N hydrochloric acid and extracted with ethyl acetate. The extract was dried over anhydrous magnesium sulfate and concentrated under reduced pressure to give 4-chloro-5-methyl-2-thiophenecarboxylic acid (0.98 g) as crystals.
mp 164°–165° C.

Reference Example 145

5-Chloro-4-methyl-2-thiophenecarboxylic Acid

4-Methyl-2-thiophenecarboxylic acid ethyl ester (3.4 g) synthesized in accordance with the method of Reference Example 140 was dissolved in acetonitrile (30 ml), and sulfuryl chloride (2.4 ml) in acetonitrile (20 ml) was added dropwise. The mixture was stirred at room-temperature for 30 minutes, and 10% aqueous sodium thiosulfate (100 ml) was added. The mixture was stirred at room temperature for 2 hours and extracted with diethyl ether. The extract was washed with saturated aqueous sodium chloride, dried over anhydrous magnesium sulfate and concentrated under reduced pressure. The residue was purified by silica gel column chromatography, and the desired fractions were concentrated under reduced pressure to give 5-chloro-4-methyl-2-thiophenecarboxylic acid ethyl ester (4.09 g). 5-Chloro-4-methyl-2-thiophenecarboxylic acid ethyl ester (4.09 g) was dissolved in a mixture of ethanol (20 ml) and tetrahydrofuran (20 ml), and 1N aqueous sodium hydroxide (40 ml) was added. The mixture was stirred at 60° C for 2 hours and washed with diethyl ether. The aqueous layer was acidified with 1N hydrochloric acid and extracted with ethyl acetate. The extract was dried over anhydrous magnesium sulfate and concentrated under reduced pressure to give 5-chloro-4-methyl-2-thiophenecarboxylic acid (2.37 g) as crystals.
mp 144°–145° C.

Reference Example 146

4,5-Dichloro-2-thiophenecarboxylic Acid

5-Chloro-2-thiophenecarboxylic acid (6.50 g) was dissolved in N,N-dimethylformamide (30 ml), and ethyl iodide (3.2 ml) and potassium carbonate (5.52 g) were added. The mixture was stirred at room temperature for 15 hours, poured into water and extracted with diethyl ether. The extract was washed with 5% aqueous potassium hydrogen sulfate, dried over anhydrous magnesium sulfate and concentrated under reduced pressure to give 5-chloro-2-thiophenecarboxylic acid ethyl ester (5.27 g). 5-Chloro-2-thiophenecarboxylic acid ethyl ester (2.23 g) was dissolved in acetonitrile (30 ml), and sulfuryl chloride (1.4 ml) in acetonitrile (20 ml) was added dropwise. The mixture was stirred at room temperature for 48 hours, and 10% aqueous sodium thiosulfate (100 ml) was added. The mixture was stirred at room temperature for 2 hours and extracted with diethyl ether. The extract was washed with saturated aqueous sodium chloride, dried over anhydrous magnesium sulfate and concentrated under reduced pressure. The residue was purified by silica gel chromatography. The desired fractions were concentrated under reduced pressure to give 4,5-dichloro-2-thiophenecarboxylic acid ethyl ester (6.21 g). 4,5-Dichloro-2-thiophenecarboxylic acid ethyl ester (6.21 g)

was dissolved in a mixture of ethanol (25 ml) and tetrahydrofuran (25 ml), and 1N aqueous sodium hydroxide (50 ml) was added. The mixture was stirred at 60° C. for 15 hours and washed with diethyl ether. The aqueous layer was acidified with 1N hydrochloric acid and extracted with ethyl acetate. The extract was dried over anhydrous magnesium sulfate and concentrated under reduced pressure to give 4,5-dichloro-2-thiophenecarboxylic acid (2.14 g) as crystals. mp 162°–163° C.

Reference Example 147

4-Bromo-3-thiophenecarboxylic Acid

A mixture of 3-bromo-4-methylthiophene (8.85 g), N-bromosuccinimide (8.85 g), 2,2'-azobis(isobutyronitrile) (0.16 g) and carbon tetrachloride (100 ml) was stirred under reflux for 6 hours. The mixture was concentrated under reduced pressure to give a crude product of 3-bromo-4-bromomethylthiophene. A suspension of this crude product of 3-bromo-4-bromomethylthiophene and potassium acetate (30 g) in acetone (100 ml) was stirred at room temperature for 5 hours. The mixture was poured into water and extracted with ethyl acetate. The extract was dried over anhydrous magnesium sulfate and concentrated under reduced pressure to give a crude product of 4-acetoxymethyl-3-bromothiophene. This crude product was dissolved in tetrahydrofuran (50 ml), and 1N aqueous sodium hydroxide (50 ml) and ethanol (20 ml) were added. The mixture was stirred at room temperature for 2 hours and washed with diethyl ether. The aqueous layer was acidified with 1N hydrochloric acid and extracted with ethyl acetate. The extract was dried over anhdrous magnesium sulfate and concentrated under reduced pressure. The residue was purified by silica gel column chromatography to give 3-bromo-4-hydroxymethylthiophene (5.33 g) as oil. 3-Bromo-4-hydroxymethylthiophene was dissolved in methylene chloride (100 ml), and manganese dioxide (15 g) was added. The mixture was stirred at room temperature for 6 hours, and insoluble substances were removed by filtration. The filtrate was concentrated under reduced pressure to give a crude product of 4-bromo-3-thiophenecarbaldehyde. The crude product of 4-bromo-3-thiophenecarbaldehyde was dissolved in acetonitrile (50 ml), and sodium dihydrogen phosphate (1.2 g) in water (15 ml) and 30% aqueous hydrogen peroxide (3.5 ml) were added. Further, sodium chlorite (3.7 g) in water (40 ml) was added dropwise under ice-cooling. The mixture was stirred at room temperature for 2 hours, alkalified with 1N aqueous sodium hydroxide and washed with diethyl ether. The aqueous layer was acidified with 1N hydrochloric acid and extracted with ethyl acetate. The extract was dried over anhydrous magnesium sulfate and concentrated under reduced pressure to give 4-bromo-3-thiophenecarboxylic acid (3.40 g) as crystals. mp 161°–162° C.

Reference Example 148

2-Chloro-3-thiophenecarboxylic Acid

3-Methylthiophene (19.63 g) was dissolved in acetonitrile (100 ml), and sulfuryl chloride (16.64 ml) was added dropwise. The mixture was stirred at room temperature for 1 hour, stirred under reflux for another 1 hour, then cooled to room temperature, and 10% aqueous sodium thiosulfate (200 ml) was added. The mixture was stirred at room temperature for 2 hours and extracted with diethyl ether. The extract was washed with saturated aqueous sodium chloride, dried over anhydrous magnesium sulfate and concentrated under reduced pressure to give 2-chloro-3-methylthiophene (21.52 g). A mixture of 2-chloro-3-methylthiophene (3.53 g), N-bromosuccinimide (4.73 g), 2,2'-azobis (isobutyronitrile) (0.87 g) and carbon tetrachloride (25 ml) was stirred under reflux for 4 hours. The mixture was cooled to room temperature and insoluble substances were removed by filtration. The filtrate was concentrated under reduced pressure to give a crude product of 2-chloro-3-bromomethylthiophene. A suspension of the crude product of 2-chloro-3-bromomethylthiophene and potassium acetate (9.82 g) in acetone (50 ml) was stirred at room temperature for 48 hours. The mixture was poured into water and extracted with diethyl ether. The extract was dried over anhydrous magnesium sulfate and concentrated under reduced pressure to give a crude product of 3-acetoxymethyl-2-chlorothiophene. This crude product was dissolved in a mixture of ethanol (25 ml) and tetrahydrofuran (25 ml), and 1N aqueous sodium hydroxide (50 ml) was added. The mixture was stirred at room temperature for 30 minutes. The aqueous layer was acidified with 1N hydrochloric acid and extracted with ethyl acetate. The extract was dried over anhydrous magnesium sulfate and concentrated under reduced pressure to give 3-hydroxymethyl-2-chlorothiophene (3.22 g). 3-Hydroxymethyl-2-chlorothiophene (3.16 g) was dissolved in methylene chloride (50 ml), and manganese dioxide (9.66 g) was added. The mixture was stirred at room temperature for 15 hours, and insoluble substances were removed by filtration. The filtrate was concentrated under reduced pressure to give a crude product of 2-chloro-3-thiophenecarbaldehyde (3.16 g). The crude product of 2-chloro-3-thiophenecarbaldehyde was dissolved in acetonitrile (20 ml), and sodium dihydrogen phosphate (0.67 g) in water (10 ml) and 30% aqueous hydrogen peroxide (2.6 ml) were added. Further, sodium chlorite (3.41 g) in water (30 ml) was added dropwise under ice-cooling. The mixture was stirred at room temperature for 2 hours, alkalified with 1N aqueous sodium hydroxide and washed with diethyl ether. The aqueous layer was acidified with 1N hydrochloric acid and extracted with ethyl acetate. The extract was dried over anhdrous magnesium sulfate to give 2-chloro-3-thiophenecarboxylic acid (1.92 g) as crystals. mp 166°–167° C.

Reference Example 149

2-Methyl-3-furancarboxylic Acid

2-Methyl-3-furancarboxylic acid ethyl ester (10 g) was dissolved in ethanol (70 ml), and 1N aqueous sodium hydroxide (78 ml) was added. The mixture was stirred at room temperature and concentrated under reduced pressure. The residue was dissolved in water and washed with diethyl ether. The aqueous layer was acidified with 1N hydrochloric acid and extracted with ethyl acetate. The extract was washed with water and saturated aqueous sodium chloride, dried over anhydrous magnesium sulfate and concentrated under reduced pressure. Precipitated crystals were collected by filtration to give 2-methyl-3-furancarboxylic acid (5.5 g) as crystals. mp 101°–102° C.

Reference Example 150

5-Bromo-3-furancarboxyalic Acid

This compound was synthesized in accordance with the method described in J. Org. Chem., 41, 2350 (1976).

Reference Example 151

5-Chloro-2-furancarboxylic Acid

5-Chloro-2-furancarboxylic acid ethyl ester (8 g) (synthesized in accordance with the method described in Chem. Pharm. Bull., 40, 1966 (1992)) was dissolved in ethanol (50 ml), and 1N aqueous sodium hydroxide (50 ml) was added. The mixture was stirred at room temperature for 1 hour and concentrated under reduced pressure. The residue was dissolved in water and washed with diethyl ether. The aqueous layer was acidified with 1N hydrochloric acid and extracted with ethyl acetate. The extract was washed with water and saturated aqueous sodium chloride, dried over anhydrous magnesium sulfate and concentrated under reduced pressure. Precipitated crystals were collected by filtration and washed with diethyl etherhexane to give 5-chloro-2-furancarboxylic acid (5.3 g) as crystals.
mp 182°–183° C.

Reference Example 152

5-Methyl-2-furancarboxylic Acid

This compound was synthesized in accordance with the method described in J. C. S. Perkin, 1, 1125 (1981).

Reference Example 153

5-Ethyl-2-furancarboxylic Acid

2-Ethylfuran (9.1 g) was dissolved in diethyl ether, and the mixture was cooled to −70° C. under nitrogen atmosphere. n-Butyllithium (1.6M in hexane, 60 ml) was slowly added dropwise. The mixture was stirred at room temperature for 2 hours, and then cooled to −70° C. The mixture was stirred for 30 minutes with introducing carbon dioxide gas, and then warmed to room temperature. The mixture was stirred at room temperature for 30 minutes, poured into ice-water, acidified with concentrated hydrochloric acid and extracted with diethyl ether. The extract was washed with saturated aqueous sodium chloride and concentrated under reduced pressure. The residue was crystallized from water and collected by filtration to give 5-ethyl-2-furancarboxylic acid (9.0 g).
mp 92°–94° C.

Reference Example 154

2-Chloro-3-furancarboxylic Acid

2-Trimethylsilyl-3-furancarboxylic acid (16.4 g) (synthesized in accordance with the method described in J. C. S. Perkin, 1, 1125 (1981)) was dissolved in N,N-dimethylformamide (50 ml), and potassium carbonate (12.3 g) and iodoethane (13.9 g) were added. The mixture was stirred at room temperature for 15 hours, poured into ice water and extracted with diethyl ether. The extract was washed with water and saturated aqueous sodium chloride, dried over anhydrous magnesium sulfate and concentrated under reduced pressure. The residue was subjected to silica gel column chromatography, and the desired fractions were concentrated under reduced pressure to give 2-trimethylsilyl-3-furancarboxylic acid ethyl ester (16.3 g) as oil. 2-Trimethylsilyl-3-furancarboxylic acid ethyl ester (16.3 g) was dissolved in acetonitrile (75 ml), and sulfuryl chloride (10.9 g) in acetonitrile (25 ml) was added dropwise. The mixture was stirred at room temperature for 1 hour, poured into ice water and extracted with diethyl ether. The extract was washed with 10% aqueous sodium thiosulfate and saturated aqueous sodium chloride, dried over anhydrous magnesium sulfate and concentrated under reduced pressure. The residue was subjected to silica gel column chromatography, and the desired fractions were concentrated under reduced pressure to give 2-chloro-3-furancarboxylic acid ethyl ester (3.5 g) as oil. 2-Chloro-3-furancarboxylic acid ethyl ester (3.5 g) was dissolved in ethanol (25 ml), and 1N aqueous sodium hydroxide (25 ml) was added. The mixture was stirred at room temperature for 1.5 hour and concentrated under reduced pressure. The residue was dissolved in water and washed with diethyl ether. The aqueous layer was acidified with 1N hydrochloric acid and extracted with ethyl acetate. The extract was washed with water and saturated aqueous sodium chloride, dried over anhydrous magnesium sulfate and concentrated under reduced pressure. Precipitated crystals were collected by filtration and washed with diisopropyl ether-hexane to give 2-chloro-3-furancarboxylic acid (2.2 g) as crystals. mp 138°–141° C.

Reference Example 155

5-Chloro-3-furancarboxylic Acid

5-Trimethylsilyl-3-furancarboxylic acid (4.1 g) (synthesized in accordance with the method described in Tetrahedron Lett., 25, 4451 (1984)) was dissolved in tetrahydrofuran (100 ml), and N,N-dimethylformamide (3 drops) was added. Oxalyl chloride (3.0 g) was added dropwise under ice-cooling, and the mixture was stirred at room temperature for 30 minutes. Ethanol (100 ml) and triethylamine (4.7 g) were added, and the resulting mixture was stirred at room temperature for 15 hours. The mixture as concentrated under reduced pressure, and water was added to the residue. The mixture was extracted with ethyl acetate, and the extract was washed with water and saturated aqueous sodium chloride, dried over magnesium sulfate and concentrated under reduced pressure. The residue was subjected to silica gel column chromatography, and the desired fractions were concentrated under reduced pressure to give 5-trimethylsilyl-3-furancarboxylic acid ethyl ester (3.0 g) as oil. 5-Trimethylsilyl-3-furancarboxylic acid ethyl ester (3.0 g) was dissolved in acetonitrile (15 ml), and sulfuryl chloride (2.0 g) in acetonitrile (5 ml) was added dropwise. The mixture was stirred at room temperature for 30 minutes, poured into ice water and extracted with diethyl ether. The extract was washed with 10% aqueous sodium thiosulfate and saturated aqueous sodium chloride, dried over anhydrous magnesium sulfate and concentrated under reduced pressure. The residue was subjected to silica gel column chromatography, and the desired fractions were concentrated under reduced pressure to give 5-chloro-3-furancarboxylic acid ethyl ester (1.9 g) as oil. 5-Chloro-3-furancarboxylic acid ethyl ester (1.9 g) was dissolved in ethanol (15 ml), and 1N aqueous sodium hydroxide (12 ml) was added. The mixture was stirred at room temperature for 1.5 hour and concentrated under reduced pressure. The residue was dissolved in water and washed with diethyl ether. The aqueous layer was acidified with 1N hydrochloric acid and extracted with ethyl acetate. The extract was washed with water and saturated aqueous sodium chloride, dried over anhydrous magensium sulfate and concentrated under reduced pressure. Precipaitated crystals were collected by filtration and washed with hexane to give 5-chloro-3-furancarboxylic acid (1.1 g) as crystals.
mp 124°–125° C.

Reference Example 156

5-Difluoromethyl-2-furancarboxylic Acid

5-Formyl-2-furancarboxylic acid (2.9 g) was dissolved in N,N-dimethylformamide (30 ml), and potassium carbonate (2.9 g) and iodoethane (3.6 g) were added. The mixture was stirred at room temperature for 12 hours, poured into ice water and extracted with diethyl ether. The extract was washed with water and saturated aqueous sodium chloride, dried over anhydrous magnesium sulfate and concentrated under reduced pressure. The residue was subjected to silica gel column chromatography, and the desired fractions were concentrated under reduced pressure to give 5-formyl-2-furancarboxylic acid ethyl ester (1.3 g). 5-Formyl-2-furancarboxylic acid ethyl ester (1.3 g) in methylene chloride (5 ml) was slowly added dropwise to diethylaminosulfur trifluoride (DAST) (1.3 g) in methylene chloride (5 ml) at room temperature. The mixture was stirred at room temprature for 30 minutes, and water was added to the mixture. The resulting mixture was extracted with diethyl ether, and the extract was washed with water and saturated aqueous sodium chloride, dried over anhydrous magnesium sulfate and concentrated under reduced pressure. The residue was subjected to silica gel column chromatography, and the desired fractions were concentrated under reduced pressure to give 5-difluoromethyl-2-furancarboxylic acid ethyl ester (0.7 g). 5-Difluoromethyl-2-furancarboxylic acid ethyl ester (2.3 g) synthesized in this manner was dissolved in ethanol (20 ml), and 1N aqueous sodium hydroxide (15 ml) was added. The mixture was stirred at room temperature and concentrated under reduced paressure. The residue was dissolved in water and washed with diethyl ether. The aqueous layer was acidified with 1N hydrochloric acid and extracted with ethyl acetate. The extract was washed with water and saturated aqueous sodium chloride, dried over anhydrous magnesium sulfate and concentrated under reduced pressure. Precipitated crystals were collected by filtration and washed with hexane-isopropyl ether to give 5-difluoromethyl-2-furancarboxylic acid (1.2 g) as crystals.
mp 112°–113° C.

Reference Example 157

5-Methyl-2-trifluoromethyl-3-furancarboxylic Acid

This compound was synthesized in accordance with the method described in J. Heterocycl. Chem., 5, 95 (1968).

Reference Example 158

2,5-Dimethyl-3-furancarboxylic Acid 2,5-Dimethyl-3-furancarboxylic acid ethyl ester (14.6 g) (synthesized in accordance with the method described in J.A.C.S., 59, 2525 (1937)) was dissolved in ethanol (100 ml), and 1N aqueous sodium hydroxide (100 ml) was added. The mixture was stirred at room temperature for 1 hour, and then stirred under reflux for 30 minutes. The mixture was concentrated under reduced pressure, and the residue was dissolved in water and washed with diethyl ether. The aqueous layer was acidified with 1N hydrochloric acid and extracted with ethyl acetate. The extract was washed with water and saturated aqueous sodium chloride, dried over anhydrous magnesium sulfate and concentrated under reduced pressure. precipitated crystals were recrystallized from acetone-hexane to give 2,5-dimethyl-3-furancarboxylic acid (7.3 g) as crystals.
mp 139°–140° C.

Reference Example 159

5-Chloro-2-methyl-3-furancarboxylic Acid

2-Methyl-3-furancarboxylic acid ethyl ester (10.5 g) was dissolved in acetonitrile (50 ml), and sulfuryl chloride (5.6 ml) was added under ice-cooling. The mixture was stirred at 10° C. for 30 minutes, and 10% aqueous sodium thiosulfate (100 ml) was added. The mixture was stirred at room temperature for 2 hours, and extracted with diethyl ether. The extract was washed with saturated aqueous sodium chloride, dried over anhydrous magnesium sulfate and concentrated under reduced pressure. The residue was subjected to silica gel column chromatography, and the desired fractions were concentrated under reduced pressure to give 5-chloro-2-methyl-3-furancarboxylic acid ethyl ester (10 g) as oil. 5-Chloro-2-methyl-3-furancarboxylic acid ethyl ester (10 g) was dissolved in ethanol (100 ml), and 1N aqueous sodium hydroxide (60 ml) was added. The mixture was stirred under reflux for 30 minutes and concentrated under reduced pressure. The residue was dissolved in water and washed with diethyl ether. The aqueous layer was acidified with 1N hydrochloric acid and extracted with ethyl acetate. The extract was washed with water and saturated aqueous sodium chloride, dried over anhydrous magnesium sulfate and concentrated under reduced pressure. Precipitated crystals were recrystallized from acetone-hexane to give 5-chloro-2-methyl-3-furancarboxylic acid (5.5 g) as crystals.
mp 126°–127° C.

Reference Example 160

2-Ethyl-3-furancarboxylic Acid

This compound was synthesized in accordance with the method described in J. C. S. Perkin, 1, 1125 (1981).

Reference Example 161 to 169

The following compounds were synthesized in the same manner as Reference Example 60.

| Reference Example | Compound | mp (°C.) |
|---|---|---|
| 161 | 4-Chloro-2-thiophenecarboxamide | 150–151 |
| 162 | 4-Methyl-3-thiophenecarboxamide | 140–142 |
| 163 | 5-Bromo-2-chloro-3-thiophenecarboxamide | 130–131 |
| 164 | 5-Chloro-4-methyl-3-thiophenecarboxamide | 172–173[4] |
| 165 | 2,5-Dichloro-4-methyl-3-thiophenecarboxamide | 181–182[4] |
| 166 | 2-Chloro-5-methyl-3-thiophenecarboxamide | 107–108 |
| 167 | 3-Chloro-4-methyl-2-thiophenecarboxamide | 158–160 |
| 168 | 3,5-Dimethyl-2-thiophenecarboxamide | 114–116 |
| 169 | 3-Methyl-2-furancarboxamide | 66–68 |

4) These compounds were synthesized in the following manner.

5-Chloro-4-methyl-3-thiophenecarboxamide and 2,5-dichloro-4-methyl-3-thiophenecarboxamide 4-Methyl-3-thiophenecarboxylic acid (1.42 g) (synthesized in accordance with the method described in J. Org. Chem., 51, 230 (1986)) was dissolved in N,N-dimethylformamide (30 ml), and iodoethane (0.8 ml) and potassium carbonate (1.38 g) were added. The mixture was stirred at room temperature for 15 hours, poured into water. and extracted with diethyl ether. The extract was washed with 5% aqueous potassium hydrogen sulfate, dried over anhydrous magnesium sulfate and concentrated under reduced pressure to give ethyl 4-methyl-3-thiophenecarboxylate (1.7 g). Ethyl 4-methyl-3-thiophenecarboxylate (1.7 g) was dissolved in acetonitrile (30 ml), and sulfuryl chloride (1.2 ml) in acetonitrile (20 ml) was added. The mixture was stirred at room temperature for 1 hour, and then 10% aqueous sodium thiosulfate (100 ml) was added and stirred at room temperature for 2 hours. The mixture was extracted with ethyl acetate, dried over anhydrous magnesium sulfate and concentrated under reduced pressure to give a mixture of ethyl 5-chloro-4-methyl-3-thiophenecarboxylate and ethyl 2,5-dichloro-4-methyl-3-thiophenecarboxylate. The mixture of ethyl 5-chloro-4-methyl-3-thiophenecarboxylate and 2,5-dichloro- 4-methyl-3-thiophenecarboxylate was dissolved in ethanol (10 ml) and tetrahydrofuran (10 ml), and 1N aqueous sodium hydroxide (20 ml) was added. The mixture was stirred at room temperature for 2 hours, and washed with diethyl ether. The aqueous layer was acidified with 1N hydrochloric acid and extracted with ethyl acetate. The extract was dried over anhydrous magnesium sulfate and concentrated under reduced pressure to give a mixture of 5-chloro-4-methyl-3-thiophenecarboxylic acid and 2,5-dichloro-4-methyl-3-thiophenecarboxylic acid. The mixture was suspended in toluene (15 ml). Oxalyl chloride (1.31 ml) was added dropwise and then N,N-dimethylformamide (1 drop) was added. The mixture was stirred at room temperature for 1 hour and concentrated under reduced pressure. The residue was dissolved in ethyl acetate (5 ml) and added dropwise into a mixture of 25% aqueous ammonia solution (16 ml) and ethyl acetate (50 ml) with stirring under ice-cooling. The resulting mixture was stirred at room temperature for 10 minutes. The organic layer was collected and the aqueous layer was extracted with ethyl acetate. The organic layers were combined and dried over anhydrous magnesium sulfate and concentrated under reduced pressure. The residue was purified by silica gel column chromatography to give 5-chloro-4-methyl-3-thiophenecarboxamide (0.83 g) and 2,5-dichloro-4-methyl-3-thiophenecarboxamide (0.61 g).

Reference Example 170

4-Chloro-2-thiophenecarboxylic Acid

This compound was synthesized in accordance with the method described in J. Heterocyclic Chem., 13, 393 (1976).

Reference Example 171

4-Methyl-3-thiophenecarboxylic Acid

This compound was synthesized in accordance with the method described in J. Org. Chem., 51, 230 (1986).

Reference Example 172

5-Bromo-2-chloro-3-thiophenecarboxylic Acid

A mixture of 2-chloro-3-thiophenecarboxylic acid (2.44 g), pyridinium bromide perbromide (5.33 g) and acetic acid (15 ml) was stirred at 40° C. for 4 hours and poured into ice-water. Precipitated crystals were collected by filtration, dissolved in ethyl acetate and dried over anhydrous magnesium sulfate. The solution was concentrated under reduced pressure to give 5-bromo-2-chloro-3-thiophenecarboxylic acid (2.81 g) as crystals.
mp 159°–160° C.

Reference Example 173

2-Chloro-5-methyl-3-thiophenecarboxylic Acid

5-Bromo-2-chloro-3-thiophenecarboxylic acid (2.41 g) was dissolved in tetrahydrofuran (50 ml), and the mixture was cooled to -78° C. N-Butyllithium (1.6M in hexane, 14 ml) was slowly added dropwise. The mixture was stirred at −78° C. for 1 hour, and iodomethane (1.4 ml) was added dropwise. The reaction mixture was warmed to room temperature, stirred at room temperature for 15 hours, poured into water, acidified with 1N hydrochloric acid and extracted with ethyl acetate. The extract was dried over anhydrous magnesium sulfate and concentrated under reduced pressure to give 2-chloro-5-methyl-3-thiophenecarboxylic acid (1.7 g) as crystals.

Reference Example 174

3,5-Dimethyl-2-thiophenecarboxylic Acid

3-Methyl-2-thiophenecarboxylic acid (7.11 g) was dissolved in tetrahydrofuran (100 ml), and the mixture was cooled to −78° C. n-Butyllithium (1.6M in hexane, 69 ml) was slowly added dropwise. The mixture was stirred at −78° C. for 1 hour, and iodomethane (6.2 ml) was added dropwise. The reaction mixture was warmed to room temperature, stirred at room temperature for 15 hours, poured into water, acidified with 1N hydrochloric acid and extracted with ethyl acetate. The extract was dried over anhydrous magnesium sulfate and concentrated under reduced pressure to give 3,5-dimethyl-2-thiophenecarboxylic acid (4.97 g) as crystals.
mp 153°–155° C.

Reference Example 175

3-Methyl-2-furancarboxylic Acid

This compound was synthesized in accordance with the method described in Org. Synth., IV, 628.

Example 1

N-(Diaminophosphinyl)-2-thiophenecarboxamide

2-Thiophenecarboxamide (3.82 g) was suspended in toluene (25 ml), and phosphorus pentachloride (6.25 g) was added portionwise. The mixture was stirred at 65° C. for 3 hours and then cooled to room temperature. Formic acid (1.38 g) was added dropwise. The mixture was stirred at room temperature for 1 hour, and precipitated crystals were collected by filtration, washed with toluene and dried to give 6.67 g of crystals. The crystals were dissolved in tetrahydrofuran (100 ml), and ammonia gas was introduced under ice-cooling for 30 minutes. The mixture was stirred at room temperature for 1 hour. Precipitate was collected by filtration, washed with water and dried. The obtained solid was recrystallized from water to give N-(diaminophosphinyl)-2-thiophenecarboxamide (1.56 g) as colorless crystals.
mp 272°–280° C.
Elemental Analysis for $C_5H_8N_3O_2SP$
Calcd: C, 29.27; H, 3.93; N, 20.48. Found: C, 29.42; H, 4.00; N, 20.40. $^1$H-NMR (DMSO-$d_6$) δ: 4.23(4H,br s), 7.14–7.18(1H,m), 7.83–8.15(1H,d,J=5.2 Hz), 8.13(1H,m), 9.16(1H,br s).

Example 2

N-(Diaminophosphinyl)-3-thiophenecarboxamide

3-Thiophenecarboxamide (3.18 g) was suspended in toluene (25 ml), and phosphorus pentachloride (5.21 g) was added portionwise. The mixture was stirred at 65° C. for 3 hours and then cooled to room temperature. Formic acid (1.15 g) was added dropwise, and the mixture was stirred at room temperature for 1 hour. Precipitated crystals were collected by filtration, washed with toluene and dried to give 5.43 g of crystals. The crystals were dissolved in tetrahydrofuran (100 ml), and ammonia gas was introduced under ice-cooling for 30 minutes. The mixture was stirred at room temperature for 1 hour, and precipitate was collected by filtration, washed with water and dried. The obtained solid was recrystallized from methanol to give N-(diaminophosphinyl)-3-thiophenecarboxamide (1.05 g) as colorless crystals.
mp 269°–278° C.
Elemental Analysis for $C_5H_8N_3O_2SP$
    Calcd: C, 29.27; H, 3.93; N, 20.48. Found: C, 29.12; H, 3.78; N, 20.62. $^1$H-NMR (DMSO-$d_6$) δ: 4.20(4H,br s), 7.57–7.64(2H,m), 8.48–8.50(1H,m), 9.13(1H,br s).

Example 3

N-(Diaminophosphinyl)-5-methyl-2-thiophenecarboxamide

5-Methyl-2-thiophenecarboxamide (4.24 g) was suspended in toluene (25 ml), and phosphorus pentachloride (6.25 g) was added portionwise. The mixtuere was stirred at 65° C. for 1 hour, and then cooled to room temperature. Formic acid (1.38 g) was added dropwise, and the mixture was stirred at room temperature for 2 hours. Precipitated crystals were collected by filtration, washed with toluene and dried to give 6.93 g of crystals. The crystals were dissolved in tetrahydrofuran (100 ml), and ammonia gas was introduced under ice-cooling for 30 minutes. The mixture was stirred at room temperature for 1 hour, and precipitate was collected by filtration, washed with water and dried. The obtained solid was recrystallized from water-methanol to give N-(diaminophosphinyl)-5-methyl-2-thiophenecarboxamide (3.86 g) as colorless crystals.
mp 284°–293° C.
Elemental Analysis for $C_6H_{10}N_3O_2SP$
    Calcd: C, 32.88; H, 4.60; N, 19.17. Found: C, 32.68; H, 4.67; N, 19.17. $^1$H-NMR (DMSO-d6) δ: 2.49(3H,s), 4.20 (4H,br s), 6.87(1H,d,J=3.6 Hz), 7.94(1H,d,J=3.6 Hz), 9.27 (1H,br s).

Example 4

N-(Diaminophosphinyl)-3-methyl-2-thiophenecarboxamide

3-Methyl-2-thiophenecarboxamide (4.24 g) was suspended in toluene (25 ml), and phosphorus pentachloride (6.25 g) was added portionwise. The mixture was stirred at 65° C. for 1 hour, and then cooled to room temperature. Formic acid (1.38 g) was added dropwise, and the mixture was stirred at room temperature for 1 hour. Hexane was added, and the resulting mixture was stirred for 30 minutes. Precipitated crystals were collected by filtration, washed with toluene and dried to give 7.10 g of crystals. The crystals were dissolved in tetrahydrofuran (100 ml), and ammonia gas was introduced under ice-cooling for 30 minutes. The mixture was stirred at room temperature for 1 hour, and precipitate was collected by filtration and washed with water to give N-(diaminophosphinyl)-3-methyl-2-thiophenecarboxamide (2.50 g) as colorless crystals.
mp 267°–275° C.
Elemental Analysis for $C_6H_{10}N_3O_2SP$
    Calcd: C, 32.88; H, 4.60; N, 19.17. Found: C, 33.26; H, 4.55; N, 19.35. $^1$-H-NMR (DMSO-$d_6$) δ: 2.47(3H,s), 4.20 (4H,br s), 6.84(1H,d,J=3.7 Hz), 7.94(1H,d,J=3.7 Hz), 9.50 (1H,d,J=7.2 Hz).

Examples 5 to 38

The following compounds were synthesized in the same manner as Example 1.

Example 5

N-(Diaminophosphinyl)-5-chloro-2-thiophenecarboxamide
mp 273°–279° C.
Elemental Analysis for $C_5H_7N_3O_2SClP$
    Calcd: C, 25.06; H, 2.94; N, 17.54. Found: C, 25.10; H, 2.88; N, 17.55. $^1$H-NMR (DMSO-$d_6$) δ: 4.25(4H,br s), 7.22(1H,d,J=4.0 Hz), 8.01(1H,d,J=4.0 Hz), 9.48(1H,br s).

Example 6

N-(Diaminophosphinyl)-5-bromo-2-thiophenecarboxamide
mp 238°–244° C.
Elemental Analysis for $C_5H_7N_3O_2SBrP$
    Calcd: C, 21.14; H, 2.48; N, 14.79. Found: C, 21.22; H, 2.45; N, 14.88. $^1$H-NMR (DMSO-$d_6$) δ: 4.25(4H,br s), 7.32(1H,d,J=4.0 Hz), 7.95(1H,d,J=4.0 Hz), 9.47(1H,d,J=7.4 Hz).

Example 7

N-(Diaminophosphinyl)-4,5-dibromo-2-thiophenecarboxamide
mp 257°–266° C.
Elemental Analysis for $C_5H_6N_3O_2SBr_2P$
    Calcd: C, 16.55; H, 1.67; N, 11.58. Found: C, 16.70; H, 1.55; N, 11.46. $^1$H-NMR (DMSO-$d_6$) δ: 4.28(4H,br s), 8.14(1H,s), 9.65(1H,d,J=6.4 Hz).

Example 8

N-(Diaminophosphinyl)-4-bromo-thiophenecarboxamide
mp 263°–268° C.
Elemental Analysis for $C_5H_7N_3O_2SBrP$
    Calcd: C, 21.14; H, 2.48; N, 14.79. Found: C, 21.27; H, 2.39; N, 14.75. $^1$H-NMR (DMSO-$d_6$) δ: 4.24(4H,br S)r 7.96(1H,d,J=1.4 Hz), 8.13(1H,d,J=1.4 Hz), 9.58(1H,br s).

Example 9

N-(Diaminophosphinyl)-5-ethyl-2-thiophenecarboxamide
mp 167°–174° C.
Elemental Analysis for $C_7H_{12}N_3O_2SP$
    Calcd: C, 36.05; H, 5.19; N, 18.02. Found: C, 35.97; H, 5.02; N, 18.16. $^1$H-NMR (DMSO-$d_6$) δ: 1.24(3H,t,J=7.0 Hz), 2.82(2H,q,J=7.0 Hz), 4.16(4H,br s), 6.88(1H,d,J=4.0 Hz), 7.91(1H,d,J=4.0 Hz), 9.35(1H,br d, J=7.0 Hz).

Example 10

N-(Diaminophosphinyl)-5-nitro-thiophenecarboxamide
mp 183°–187° C.
Elemental Analysis for $C_5H_7N_4O_4SP$
    Calcd: C, 24.01; H, 2.82; N, 22.40. Found: C, 24.44; H, 2.92; N, 22.35. $^1$H-NMR (DMSO-$d_6$) δ: 4.36(4H,br s), 8.04–8.32(2H,m), 10.01(1H,br s).

Example 11

N-(Diaminophosphinyl)-5-bromo-3-thiophenecarboxamide
mp 193°–196° C.
Elemental Analysis for $C_5H_7N_3O_2SBrP$
    Calcd: C, 21.14; H, 2.48; N, 14.79. Found: C, 21.38; Hr 2.23; N, 15.04. $^1$H-NMR (DMSO-$d_6$) δ: 4.17(4H,br s), 7.68(1H,d,J=1.6 Hz), 8.40(1H,d,J=1.6 Hz), 9.28(1H,d,J=6.8 Hz).

Example 12

N-(Diaminophosphinyl)-5-cyano-2-thiophenecarboxamide mp 200°–205° C. (decomp.).

Elemental Analysis for $C_6H_7N_4O_2SP$

Calcd: C, 31.31; H, 3.07; N, 24.34. Found: C, 31.42; H, 3.03; N, 24.17. $^1$H-NMR (DMSO-$d_6$) δ: 4.28(4H,s), 7.98 (1H,d,J=4.0 Hz), 8.17(1H,d,J=4.0 Hz), 9.84(1H,br d,J=7.0 Hz).

Example 13

N-(Diaminophosphinyl)-5-difluoromethyl-2-thiophenecarboxamide mp 165°–169° C.

Elemental Analysis for $C_6H_8N_3O_2SF_2P$

Calcd: C, 28.24; H, 3.16; N, 16.47. Found: C, 28.24; H, 2.92; N, 16.55. $^1$H-NMR (DMSO-$d_6$) δ: 4.23(4H,br s), 7.31(1H,t,J=56 Hz), 7.47(1H,m), 8.07(1H,m), 9.64(1H,br d,J=7.0 Hz).

Example 14

N-(Diaminophosphinyl)-3-chloro-2-thiophenecarboxamide mp 154°–164° C.

Elemental Analysis for $C_5H_7N_3O_2SClP$

Calcd: C, 25.06; H, 2.97; N, 17.54. Found: C, 25.15; H, 2.70; N, 17.62. $^1$H-NMR (DMSO-$d_6$) δ: 4.33(4H,br s), 7.20(1H,d,J=5.3 Hz), 7.93(1H,d,J=5.3 Hz), 8.45(1H,d,J=6.0 Hz).

Example 15

N-(Diaminophosphinyl)-2-methyl-3-thiophenecarboxamide mp 155°–157° C.

Elemental Analysis for $C_6H_{10}N_3O_2SP \cdot 1/3H_2O$

Calcd: C, 32.34; H, 4.63; N, 19.13. Found: C, 32.15; H, 4.63; N, 19.39. $^1$H-NMR (DMSO-$d_6$) δ: 2.62(3H,s), 4.13 (4H,br s), 7.35(1H,d,J=5.4 Hz), 7.54(1H,d,J=5.4 Hz), 8.98 (1H,br s).

Example 16

N-(Diaminophosphinyl)-3-bromo-2-thiophenecarboxamide mp 160°–167° C.

Elemental Analysis for $C_5H_7N_3O_2SBrP$

Calcd: C, 21.14; H, 2.48; N, 14.79. Found: C, 21.38; H, 2.44; N, 14.85. $^1$H-NMR (DMSO-$d_6$) δ: 4.31(4H,br s), 7.22(1H,d,J=5.2 Hz), 7.90(1H,d,J=5.2 Hz), 8.55(1H,d,J=6.6 Hz).

Example 17

N-(Diaminophosphinyl)-5-acetyl-2-thiophenecarboxamide mp 185° C. (decomp.).

Elemental Analysis for $C_7H_{10}N_3O_3SP$

Calcd: C, 34.01; H, 4.08; N, 17.00. Found: C, 34.34; H, 4.12; N, 17.03. $^1$H-NMR (DMSO-$d_6$) δ: 2.56(3H,s), 4.28 (4H,br s), 7.92(1H,d,J=4.0 Hz), 8.12(1H,d,J=4.0 Hz), 9.68 (1H,br m).

Example 18

N-(Diaminophosphinyl)-5-methanesulfonyl-2-thiophenecarboxamide mp 180°–185° C. (decomp.).

Elemental Analysis for $C_6H_{10}N_3O_4S_2P$

Calcd: C, 25.44; H, 3.56; N, 14.83. Found: C, 25.90; H, 3.31; N, 14.56. $^1$H-NMR (DMSO-$d_6$) δ: 3.39(3H,s), 4.28 (4H,br d,J=3.0 Hz), 7.81(1H,d,J=4.0 Hz), 8.13(1H,d,J=4.0 Hz), 9.78(1H,d,J=7.0 Hz).

Example 19

N-(Diaminophosphinyl)-3-difluoromethyl-2-thiophenecarboxamide mp 158°–162° C.

Elemental Analysis for $C_6H_8N_3O_2SF_2P$

Calcd: C, 28.24; H, 3.16; N, 16.47. Found: C, 28.43; H, 2.98; N, 16.58. $^1$H-NMR (DMSO-$d_6$) δ: 4.25(4H,br s), 7.37(1H,d,J=5.0 Hz), 7.38(1H,t,J=55 Hz), 7.87(1H,d,J=5.0 Hz), 9.35(1H,br s).

Example 20

N-(Diaminophosphinyl)-2-difluoromethyl-3-thiophenecarboxamide mp 168°–173° C.

Elemental Analysis for $C_6H_8N_3O_2SF_2P$

Calcd: C, 28.24; H, 3.16; N, 16.47. Found: C, 28.56; H, 2.93; N, 16.61. $^1$H-NMR (DMSO-$d_6$) δ: 4.22(4H,br s), 7.67(1H,t,J=55 Hz), 7.78(1H,d,J=5.3 Hz), 7.84(1H,d,J=5.3 Hz), 9.42(1H,d,J=6.6 Hz).

Example 21

N-(Diaminophosphinyl)-5-nitro-3-thiophenecarboxamide mp 181°–184° C.

Elemental Analysis for $C_5H_7N_4O_4SP$

Calcd: C, 24.01; H, 2.82; N, 22.40. Found: C, 23.97; H, 2.76; N, 22.14. $^1$H-NMR (DMSO-$d_6$) δ: 4.24(4H,br s), 8.57(1H,d,J=1.5 Hz), 8.72(1H,d,J=1.5 Hz), 9.60(1H,d,J=6.6 Hz).

Example 22

N-(Diaminophosphinyl)-5-methoxy-2-thiophenecarboxamide mp 200°–216° C.

Elemental Analysis for $C_6H_{10}N_3O_3SP$

Calcd: C, 30.64; H, 4.29; N, 17.87. Found: C, ;30.77 H, 4.17; N, 18.04. $^1$H-NMR (DMSO-$d_6$) δ: 3.90(3H,s), 4.14 (4H,br s), 6.35(1H,d,J=4.2 Hz), 7.86(1H,d,J=4.2 Hz), 9.25 (1H,br s).

Example 23

N-(Diaminophosphinyl)-3-cyano-2-thiophenecarboxamide mp 211°–219° C.

Elemental Analysis for $C_6H_7N_4O_2SP$

Calcd: C, 31.31; H, 3.07; N, 24.34. Found: C, 31.27; H, 3.21; N, 23.99. $^1$H-NMR (DMSO-$d_6$) δ: 4.29(4H,br s), 7.57(1H,d,J=5.2 Hz), 7.98(1H,d,J=5.2 Hz), 9.49(1H,br s).

Example 24

N-(Diaminophosphinyl)-4-methoxy-2-thiophenecarboxamide mp 206°–215° C.

Elemental Analysis for $C_6H_{10}N_3O_3SP$

Calcd: C, 30.64; H, 4.29; N, 17.87. Found: C, 30.65; H, 4.42; N, 17.70. $^1$H-NMR (DMSO-$d_6$) δ: 3.75(3H,s), 4.20 (4H,br s), 6.91(1H,d,J=1.8 Hz), 7.82(1H,d,J=1.8 Hz), 9.44 (1H,d,J=7.0 Hz).

Example 25

N-(Diaminophosphinyl)-2,5-dichloro-3-thiophenecarboxamide mp 168°–172° C.

Elemental Analysis for $C_5H_6N_3O_2SCl_2P$

Calcd: C, 21.91; H, 2.21; N, 15.33. Found: C, 21.81; H, 2.38; N, 15.44. $^1$H-NMR (DMSO-d$_6$) δ: 4.19(4H,br s), 7.51(1H,s), 9.15(1H,br s).

Example 26

N-(Diaminophosphinyl)-2-bromo-3-thiophenecarboxamide mp 160°–162° C.

Elemental Analysis for $C_5H_7N_3O_2SBrP$

Calcd: C, 21.14; H, 2.48; N, 14.79. Found: C, 21.19; H, 2.53; N, 14.86. $^1$H-NMR (DMSO-d$_6$) δ: 4.17(4H,br s), 7.45(1H,d,J=5.0 Hz), 7.60(1H,d,J=5.0 Hz), 9.11(1H,m).

Example 27

N-(Diaminophosphinyl)-3-ethyl-2-thiophenecarboxamide mp 130°–135° C.

Elemental Analysis for $C_7H_{12}N_3O_2SP$

Calcd: C, 36.05; H, 5.19; N, 18.02. Found: C, 35.80; H, 5.17; N, 17.81. $^1$H-NMR (DMSO-d$_6$) δ: 1.16(3H,t,J=7.0 Hz), 2.89(2H,q,J=7.0 Hz), 4.15(4H,br s), 7.05(1H,d,J=5.0 Hz), 7.63(1H,d,J=5.0 Hz), 8.65(1H,br d,J=9.0 Hz).

Example 28

N-(Diaminophosphinyl)-4-methyl-2-thiophenecarboxamide mp 160°–163° C.

Elemental Analysis for $C_6H_{10}N_3O_2SP$

Calcd: C, 32.88; H, 4.60; N, 19.17. Found: C, 32.73; H, 4.60; N, 18.76. $^1$H-NMR (DMSO-d$_6$) δ: 2.21(3H,s), 4.14(4H,br s), 7.40(1H,s), 7.89(1H,s), 9.30(1H,br m).

Example 29

N-(Diaminophosphinyl)-5-bromo-4-methyl-2-thiophenecarboxamide mp 170°–175° C.

Elemental Analysis for $C_6H_9N_3O_2SBrP$

Calcd: C, 24.18; H, 3.04 ; N, 14.10. Found: C, 24.39; H, 3.13; N, 14.22. $^1$H-NMR (DMSO-d$_6$) δ: 2.14(3H,s), 4.19 (4H,br s), 7.89(1H,s), 9.44(1H,br m).

Example 30

N-(Diaminophosphinyl)-5-chloro-3-thiophenecarboxamide mp 177°–184° C.

Elemental Analysis for $C_5H_7N_3O_2SClP$

Calcd: C, 25.06; H, 2.94; N, 17.54. Found: C, 25.08; H, 3.08; N, 17.64. $^1$H-NMR (DMSO-d$_6$) δ: 4.17(4H,br s), 7.59(1H,d,J=1.0 Hz), 8.31(1H,d,J=1.0 Hz), 9.30(1H,d,J=6.8 Hz).

Example 31

N-(Diaminophosphinyl)-5-difluoromethyl-3-thiophenecarboxamide mp 149°–153° C.

Elemental Analysis for $C_6H_8N_3O_2SF_2P$

Calcd: C, 28.24; H, 3.16; N, 16.47. Found: C, 28.19; H, 3.11; N, 16.42. $^1$H-NMR (DMSO-d$_6$) δ: 4.17(4H,br s), 7.31(1H,t,J=55 Hz), 7.90(1H,s), 8.65(1H,s), 9.38(1H,d,J=6.6 Hz).

Example 32

N-(Diaminophosphinyl)-2,5-dimethyl-3-thiophenecarboxamide mp 159°–162° C.

Elemental Analysis for $C_7H_{12}N_3O_2SP$

Calcd: C, 36.05; H, 5.19; N, 18.02. Found: C, 35.90; Hr 5.04; N, 17.75. $^1$H-NMR (DMSO-d$_6$) δ: 2.34(3H,s), 2.57 (3H,s), 4.08(4H,br s), 7.19(1H,s), 8.76(1H,br d,J=7.0 Hz).

Example 33

N-(Diaminophosphinyl)-5-chloro-2-methyl-3-thiophenecarboxamide mp 218°–225° C.

Elemental Analysis for $C_6H_9N_3O_2SClP$

Calcd: C, 28.41; H, 3.58; N, 16.57. Found: C, 28.13; H, 3.58; N, 16.68. $^1$H-NMR (DMSO-d$_6$) δ: 2.60(3H,s), 4.13 (4H,br s), 7.54(1H,s), 9.01(1H,br s).

Example 34

N-(Diaminophosphinyl)-4-chloro-5-methyl-2-thiophenecarboxamide mp 225°–233° C.

Elemental Analysis for $C_6H_9N_3O_2SClP$

Calcd: C, 28.41; H, 3.58; N, 16.57. Found: C, 28.58; H, 3.72; N, 16.69. $^1$H-NMR (DMSO-d$_6$) δ: 2.39(3H,s), 4.19 (4H,br s), 8.02(1H,s), 9.44(1H,br s).

Example 35

N-(Diaminophosphinyl)-5-chloro-4-methyl-2-thiophenecarboxamide mp 182°–184° C.

Elemental Analysis for $C_6H_9N_3O_2SClP$

Calcd: C, 28.41; H, 3.58; N, 16.57. Found: C, 28.02; H, 3.54; N, 16.47. $^1$H-NMR (DMSO-d$_6$) δ: 2.15(3H,s), 4.19 (4H,br s), 7.92(1H,s), 9.19(1H,br s).

Example 36

N-(Diaminophosphinyl)-4,5-dichloro-2-thiophenecarboxamide mp 276°–278° C.

Elemental Analysis for $C_5H_6N_3O_2SCl_2P$

Calcd: C, 21.91; H, 2.21; N, 15.33. Found: C, 22.08; H, 2.29; N, 15.45. $^1$H-NMR (DMSO-d$_6$) δ: 4.26(4H,br s), 8.16(1H,s), 9.43(1H,br s).

Example 37

N-(Diaminophosphinyl)-4-bromo-3-thiophenecarboxamide mp. 149°–153° C.

Elemental Analysis for $C_5H_7N_3O_2SBrP$

Calcd: C, 21.14; H, 2.48; N, 14.79. Found: C, 21.40; H, 2.56; N, 14.42. $^1$H-NMR (DMSO-d$_6$) δ: 4.18(4H,br s), 7.72(1H,m), 8.28(1H,m), 9.29(1H,br m).

Example 38

N-(Diaminophosphinyl)-2-chloro-3-thiophenecarboxamide mp 153°–155° C.

Elemental Analysis for $C_5H_7N_3O_2SClP·¼H_2O$

Calcd: C, 24.60; H, 3.10; N, 17.21. Found: C, 24.70; H, 3.21; N, 17.04. $^1$H-NMR (DMSO-d$_6$) δ: 4.17(4H,br s), 7.40–7.50(2H,m), 9.03(1H,br s).

Example 39

N-(Diaminophosphinyl)-5-bromo-2-furancarboxamide

5-Bromo-2-furancarboxamide (5.0 g) was suspended in toluene (30 ml), and phosphorus pentachloride (5.8 g) was added portionwise. The mixture was stirred at 70° C. for 30 minutes and then cooled to room temperature. Formic acid (1.2 g) was added dropwise, and the mixture was stirred at room temperature for 30 minutes. Precipitated crystals were collected by filtration, washed with toluene and hexane, and dried to give 7.9 g of crystals. The crystals were dissolved in tetrahydrofuran (150 ml), and ammonia gas was introduced under ice-cooling for 30 minutes. The mixture was stirred at room temperature for 1 hour, and precipitate was collected by filtration, washed with water and dried. The obtained solid was recrystallized from methanol to give N-(diaminophosphinyl)-5-bromo-2-furancarboxamide (2.0 g) as colorless crystals.
mp 175°–176° C.
Elemental Analysis for $C_5H_7N_3O_3SBrP$
Calcd ; C, 22.41; H, 2.63; N, 15.68. Found: C, 22.44; H, 2.76; N, 15.71. $^1$H-NMR (DMSO-$d_6$) δ: 4.22(4H,s), 6.77 (1H,d,J=3.6 Hz), 7.55(1H,d,J=3.6Hz), 9.28(1H,d,J=5.8 Hz).

Example 40

N-(Diaminophosphinyl)-2-methyl-3-furancarboxamide

2-Methyl-3-furancarboxamide (2.0 g) was suspended in toluene (30 ml), and phosphorus pentachloride (3.5 g) was added portionwise. The mixture was stirred at 70° C. for 30 minutes, and then cooled to room temperature. Formic acid (0.74 g) was added dropwise, and the mixture was stirred at room temperature for 30 minutes. Hexane (20 ml) was added, and the resulting mixture was stirred for 10 minutes. Precipitated crystals were collected by filtration, washed with hexane and dried to give 3.3 g of crystals. The crystals were dissolved in tetrahydrofuran (100 ml), and ammonia gas was introduced under ice-cooling for 30 minutes. The mixture was stirred at room temperature for 1 hour, and diethyl ether (100 ml) was added. The resulting mixture was stirred for 10 minutes, and precipitate was collected by filtration, washed with water and dried. The obtained solid was recrystallized from methanol to give N-(diaminophosphinyl)-2-methyl-3-furancarboxamide (0.85 g) as colorless crystals.
mp 249°–253° C. (decomp.).
Elemental Analysis for $C_6H_{10}N_3O_3P$
Calcd: C, 35.48; H, 4.96; N, 20.69. Found: C, 35.41; H, 4.86; N, 20.68. $^1$H-NMR (DMSO-$d_6$) δ: 2.52(3H,s), 4.13 (4H,s), 7.17(1H,d,J=2.0 Hz), 7.50(1H,d,J=2.0 Hz), 9.00(1H, d,J=7.4 Hz).

Example 41

N-(Diaminophosphinyl)-5-bromo-3-furancarboxamide

5-Bromo-3-furancarboxamide (2.0 g) was suspended in toluene (30 ml), and phosphorus pentachloride (2.3 g) was added portionwise. The mixture was stirred at 70° C. for 30 minutes, and then cooled to room temperature. Formic acid (0.48 g) was added dropwise, and the mixture was stirred at room temperature for 30 minutes. Hexane (20 ml) was added, and the mixture was stirred for 10 minutes. Precipitatated crystals were collected by filtration, washed with hexane and dried to give 2.3 g of crystals. The crystals were dissolved in tetrahydrofuran (100 ml), and ammonia gas was introduced under ice-cooling for 30 minutes. The resulting mixture was stirred at room temperature for 1 hour, and precipitate was collected by filtration, washed with water and dried. The obtained solid was recrystallized from methanol to give N-(diaminophosphinyl)-5-bromo-3-furancarboxamide (1.0 g) as colorless crystals.
mp 181°–183° C.
Elemental Analysis for $C_5H_7N_3O_3BrP$
Calcd: C, 22.41; H, 2.63; N, 15.68. Found: C, 22.46; H, 2.40; N, 15.76. $^1$H-NMR (DMSO-$d_6$) δ: 4.18(4H,s), 7.03 (1H,d,J=1.0 Hz), 8.46(1H,d,J=1.0 Hz), 9.25(1H,d,J=7.0 Hz).

Examples 42 to 51

The following compounds were synthesized in the same manner as Example 39.

Example 42

N-(Diaminophosphinyl)-5-chloro-2-furancarboxamide mp 242°–244° C.
Elemental Analysis for $C_5H_7N_3O_3ClP$
Calcd: C, 26.86; H, 3.16; N, 18.80. Found: C, 26.82; H, 2.96; N, 18.85. $^1$H-NMR (DMSO-$d_6$) δ: 4.22(4H,d,J=2.6 Hz), 6.68(1H,d,J=3.5 Hz), 7.58(1H,d,J=3.5 Hz), 9.26(1H,d, J=7.0 Hz)

Example 43

N-(Diaminophosphinyl)-5-methyl-2-furancarboxamide mp 281°–285° C. (decomp.).
Elemental Analysis for $C_6H_{10}N_3O_3P$
Calcd: C, 35.48; H, 4.96; N, 20.69. Found: C, 35.56; H, 4.94; N, 20.68. $^1$H-NMR (DMSO-$d_6$) δ: 2.33(3H,s), 4.16 (4H,s), 6.25(1H,d,J=3.0 Hz), 7.37(1H,d,J=3.0 Hz), 8.94(1H, d,J=7.0 Hz).

Example 44

N-(Diaminophosphinyl)-5-ethyl-2-furancarboxamide
mp 151°–153° C.
Elemental Analysis for $C_7H_{12}N_3O_3P\cdot\frac{1}{4}H_2O$
Calcd: C, 37.93; H, 5.68; N, 18.96. Found: C, 37.96; H, 5.56; N, 18.77. $^1$H-NMR (DMSO-$d_6$) δ: 1.20(3H,t,J=7.6 Hz), 2.70(2H,q,J=7.6 Hz), 4.16(4H,s), 6.26(1H,d,J=3.3 Hz), 7.37(1H,d,J=3.3 Hz), 8.91(1H,br s).

Example 45

N-(Diaminophosphinyl)-2-chloro-3-furancarboxamide mp 153°–155° C.
Elemental Analysis for $C_5H_7N_3O_3ClP$
Calcd: C, 26.86; H, 3.16; N, 18.80. Found: C, 27.13; H, 3.14; N, 18.61. $^1$H-NMR (DMSO-$d_6$) δ: 4.20(4H,s), 7.33 (1H,d,J=2.2 Hz), 7.74(1H,d,J=2.2 Hz), 9.14(1H,d,J=7.0 Hz).

Example 46

N-(Diaminophosphinyl)-5-chloro-3-furancarboxamide mp 170°14 171° C.
Elemental Analysis for $C_5H_7N_3OClP$
Calcd: C, 26.86; H, 3.16; N, 18.80. Found: C, 26.76; H, 3.00; N, 18.70. $^1$H-NMR (DMSO-$d_6$) δ: 4.18(4H,s), 6.94 (1H,s), 8.39(1H,s), 9.23(1H,d,J=7.4 Hz).

Example 47

N-(Diaminophosphinyl)-5-difluoromethyl-2-furancarboxamide
mp 156°–158° C.
Elemental Analysis for $C_6H_8N_3O_3F_2P$
  Calcd: C, 30.14; H, 3.37; N, 17.57. Found: C, 30.06; H, 3.14; N, 17.60. $^1$H-NMR (DMSO-$d_6$) δ: 4.23(4H,s), 7.01–7.05(1H,m), 7.15(1H,t,J=53 Hz), 7.57(1H,d,J=3.6 Hz), 9.35(1H,d,J=6.0 Hz).

Example 48

N-(Diaminophosphinyl)-2-trifluoromethyl-5-methyl-3-furancarboxamide
mp 158°–160° C.
Elemental Analysis for $C_7HgN_3O_3F_3P$
  Calcd: C, 31.01; H, 3.35; N, 15.50. Found: C, 31.28; H, 3.40; N, 15.62. $^1$H-NMR (DMSO-$d_6$) δ: 2.35(3H,s), 4.19(4H,s), 6.85(1H,s), 9.37(1H,d,J=6.8 Hz).

Example 49

N-(Diaminophosphinyl)-2,5-dimethyl-2-furancarboxamide
mp 167°–169° C.
Elemental Analysis for $C_7H_{12}N_3O_3P$
  Calcd: C, 38.72; H, 5.57; N, 19.35. Found: C, 38.95; H, 5.33; N, 19.29. $^1$H-NMR (DMSO-$d_6$) δ: 2.20(3H,s), 2.47(3H,s), 4.09(4H,s), 6.71(1H,s), 8.80(1H,br s).

Example 50

N-(Diaminophosphinyl)-5-chloro-2-methyl-3-furancarboxamide
mp 270°–275° C. (decomp.).
Elemental Analysis for $C_6H_9N_3O_3ClP$
  Calcd: C, 30.33; H, 3.82; N, 17.69. Found: C, 30.32; H, 3.96; N, 17.78. $^1$H-NMR (DMSO-$d_6$) δ: 2.52(3H,s), 4.15(4H,s), 7.13(1H,s), 9.04(1H,d,J=7.4 Hz).

Example 51

N-(Diaminophosphinyl)-2-ethyl-3-furancarboxamide
mp 277°–280° C. (decomp.).
Elemental Analysis for $C_7H_{12}N_3O_3P$
  Calcd: C, 38.72; H, 5.57; N, 19.35. Found: C, 38.68; H, 5.67; N, 19.42. $^1$H-NMR (DMSO-$d_6$) δ: 1.15(3H,t,J=7.6 Hz), 2.98(2H,q,J=7.6 Hz), 4.09(4H,s), 7.14(1H,d,J=2.2 Hz), 7.51(1H,d,J=2.2 Hz), 8.90(1H,d,J=7.0 Hz).

Example 52

N-(Diaminophosphinyl)-4-nitrophenoxyacetamide

4-Nitrophenoxyacetamide (3.5 g) was suspended in toluene (30 ml), and phosphorus pentachloride (3.9 g) was added portionwise. The mixture was stirred at 70° C. for 3 hours, and then cooled to room temperature. Formic acid (0.83 g) was added dropwise, and the mixture was stirred at room temperature for 2 hours. Precipitated crystals were collected by filtration, washed with toluene and dried to give 3.5 g of crystals. The crystals were dissolved in tetrahydrofuran (150 ml), and ammonia gas was introduced under ice-cooling for 30 minutes. The mixture was stirred at room temperature for 1 hour, and precipitate was collected by filtration, washed with water and dried. The obtained solid was recrystallized from water to give N-(diaminophosphinyl)-4-nitrophenoxyacetamide (0.5 g) as colorless crystals.
mp 174°–176° C.
Elemental Analysis for $C_8H_{11}N_4O_5P$
  Calcd: C, 35.05; H, 4.04 ; N, 20.43. Found: C, 34.84; H, 3.97; N, 20.14. $^1$H-NMR (DMSO-$d_6$) δ: 4.19(4H,s), 4.79(2H,s), 7.10–7.14(2H,m), 8.18–8.23(2H,m), 9.08(1H,d,J=8.0 Hz).

Example 53 to 81

The following compounds were synthesized in the same manner as Example 52.

Example 53

N-(Diaminophosphinyl)-4-methoxyphenoxyacetamide
mp 154°–156° C.
Elemental Analysis for $C_9H_{14}N_3O_4P$
  Calcd: C, 41.70; H, 5.41; N, 16.21. Found: C, 41.59; H, 5.21; N, 16.14. $^1$H-NMR (DMSO-$d_6$) δ: 3.70(3H,s), 4.16(4H,s), 4.49(2H,s), 6.86(4H,s), 8.75(1H,d,J=8.0 Hz).

Example 54

N-(Diaminophosphinyl)-4-fluorophenoxyacetamide
mp 156°–158° C.
Elemental Analysis for $C_8H_{11}N_3O_3FP$
  Calcd: C, 38.88; H, 4.49; N, 17.00. Found: C, 38.81; H, 4.42; N, 17.01. $^1$H-NMR (DMSO-$d_6$) δ: 4.18(4H,s), 4.56(2H,s), 6.90–6.97(2H,m), 7.07–7.16(2H,m), 8.87(1H,d,J=7.0 Hz).

Example 55

N-(Diaminophosphinyl)-4-chlorophenoxyacetamide
mp 155°–157° C.
Elemental Analysis for $C_8H_{11}N_3O_3ClP$
  Calcd: C, 36.45; H, 4.21; N, 15.94. Found: C, 36.54; H, 4.17; N, 15.72. $^1$H-NMR (DMSO-d6) δ: 4.18(4H,s), 4.59(2H,s), 6.92–6.98(2H,m), 7.31–7.35(2H,m), 8.91(1H,d,J=7.8 Hz).

Example 56

N-(Diaminophosphinyl)-2,3,5-trimethylphenoxyacetamide
mp 171°–173° C.
Elemental Analysis for $C_{11}H_{18}N_3O_3P$
  Calcd: C, 48.71; H, 6.69; N, 15.49. Found: C, 48.54; H, 6.63; N, 15.12. $^1$H-NMR (DMSO-$d_6$) δ: 2.07(3H,s), 2.17(3H,s), 2.21(3H,s), 4.19(4H,s), 4.53(2H,s), 6.48(1H,s), 6.60(1H,s), 8.69(1H,d,J=8.2 Hz).

Example 57

N-(Diaminophosphinyl)-4-cyanophenoxyacetamide
mp 173-178° C.
Elemental Analysis for $C_9H_{11}N_4O_3P$
  Calcd: C, 42.53; H, 4.36; N, 22.04. Found: C, 42.76; H, 4.38; N, 21.97. $^1$H-NMR (DMSO-$d_6$) δ: 4.22(4H,br s), 4.73(2H,s), 7.08(2H,d,J=8.6 Hz), 7.77(2H,d,J=8.6 Hz), 9.06(1H,br s).

Example 58

N-(Diaminophosphinyl)-3-chlorophenoxyacetamide
mp 143°–148° C.
Elemental Analysis for $C_8H_{11}N_3O_3ClP$
  Calcd: C, 36.45; H, 4.21; N, 15.94. Found: C, 36.12; H, 4.30; N, 16.08. $^1$H-NMR (DMSO-$d_6$) δ: 4.21(4H,br s), 4.63(2H,s), 6.87–6.93(1H,m), 6.99–7.03(2H,m), 7.33(1H,d, J=8.4 Hz), 8.93(1H,br s).

Example 59

N-(Diaminophosphinyl)-2-chlorophenoxyacetamide
mp 141°–148° C.
Elemental Analysis for $C_8H_{11}N_3O_3ClP\cdot\frac{1}{4}H_2O$
Calcd: C, 35.84; H, 4.32; N, 15.67. Found: C, 35.44; H, 4.15; N, 16.03. $^1$H-NMR (DMSO-$d_6$) δ: 4.21(4H,br s), 4.71(2H,s), 6.97–7.01(2H,m), 7.23–7.32(1H,m), 7.41–7.46 (1H,m), 8.84(1H,br s).

Example 60

N-(Diaminophosphinyl)-3-fluorophenoxyacetamide
mp 144°–149° C.
Elemental Analysis for $C_8H_{11}N_3O_3FP$
Calcd: C, 38.88; H, 4.49; N, 17.00. Found: C, 38.97; H, 4.58; N, 17.04. $^1$H-NMR (DMSO-$d_6$) δ: 4.22(4H,br s), 4.62(2H,s), 6.74–6.82(3H,m), 7.26–7.38(1H,m), 8.95(1H,d, J=8.4 Hz).

Example 61

N-(Diaminophosphinyl)-phenylthioacetamide
mp 156°–162° C.
Elemental Analysis for $C_8H_{12}N_3O_2SP$
Calcd: C, 39.18; H, 4.93; N, 17.13. Found: C, 39.30; H, 4.97; N, 17.21. $^1$H-NMR (DMSO-$d_6$) δ: 3.76(2H,s), 4.13 (4H,br s), 7.17–7.46(5H,m), 9.15(1H,br s).

Example 62

N-(Diaminophosphinyl)-4-fluorophenylthioacetamide
mp 155°–160° C.
Elemental Analysis for $C_8H_{11}N_3O_2SFP$
Calcd: C, 36.50; H, 4.21; N, 15.96. Found: C, 36.42; H, 3.96; N, 15.98. $^1$H-NMR (DMSO-$d_6$) δ: 3.71(2H,s), 4.12 (4H,br s), 7.15(1H,d,J=8.8 Hz), 7.19(1H,d,J=9.0 Hz), 7.42 (1H,dd,J=9.0 Hz & 5.4 Hz), 7.44(1H,dd,J=8.8 Hz & 5.2 Hz), 9.11(1H,br s).

Example 63

N-(Diaminophosphinyl)-2-benzoxazolylthioacetamide
mp 160°–164° C.
Elemental Analysis for $C_9H_{11}N_4O_3SP$
Calcd: C, 37.76; H, 3.87; N, 19.57. Found: C, 37.63; H, 3.78; N, 19.48. $^1$H-NMR (DMSO-$d_6$) δ: 4.16(4H,br s), 4.27(2H,s), 7.30–7.37(2H,m), 7.61–7.66(2H,m), 9.34(1H,br s).

Example 64

N-(Diaminophosphinyl)-2-benzothiazolylthioacetamide
mp 166°–170° C.
Elemental Analysis for $C_9H_{11}N_4O_2S_2P$
Calcd: C, 35.76; H, 3.67; N, 18.53. Found: C, 35.75; H, 3.77; N, 18.58. $^1$H-NMR (DMSO-$d_6$) δ: 4.17(4H,br s), 4.28(2H,s), 7.34–7.53(2H,m), 7.84–7.88(1H,m), 8.01–8.05 (1H,m), 9.35(1H,br s).

Example 65

N-(Diaminophosphinyl)-5-chloro-2-benzothiazolylthioacetamide
mp 165°–171° C.
Elemental Analysis for $C_9H_{10}N_4O_2S_2ClP$
Calcd: C, 32.10; H, 2.99; N, 16.64. Found: C, 32.18; H, 2.94; N, 16.58. $^1$H-NMR (DMSO-$d_6$) δ: 4.19(4H,br s), 4.29(2H,s), 7.44(1H,dd,J=8.6 Hz & 2.0 Hz), 7.94(1H,d,J= 2.0 Hz), 8.07(1H,d,J=8.6 Hz), 9.38(1H,br s).

Example 66

N-(Diaminophosphinyl)-5-ethoxy-2-benzothiazolylthioacetamide
mp 169°–174° C.
Elemental Analysis for $C_{11}H_{15}N_4O_3S_2P$—$H_2O$
Calcd.: C, 36.25; H, 4.70; N, 15.38. Found: C, 36.20; H, 4.54; N, 15.78. $^1$H-NMR (DMSO-$d_6$) δ: 1.33(1H,t,J=7.0 Hz), 4.04(2H,q,J=7.0 Hz), 4.16(4H,br s), 7.02(1H,dd,J=9.0 Hz & 2.6 Hz), 7.56(1H,d,J=2.6 Hz), 7.71(1H,d,J=9.0 Hz), 8.32(1H,br s).

Example 67

N-(Diaminophosphinyl)-2-benzofurancarboxamide
mp 172°–174° C.
Elemental Analysis for $C_9H_{10}N_3O_3P$
Calcd.: C, 45.20; H, 4.21; N, 17.57. Found: C, 45.05; H, 4.24; N, 17.50. $^1$H-NMR (DMSO-$d_6$) δ: 4.27(4H,s), 7.34 (1H,t,J=7.4 Hz), 7.68(1H,d,J=8.4 Hz), 7.79(1H,d,J=7.6 Hz), 7.84(1H,t,J=7.0 Hz), 7.90(1H,s), 9.40(1H,d,J=7.0 Hz).

Example 68

N-(Diaminophosphinyl)-2-methyl-5-benzoxazolecarboxamide
mp 250° C. (decomp.).
Elemental Analysis for $C_9H_{11}N_4O_3P$—$H_2O$
Calcd: C, 39.71; H, 4.81; N, 20.58. Found: C, 39.48; H, 4.09; N, 20.45. $^1$H-NMR (DMSO-$d_6$) δ: 2.66(3H,s), 4.19 (4H,br s), 7.68(2H,d,J=9.0 Hz), 8.03(1H,dd,J=9.0 Hz&2.0 Hz), 8.34(1H,d,J=2.0 Hz), 9.52(1H,br d,J=7.0 Hz).

Example 69

N-(Diaminophosphinyl)-3-(2-benzoxazolyl)propenamide
mp 180° C. (decomp.).
Elemental Analysis for $C_{10}H_{11}N_4O_3P$
Calcd: C, 45.12; H, 4.17; N, 21.05. Found: C, 45.00; H, 3.98; N, 20.97. $^1$H-NMR (DMSO-$d_6$) δ: 4.24(4H,br s), 7.35–7.52(4H,m), 7.74–7.83(2H,m), 9.61(1H,d,J=6.0 Hz).

Example 70

N-(Diaminophosphinyl)-2-benzothiazolecarboxamide
mp 169°–174° C.
Elemental Analysis for $C_8H_9N_4O_2SP$
Calcd: C, 37.50; H, 3.54; N, 21.87. Found: C, 37.42; H, 3.38; N, 21.86. $^1$H-NMR (DMSO-$d_6$) δ: 4.44(4H,br s), 7.61–7.67(2H,m), 8.17–8.28(2H,m), 8.90(1H,br s).

Example 71

N-(Diaminophosphinyl)-3-chloro-6-methylbenzothiophenecarboxamide
mp 173°–178° C.
Elemental Analysis for $C_{10}H_{11}N_3O_2SClP\cdot\frac{1}{5}CH_3OH$
Calcd: C, 39.51; H, 3.71; N, 13.55. Found: C, 39.30; H, 3.64; N, 13.15. $^1$H-NMR (DMSO-$d_6$) δ: 2.48(3H,s), 4.39 (4H,br s), 7.43(1H,dd,J=8.2 Hz&1.0 Hz), 7.81(1H,d,J=8.2 Hz), 7.92(1H,s), 8.38(1H,br s).

Example 72

N-(Diaminophosphinyl)-3-(5-chloro-2-benzoxazolyl)propenamide
mp 210°–211° C. (decomp.).
Elemental Analysis for $C_{10}H_{10}N_4O_3ClP$ Calcd: C, 39.95; H, 3.35; N, 18.64. Found: C, 39.79; H, 3.42; N, 18.49. $^1$H-NMR (DMSO-$d_6$) δ: 4.23(4H,br d,J=2.0 Hz), 7.35(2H,m), 7.52(1H,dd,J=9.0 Hz&2.0 Hz), 7.83(1H, d,J=9.0 Hz), 7.93(1H,d,J=2.0 Hz), 9.55(1H,br m).

Example 73

N-(Diaminophosphinyl)-5-methyl-3-phenyl-4-isoxazolecarboxamide
mp 230° C. (decomp.).
Elemental Analysis for $C_{11}H_{13}N_4O_3P \cdot 0.2H_2O$
 Calcd: C, 46.55; H, 4.76; N, 19.74. Found: C, 46.42; H, 4.78; N, 20.10. $^1$H-NMR (DMSO-$d_6$) δ: 2.56(3H,s), 4.24 (4H,br s), 7.49(3H,m), 7.70(2H,m), 9.34(1H,br m).

Example 74

N-(Diaminophosphinyl)-3-chloro-2-benzothiophenecarboxamide
mp 261°–271° C.
Elemental Analysis for $C_9H_9N_3O_2SClP$
 Calcd: C, 37.27; H, 3.13; N, 14.51. Found: C, 36.92; H, 3.18; N, 14.59. $^1$H-NMR (DMSO-$d_6$) δ: 4.38(4H,br s), 7.56–7.64(2H,m), 7.88–7.93(1H,m), 8.09–8.13(1H,m), 8.68 (1H,br s).

Example 75

N-(Diaminophosphinyl)-3-benzisoxazolylacetamide
mp 157°–164° C.
Elemental Analysis for $C_9H_{11}N_4O_3P$
 Calcd: C, 42.53; H, 4.36; N, 22.04. Found: C, 42.30; H, 4.31; N, 21.49. $^1$H-NMR (DMSO-$d_6$) δ: 4.06(2H,s), 4.15 (4H,br s), 7.38(1H,m), 7.67(2H,m), 7.87(1H,d,J=8.0 Hz), 9.43(1H,br m).

Example 76

N-(Diaminophosphinyl)-N'-(4-methylbenzenesulfonyl)glycinamide
mp 161°–169° C.
Elemental Analysis for $C_9H_{15}N_4O_4SP \cdot \frac{1}{10}H_2O$
 Calcd: C, 35.09; H, 4.97; N, 18.19. Found: C, 34.76; H, 4.94; N, 18.10. $^1$H-NMR (DMSO-$d_6$) δ: 2.38(3H,s), 3.52 (2H,s), 4.08(4H,br s), 7.39(2H,d,J=8.0 Hz), 7.68(2H,d,J=8.0 Hz), 7.77(1H,br s), 8.77(1H,br s).

Example 77

N-(Diaminophosphinyl)-3-(4-bromo-2-thienyl)propenamide
mp 176°–184° C.
Elemental Analysis for $C_7H_9N_3O_2BrP$
 Calcd: C, 27.11; H, 2.93; N, 13.55. Found: C, 26.91; H, 2.86; N, 13.71. $^1$H-NMR (DMSO-$d_6$) δ: 4.16(4H,br s), 6.59(1H,d,J=15.7 Hz), 7.47(1H,s), 7.63(1H,d,J=15.7 Hz), 7.76(1H,s), 9.14(1H,d,J=7.4 Hz).

Example 78

N-(Diaminophosphinyl)-3-(2-thienyl)propenamide
mp 173°–177° C.
Elemental Analysis for $C_7H_{10}N_3O_2SP$
 Calcd: C, 36.36; H, 4.36; N, 18.17. Found: C, 36.16; H, 4.21; N, 18.16. $^1$H-NMR (DMSO-$d_6$) δ: 4.08(4H,br s), 6.55(1H,d,J=15.6 Hz), 7.13(1H,dd,J=5.0 Hz&3.6 Hz), 7.43 (1H,d,J=3.6 Hz), 7.60(1H,d,J=5.0 Hz), 7.67(1H,d,J=15.6 Hz), 9.06(1H,br s).

Example 79

N-(Diaminophosphinyl)-2-cyano-3-(2-thienyl)propenamide
mp 190°–196° C.
Elemental Analysis for $C_8H_9N_4O_2SP$
 Calcd: C, 37.50; H, 3.54; N, 21.87. Found: C, 37.14; H, 3.56; N, 21.78. $^1$H-NMR (DMSO-$d_6$) δ: 4.26(4H, br s), 7.32–7.37(1H,m), 7.85(1H,d,J=4.3 Hz), 8.15(1H,d,J=4.3 Hz), 8.61(1H,s), 9.08(1H,br s).

Example 80

N-(Diaminophosphinyl)-2-thienylacetamide
mp 179°–184° C.
Elemental Analysis for $C_6H_{10}N_3O_2SP$
 Calcd: C, 32.88; H, 4.60; N, 19.17. Found: C, 32.81; H, 4.48; N, 19.14. $^1$H-NMR (DMSO-$d_6$) δ: 3.77(2H,s), 4.11 (4H,br s), 6.93–6.99(2H,m), 7.38(1H,dd,J=5.0 Hz&1.4 Hz), 9.16(1H,br s).

Example 81

N-(Diaminophosphinyl)-3-thienylacetamide
mp 174°–181° C.
Elemental Analysis for $C_6H_{10}N_3O_2SP$
 Calcd: C, 32.88; H, 4.60; N, 19.17. Found: C, 32.55; H, 4.50; N, 18.92. $^1$H-NMR (DMSO-$d_6$) δ: 3.54(2H,s), 4.08 (4H,br s), 7.04(1H,d,J=4.8 Hz), 7.27(1H,d,J=2.8 Hz), 7.46 (1H,dd,J=4.8 Hz&2.8 Hz), 9.12(1H,br s).

Example 82

N-(Diaminophosphinyl)-3-(2-benzoxazolyl)propionamide

N-(Diaminophosphinyl)-3-(2-benzoxazolyl)prop enamide (0.25 g) was dissolved in methanol (30 ml) with heating, and 10% Pd—C (wet) (0.05 g) was added. The mixture was hydrogenated at room temaperature under atmospheric pressure for 1 hour. The catalyst was removed by filtration, and the filtrate was concentrated under reduced pressure. Precipitated crystals were collected by filtration to give N-(diaminophosphinyl)-3-(2-benzoxazolyl)propinonamide (0.17 g) as colorless crystals.
mp 176°–178° C. (decomp.).
Elemental Analysis for $C_{10}H_{13}N_4O_3P$
 Calcd: C, 44.78; H, 4.89; N, 20.89. Found: C, 44.71; H,4.90 ; N, 20.82. $^1$H-NMR (DMSO-$d_6$) δ: 2.83(2H,m), 3.13(2H,m), 4.00(4H,br s), 7.35(2H,m), 7.67(2H,m), 9.05 (1H,m).

Example 83

N-(Diaminophosphinyl)-1-benzimidazolylacetamide

A mixture of benzimidazole (10 g), ethyl bromoacetate (15.5 g), potassium carbonate (12.9 g) and N,N-dimethylformamide (50 ml) was stirred at 50° C. for 15 hours. The mixture was poured into water and extracted with diethyl ether. The extract was washed with water and saturated aqueous sodium chloride, dried over anhydrous magnesium sulfate and concentrated under reduced pressure. The residue was purified by silica gel column chromatography to give ethyl 1-benzimidazolylacetate (12 g) as oil. Ethyl 1-benzimidazolylacetate (12 g) was dissolved in ethanol (200 ml), and ammonia gas was introduced under ice-cooling for 30 minutes. The mixture was stirred at room temperature for 65 hours. Precipitated crystals were collected by filtration, washed with ethanol to give 1-benzimidazolylacetamide (4.3 g) as colorless crystals.
mp 204°–205° C.
 1-Benzimidazolylacetamide (2.0 g) was suspended in toluene (30 ml), and phosphorus pentachloride (2.5 g) was added portionwise. The mixture was stirred at 70° C. for 1 hour and then cooled to room temperature. Formic acid (0.52 g) was added dropwise, and then tetrahydrofuran (30 ml) was added. The mixture was stirred at room temperature for 1 hour. Precipitate was collected by filtration, washed with toluene and hexane, and dried to give powder. The powder was suspended in tetrahydrofuran (150 ml) and ammonia gas was introduced under ice-cooling for 50 minutes. The mixture was stirred at room temperature for 1 hour. Diethyl ether was added and precipitate was collected by filtration, washed with diethyl ether. The obtained solid was purified by column chromatography on XAD-II using water as an eluent. The desired fractions were concentrated under reduced pressure and the residue was crystallized from ethanol. The crystals were recrystallized form water-ethanol to give N-(diaminophosphinyl)-1-benzimidazolylacetamide (0.19 g) as colorless crystals.
mp 186°–188° C.
Elemental analysis for $C_9H_{12}N_5O_2P\cdot\frac{1}{4}H_2O$
 Calcd: C, 41.95; H, 4.89; N, 27.18. Found: C, 42.14; H, 4.84; N, 26.99. $^1$H-NMR (DMSO-$d_6$) δ: 4.17(4H,s), 5.04 (2H,s), 7.16–7.29(2H,m), 7.43–7.47(1H,m), 7.63–7.67(1H, m), 8.15(1H,s), 9.32(1H,s).

Examples 84 to 91

The following compounds were synthesized in the same manner as Example 1.

Example 84

N-(Diaminophosphinyl)-4-chloro-2-thiophenecarboxamide
mp 278°–280° C.
Elemental analysis for $C_5H_7N_3O_2SClP$
 Calcd: C, 25.06; H, 2.94; N, 17.54. Found: C, 24.95; H, 2.87; N, 17.57. $^1$H-NMR (DMSO-$d_6$) δ: 4.23(4H,br s), 7.86(1H,d,J=1.4 Hz), 8.11(1H,d,J=1.4 Hz), 9.51(1H, br s).

Example 85

N-(Diaminophosphinyl)-4-methyl-3-thiophenecarboxamide
mp 145°–147° C.
Elemental analysis for $C_6H_{10}N_3O_2SP\cdot\frac{1}{4}H_2O$
 Calcd: C, 31.94; H, 4.88; N, 18.64. Found: C, 32.21; H, 4.73; N, 18.78. $^1$H-NMR (DMSO-$d_6$) δ: 2.36(3H,s), 4.13 (4H,br s), 7.19(1H,d,J=3.2 Hz), 8.32(1H,d,J=3.2Hz), 9.12 (1H,br s).

Example 86

N-(Diaminophosphinyl)-5-bromo-2-chloro-3-thiophenecarboxamide
mp 181°–183° C.
Elemental analysis for $C_5H_6N_3O_2SBrClP$
 Calcd: C, 18.95; H, 1.90; N, 13.19. Found: C, 19.05; H, 1.91; N, 13.37. $^1$H-NMR (DMSO-$d_6$) δ: 4.19(4H,br s), 7.16(1H,s), 9.15(1H,br s).

Example 87

N-(Diaminophosphinyl)-5-chloro-4-methyl-3-thiophenecarboxamide
mp 159°–161° C.
Elemental analysis for $C_6H_9N_3O_2SClP\cdot\frac{1}{4}H_2O$
 Calcd: C, 27.91; H, 3.71; N, 16.28. Found: C, 27.82; H, 3.57; N, 16.24. $^1$H-NMR (DMSO-$d_6$) δ: 2.29(3H,s), 4.14 (4H,br s), 7.18(1H,s), 8.92(1H,br s).

Example 88

N-(Diaminophosphinyl)-2,5-dichloro-4-methyl-3-thiophenecarboxamide
mp 178°–180° C.
Elemental analysis for $C_6H_8N_3O_2SCl_2P$
 Calcd: C, 25.01; H, 2.80; N, 14.59. Found: C, 24.89; H, 2.81; N, 14.62. $^1$H-NMR (DMSO-$d_6$) δ: 2.12(3H,s), 4.21 (4H,br s), 9.42(1H,br s).

Example 89

N-(Diaminophosphinyl)-2-chloro-5-methyl-3-thiophenecarboxamide
mp 180°–183° C.
Elemental analysis for $C_6H_9N_3O_2SClP$
 Calcd: C, 28.41; H, 3.58; N, 16.57. Found: C, 28.34; H, 3.39; N, 16.64. $^1$H-NMR (DMSO-$d_6$) δ: 2.38(3H,s), 4.17 (4H,br s), 7.16(1H,s), 8.92(1H,br s).

Example 90

N-(Diaminophosphinyl)-3-chloro-4-methyl-2-thiophenecarboxamide
mp 288°–291° C.
Elemental analysis for $C_6H_9N_3O_2SClP$
 Calcd: C, 28.41; H, 3.58; N, 16.57. Found: C, 28.35; H, 3.45; N, 16.57. $^1$H-NMR (DMSO-$d_6$) δ: 2.18(3H,d,J=0.8 Hz), 4.31(4H,br s), 7.65(1H,q,J=0.8 Hz), 8.37(1H,d,J=6.6 Hz).

Example 91

N-(Diaminophosphinyl)-3,5-dimethyl-2-thiophenecarboxamide
mp 160°–162° C.
Elemental analysis for $C_7H_{12}N_3O_2SP$
 Calcd: C, 36.05; Hr 5.19; N, 18.02. Found: C, 35.86; H, 5.16; N, 17.97. $^1$H-NMR (DMSO-$d_6$) δ: 2.37(3H,s), 2.41 (3H,s), 4.13(4H,br s), 6.68(1H,s), 8.37(1H,d,J=6.6 Hz).

Example 92

The following compound was synthesized in the same manner as Example 39.

N-(Diaminophosphinyl)-3-methyl-2-furancarboxamide
mp 157°–1058° C.
Elemental analysis for $C_6H_{10}N_3O_3P\cdot\frac{1}{4}H_2O$
 Calcd: C, 34.71; H, 5.10; N, 20.24. Found: C, 34.75; H, 5.09; N, 20.38. $^1$H-NMR (DMSO-$d_6$) δ: 2.30(3H,s), 4.16 (4H,br s), 6.53(1H,d,J=1.4 Hz), 7.70(1H,d,J=1.4 Hz), 8.31 (1H,br s).

Experimental Example 1

Bacteria Eradication Effect of Flurofamide

To 5-week-aged male Crj:ICR mice previously fasted for 30 hours, *Helicobacter pylori* CPY 433 F4 was inoculated intragastrically at $10^7$ CFU per mouse. One week after the infection, a test compound which was suspended in 0.5% methylcellulose containing 1% sodium bicarbonate was orally administered at 100 mg/kg twice daily for 7 days. On the next day after the final administration, the stomach of the infected mouse was excised and homogenated. A series of 10-fold dilutions were inoculated to modified Skirrow medium supplemented with activated charcoal and incubated at 37° C. for 4 days under slightly aerobic conditions. The bacteria eradication effect was determined by investigating whether bacterial growth was seen or not. The results are shown in Table 3.

TABLE 3

| Compound | Eradication Rate |
| --- | --- |
| Flurofamide (Ref. Ex. 1) | 4/5* |
| Control# | 0/4 |

0.5% methylcellulose containing 1% sodium bicarbonate
*p <0.05 ($\chi^2$-test)

Experimental Example 2
Bacteria Eradication Effect of Urease Inhibitor (in vivo)

To 5 male ICR mice, a bacterial suspension (1 ml) containing $1\times10^7$ CFU *Helicobacter pylori* (CPY-433 F4) was orally administered to cause infection. Starting at 10 days after the bacterial inoculation, a test compound (10 mg/kg), which was suspended in 0.5% methylcellulose solution containing 1% NaHCO$_3$, was orally administered twice daily for 2, 3 or 4 days. Separately, lansoprazole (30 mg/kg), which was suspended in 0.5% methylcellulose solution, was subcutaneously administered 10 minutes before the first administration on each day. On the next day after the final dministration, mice were sacrificed and stomachs were excised, washed with physiological saline (5 ml) and homogenized in Brucella medium (2 ml). A series of 10-fold dilutions of the gastric homogenate in Brucella medium (0.1 ml) were spread over a modified Brucella agar medium and incubated at 37° C. for 4 days under microaerobic conditions, and the CFU per stomach was determined. The results were shown in Table 4.

TABLE 4

| Compound | Eradication Rate | Days for therapy |
| --- | --- | --- |
| Flurofamide (Ref. Ex. 1) | 0/5–3/5 | 4 |
| Example 2 | 2/5 | 4 |
| Example 3 | 2/5 | 4 |
| Example 5 | 3/5 | 4 |
| Example 9 | 1/5 | 2 |
| Example 11 | 1/5 | 2 |
| Example 12 | 1/5 | 2 |
| Example 15 | 2/5 | 2 |
| Example 17 | 1/5 | 2 |
| Example 19 | 1/5 | 2 |
| Example 23 | 1/5 | 2 |
| Example 25 | 1/5 | 2 |
| Example 26 | 2/5 | 2 |
| Example 28 | 1/5 | 2 |
| Example 30 | 1/5 | 2 |
| Example 32 | 2/5 | 2 |
| Example 40 | 1/5 | 2 |
| Example 41 | 1/5 | 2 |
| Example 44 | 1/5 | 2 |
| Example 45 | 1/5 | 2 |
| Example 46 | 1/5 | 2 |
| Example 54 | 1/5 | 3 |
| Reference Example 17 | 1/5 | 4 |
| Reference Example 22 | 1/5 | 4 |
| Reference Example 23 | 1/5 | 4 |
| Reference Example 25 | 1/5 | 4 |
| Reference Example 29 | 2/5 | 4 |
| Reference Example 30 | 2/5 | 3 |
| Control* | 0/5 | 4 |

*0.5% methylcellulose

Experimental Example 3
Screening of Urease Inhibitors

One hundred (100) μl of 100 mM Bis-Tris buffer (pH 6.5) and 60 μl of an urease solution prepared from *Helicobacter pylori* were added to 20 μl of a test drug dissolved in 0.1% dimethylformamide solution. The mixture was incubated at room temperature for 30 minutes, and then 20 μl of 100 mM urea was added. The mixture was kept at room temperature for 10 minutes, and then the yielded ammonia in the incubation mixture was measured using a commercial test kit (Ammonia Test Wako®; Wako Pure Chemical). The percent inhibition against the yield of ammonia in the solvent addition group was calculated to obtain the IC$_{50}$ value. The results are shown in Tables 5-1 and 5–2.

TABLE 5-1

| Inhibitory effect against Helicobacter pylori-derived urease (IC$_{50}$: nM) | |
| --- | --- |
| Example No. | IC$_{50}$ |
| 1 | 1.2 |
| 2 | 16 |
| 3 | 5.5 |
| 4 | 6.8 |
| 5 | 3.0 |
| 6 | 3.5 |
| 7 | 4.3 |
| 8 | 4.3 |
| 9 | 13 |
| 10 | 3.6 |
| 11 | 4.2 |
| 12 | 3.6 |
| 13 | 5.2 |
| 14 | 1.1 |
| 15 | 1.7 |
| 16 | 0.8 |
| 17 | 8.2 |
| 18 | 11 |
| 19 | 4.6 |
| 20 | 2.5 |
| 21 | 4.3 |
| 22 | 12 |
| 23 | 2.2 |
| 24 | 9.1 |
| 25 | 1.1 |
| 26 | 1.3 |
| 27 | 4.1 |
| 28 | 1.5 |
| 29 | 8.1 |
| 30 | 4.3 |
| 31 | 7.1 |
| 32 | 8.7 |
| 33 | 1.9 |
| 34 | 12 |
| 35 | 11 |
| 36 | 7.4 |
| 37 | 1.8 |
| 38 | 1.7 |
| 39 | 2.2 |
| 40 | 7.9 |
| 41 | 7.7 |
| 42 | 2.3 |
| 43 | 6.2 |
| 44 | 14 |
| 45 | 1.4 |
| 46 | 5.7 |
| 47 | 1.9 |
| 48 | 8.3 |
| 49 | 27 |
| 50 | 7.5 |
| 51 | 22 |
| 52 | 12 |
| 53 | 7.9 |
| 54 | 3.3 |
| 55 | 3.0 |
| 56 | 41 |
| 57 | 7.5 |
| 58 | 3.0 |
| 59 | 5.4 |
| 60 | 3.6 |
| 61 | 2.8 |
| 62 | 2.8 |
| 63 | 5.6 |
| 64 | 2.9 |
| 65 | 2.3 |

TABLE 5-1-continued

Inhibitory effect against Helicobacter pylori-derived urease ($IC_{50}$: nM)

| Example No. | $IC_{50}$ |
|---|---|
| 66 | 10 |
| 67 | 6.1 |
| 68 | 18 |
| 69 | 9.7 |
| 70 | 13 |
| 71 | 1.9 |
| 72 | 3.6 |
| 73 | 55 |
| 74 | 5.1 |
| 75 | 22 |
| 77 | 8.1 |
| 78 | 4.7 |
| 79 | 6.0 |
| 80 | 4.4 |
| 81 | 7.9 |
| 82 | 27 |
| 83 | 7.0 |
| 84 | 2.5 |
| 85 | 2.2 |
| 86 | 0.9 |
| 87 | 2.5 |
| 88 | 3.3 |
| 89 | 2.6 |
| 90 | 6.3 |
| 91 | 6.3 |
| 92 | 6.0 |

TABLE 5-2

Inhibitory effect against Helicobacter pylori-derived urease ($IC_{50}$: nM)

| Reference Example No. | $IC_{50}$ |
|---|---|
| 1 | 5.0 |
| 2 | 9.6 |
| 3 | 6.6 |
| 4 | 10 |
| 6 | 15 |
| 7 | 6.9 |
| 8 | 4.5 |
| 9 | 9.7 |
| 10 | 7.8 |
| 12 | 44 |
| 15 | 17 |
| 16 | 2.7 |
| 17 | 5.4 |
| 18 | 5.1 |
| 19 | 12 |
| 20 | 6.5 |
| 21 | 7.9 |
| 22 | 9.3 |
| 23 | 5.7 |
| 24 | 8.0 |
| 25 | 1.9 |
| 26 | 13 |
| 27 | 3.9 |
| 28 | 35 |
| 29 | 5.9 |
| 30 | 4.3 |
| 31 | 71 |
| 32 | 14 |
| 33 | 8.3 |
| 34 | 22 |
| 35 | 17 |
| 36 | 8.9 |
| 37 | 17 |
| 38 | 9.7 |
| 39 | 5.9 |
| 40 | 18 |

TABLE 5-2-continued

Inhibitory effect against Helicobacter pylori-derived urease ($IC_{50}$: nM)

| Reference Example No. | $IC_{50}$ |
|---|---|
| 41 | 10 |
| 42 | 22 |
| 43 | 71 |
| 44 | 11 |

Preparation Examples

The anti-Helicobacter agent and pharmaceutical against Helicobacter bacteria of the present invention can, for example, be produced with the following formulations:

1. Capsules

| | |
|---|---|
| (1) Flurofamide | 100 mg |
| (2) Lactose | 90 mg |
| (3) Microcrystalline cellulose | 70 mg |
| (4) Magnesium stearate | 10 mg |
| Total | 270 mg per capsule |

Ingredients (1), (2) and (3) and a half portion of ingredient (4) are mixed and granulated. To these granules, the remaining portion of component (4) is added, and the whole mixture is packed in a gelatin capsule.

2. Tablets

| | |
|---|---|
| (1) Flurofamide | 100 mg |
| (2) Lactose | 35 mg |
| (3) Corn starch | 150 mg |
| (4) Microcrystalline cellulose | 30 mg |
| (5) Magnesium stearate | 5 mg |
| Total | 320 mg per tablet |

Ingredients (1), (2) and (3), a two-third portion of ingredient (4) and a half portion of ingredient (5) are mixed and granulated. To these granules, the remaining portions of ingredients (4) and (5) are added, and the whole mixture is tableted by compressive tableting.

3. Capsules

| | |
|---|---|
| (1) Flurofamide | 100 mg |
| (2) Lansoprazole | 10 mg |
| (3) Lactose | 90 mg |
| (4) Microcrystalline cellulose | 70 mg |
| (5) Magnesium stearate | 10 mg |
| Total | 280 mg per capsule |

Ingredients (1), (2), (3) and (4) and a half portion of ingredient (5) are mixed and granulated. To these granules, the remaining portion of ingredient (5) is added, and the whole mixture is packed in a gelatin capsule.

4. Tablets

| | |
|---|---|
| (1) Flurofamide | 100 mg |
| (2) Lansoprazole | 10 mg |
| (3) Lactose | 35 mg |

4. Tablets

| | |
|---|---|
| (4) Corn starch | 150 mg |
| (5) Microcrystalline cellulose | 30 mg |
| (6) Magnesium stearate | 5 mg |
| Total | 320 mg per tablet |

Ingredients (1), (2), (3) and (4), a two-third portion of ingredient (5) and a half portion of ingredient (6) are mixed and granulated. To these granules, the remaining portions of ingredients (5) and (6) are added, and the whole mixture is tableted by compressive tableting.

5. Combination Preparation (Kit)

Capsules A and B, each of which contains an active ingredient, are prepared separately, and packed into a box.

(a) Capsule A

| | |
|---|---|
| (1) Lansoprazole | 10 mg |
| (2) Lactose | 90 mg |
| (3) Microcrystalline cellulose | 70 mg |
| (4) Magnesium stearate | 10 mg |
| Total | 180 mg per ampule |

Ingredients (1), (2) and (3) and a half portion of ingredient (4) are mixed and granulated. To these granules, the remaining portion of ingredient (4) is added, and the whole mixture is packed in a gelatin capsule.

(b) Capsule B

| | |
|---|---|
| (1) Flurofamide | 100 mg |
| (2) Lactose | 90 mg |
| (3) Microcrystalline cellulose | 70 mg |
| (4) Magnesium stearate | 10 mg |
| Total | 270 mg per ampule |

Ingredients (1), (2) and (3) and a half portion of ingredient (4) are mixed and granulated. To these granules, the remaining portion of ingredient (4) is added, and the whole mixture is packed in a gelatin capsule.

6. Enteric Preparation 1650 g of nonpareil (sugar core prepared by coating 75 parts by weight of sucrose with 25 parts by weight of corn starch by well-known method, 20–28 mesh) is charged in a CF apparatus (CF-360, produced by Freund, Japan) and subjected to sequential spray-coating with dusting powders 1 and 2, having the following compositions and obtained by mixing in advance, in that order, at 60g/min at a rotor rotation rate of 250 rpm, while spraying 1,050 ml of a hydroxypropylcellulose solution (2% w/v) at 30 ml/min at room temperature, followed by vacuum drying at 40° C. for 16 hours and passage through a round sieve, to yield spherical granules with core of 14–32 mesh size.

[Dusting powder 1]

| | |
|---|---|
| Flurofamide | 1,500 g |
| Magnesium carbonate | 336 g |
| Granulated sugar | 297 g |
| Corn starch | 300 g |
| L-HPC | 354 g |

(Substitution degree of hydroxypropoxy group: 10.0–13.0% w/w, mean particle diameter: not more than 30 μm)

[Dusting powder 2]

| | |
|---|---|
| Granulated sugar | 300 g |
| Corn starch | 246 g |
| L-HPC (same as above) | 246 g |

3,800 g of the resulting granules are placed in a fluidized bed coating machine (produced by Ohkawara Company) and subjected to enteric coating at controlled air blow temperature of 65° C. and product temperature of 40° C., while an enteric film solution of the following composition is sprayed at 50 ml/min, to yield enteric granules with core.

These granules are mixed with talc and light silicic anhydride and this mixture is packed in a No. 1 hard capsule using a capsule filling machine (produced by Parke-Davis & Co., USA) to yield a capsule preparation.

[Enteric film solution]

| | |
|---|---|
| Eudragit L30D-55 | 2,018 g |
| (solid content | 650 g) |
| Talc | 182 g |
| Polyethylene glycol 6000 | 60 g |
| Titanium oxide | 60 g |
| Tween 80 | 27 g |
| Water | 4,230 ml |

[Composition per capsule]

| | |
|---|---|
| Enteric granules | 438.8 mg |
| Flurofamide | 100.0 mg |
| Magnesium carbonate | 22.4 mg |
| Nonpareil | 110.0 mg |
| Granulated sugar | 59.8 mg |
| Corn starch | 36.4 mg |
| L-HPC | 40.0 mg |
| Hydroxypropylcellulose | 1.4 mg |
| Eudragit L30D-55 | 44.6 mg |
| Talc | 13.4 mg |
| Polyethylene glycol 6000 | 4.4 mg |
| Titanium oxide | 4.4 mg |
| Tween 80 | 2.0 mg |
| Talc | 0.6 mg |
| Light silicic anhydride | 0.6 mg |
| No. 1 hard capsule | 79.0 mg |
| Total | 519 mg |

INDUSTRIAL APPLICABILITY

The phosphorylamide derivative, the anti-Helicobacter agent and the pharmaceutical against Helicobacter bacteria of the present invention possess antibacterial activity against Helicobacter bacteria, and they exhibit anti- Helicobacter action against Helicobacter bacteria which exhibit toxic action in the digestive tract. The phosphorylamide derivative, the anti-Helicobacter agent and the pharmaceutical against Helicobacter bacteria of the present invention are therefore useful for prevention or treatment of digestive diseases presumably caused by Helicobacter bacteria, such as gastritis, duodenal ulcer, gastric ulcer and chronic gastritis. Since significant correlation between Helicobacter bacteria, especially *Helicobacter pylori*, and gastric cancer has recently been suggested, the phosphorylamide derivative, the anti-Helicobacter agent and pharmaceutical against Helicobacter bacteria of the present invention are also expected to be useful in the prevention of gastric cancer.

We claim:

1. A method for eradicating *Helicobacter pylori* from a mammal, which comprises administering to said mammal a compound represented by the formula:

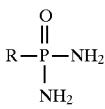

wherein R represents an amino group which may be substituted, or a pharmaceutically acceptable salt thereof, in combination with an antacid or an acid secretion inhibitor.

2. The method according to claim 1, wherein the anti-*Helicobacter pylori* agent is acid-stable.

3. The method according to claim 1, wherein the anti-Helicobacter agent is enteric-coated.

4. The method according to claim 1, wherein R represents an amino group which may be substituted by 1 or 2 substituents selected from the group consisting of (1) an acyl group selected from —$COR^1$, —$CSR^2$, —$SO_2R^3$, —$SOR_4$, —$CONHR^5$ and —$CSNHR^6$ wherein each of $R^1$, $R^2$, $R^3$, $R^4$, $R^5$ and $R^6$ is (1-1) a hydrogen atom;
(1-2) a hydrocarbon group selected from the group consisting of:
  (a) an alkyl group having 1 to 10 carbon atom,
  (b) an alkenyl group having 2 to. 10 carbon atoms,
  (c) an alkynyl group having 2 to 10 carbon atoms,
  (d) a cycloalkyl group having 3 to 12 carbon atoms,
  (e) a cycloalkenyl group having 5 to 12 carbon atoms,
  (f) a cycloalkadienyl group having 5 to 12 carbon atoms,
  (g) a $C_{3-7}$ cycloalkyl-$C_{1-8}$ alkyl group,
  (h) a $C_{5-7}$ cycloalkenyl-$C_{1-8}$ alkyl group, and
  (i) an aryl group having 6 to 10 carbon atoms, each of which may have 1 to 3 substituents selected from the group consisting of:
    (i) a $C_{1-6}$ alkyl group which may be substituted by 1 to 3 substituents selected from the group consisting of halogen and a $C_{1-3}$ alkoxy group,
    (ii) a $C_{1-6}$ alkoxy group which may be substituted by 1 to 3 substituents selected from the group consisting of halogen and a $C_{1-3}$ alkoxy group,
    (iii) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano,
    (iv) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano,
    (v) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro,
    (vi) a carboxyl group, a ($C_{1-6}$ alkoxy)carbonyl group, a ($C_{6-10}$ aryl)oxycarbonyl group or a ($C_{7-10}$ aralkyl)oxycarbonyl group,
    (vii) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro,
    (viii) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group,
    (ix) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 4 substituents selected from the group consisting of
      (ix-1) a $C_{1-6}$ alkyl group which may be substituted by 1 to 3 substituents selected from the group consisting of halogen and a $C_{1-3}$ alkoxy group,
      (ix-2) a $C_{1-6}$ alkoxy group which may be substituted by 1 to 3 substituents selected from the group consisting of halogen and a $C_{1-3}$ alkoxy group,
      (ix-3) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano,
      (ix-4) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano,
      (ix-5) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro,
      (ix-6) a carboxyl group, a ($C_{1-6}$ alkoxy)carbonyl group, a ($C_{6-10}$ aryl)oxycarbonyl group or a ($C_{7-10}$ aralkyl)oxycarbonyl group,
      (ix-7) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro,
      (ix-8) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, nitro, or a cyclic amino group, (ix-9) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (ix-10) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and a $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (ix-11) an acyl group selected from the group consisting formyl, a ($C_{1-6}$ alkyl)carbonyl, a ($C_{3-6}$ cycloalkyl)carbonyl, a ($C_{6-10}$ aryl)carbonyl, a ($C_{7-12}$ aralkyl)carbonyl, a ($C_{1-6}$ alkyl)sulfinyl, a ($C_{3-6}$ cycloalkyl)sulfinyl, a ($C_{6-10}$ aryl)sulfinyl, a ($C_{7-12}$ aralkyl)sulfinyl, a ($C_{1-6}$ alkyl)sulfonyl, a ($C_3$-6 cycloalkyl)sulfonyl, a ($C_{6-10}$ aryl)sulfonyl, a ($C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (ix-12) halogen, (ix-13) nitro, and (ix-14) cyano, (x) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group,each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 4 substituents selected from the group consisting of (x-1) a $C_{1-6}$ alkyl group which may be substituted by 1 to 3 substituents selected from the group consistingof halogen and a $C_{1-3}$ alkoxy group, (x-2) a $C_{1-6}$ alkoxy group which may be substituted by 1 to 3 substituents selected from the group consisting of halogen and a $C_{1-3}$ alkoxy group, (x-3) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano, (x-4) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano, (x-5) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro, (x-6) a carboxyl group, a ($C_{1-6}$ alkoxy)carbonyl group, a ($C_{6-10}$ aryl)oxycarbonyl group or a ($C_{7-10}$ aralkyl)oxycarbonyl group, (x-7) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, (x-8) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group, (x-9) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (x-10) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (x-11) an acyl group selected from the group consisting of formyl, a ($C_{1-6}$ alkyl)carbonyl, a ($C_{3-6}$ cycloalkyl)carbonyl, a ($C_{6-10}$ aryl)carbonyl, a ($C_{7-12}$ aralkyl)carbonyl, a ($C_{1-6}$ alkyl)sulfinyl, a ($C_{3-6}$ cycloalkyl)sulfinyl, a ($C_{6-10}$ aryl)sulfinyl, a ($C_{7-12}$ aralkyl)sulfinyl, a ($C_{1-6}$ alkyl)sulfonyl, a ($C_{3-6}$ cycloalkyl)sulfonyl, a ($C_{6-10}$ aryl)sulfonyl, a ($C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (x-12) halogen,
(x-13) nitro, and
(x-14) cyano, (xi) an acyl group selected from the group consisting of formyl, a ($C_{1-6}$ alkyl)carbonyl, a ($C_{3-6}$ cycloalkyl)carbonyl, a ($C_{6-10}$ aryl)carbonyl, a ($C_{7-12}$ aralkyl)carbonyl, a ($C_{1-6}$ alkyl)sulfinyl, a ($C_{3-6}$ cycloalkyl)sulfinyl, a ($C_{6-10}$ aryl)sulfinyl, a ($C_{7-12}$ aralkyl)sulfinyl, a ($C_{1-6}$ alkyl)sulfonyl, a ($C_{3-6}$ cycloalkyl)sulfonyl, a ($C_{6-10}$ aryl)sulfonyl, a ($C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (xii) halogen,
(xiii) nitro, and
(xiv) cyano, or (1-3) a heterocyclic group which may be substituted by 1 to 4 substituents selected from the group consisting of (i) a $C_{1-6}$ alkyl group which may be substituted by 1 to 3 substituents selected from the group consisting of halogen and a $C_{1-3}$ alkoxy group, (ii) a $C_{1-6}$ alkoxy group which may be substituted by 1 to 3 substituents selected from the group consisting of halogen and a $C_{1-3}$ alkoxy group, (iii) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano, (iv) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano, (v) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen a $C_{6-10}$ aryl group, and nitro, (vi) a carboxyl group, a ($C_{1-6}$ alkoxy)carbonyl group, a ($C_{6-10}$ aryl)oxycarbonyl group or a ($C_{7-10}$ aralkyl)oxycarbonyl group, (vii) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, (viii) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group, (ix) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 4 substituents selected from the group consisting of (ix-1) a $C_{1-6}$ alkyl group which may be substituted by 1 to 3 substituents selected from the group consisting of halogen and a $C_{1-3}$ alkoxy group, (ix-2) a $C_{1-6}$ alkoxy group which may be substituted by 1 to 3 substituents selected from the group consisting of halogen and a $C_{1-3}$ alkoxy group, (ix-3) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano, (ix-4) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano, (ix-5) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro, (ix-6) a carboxyl group, a ($C_{1-6}$ alkoxy)carbonyl group, a ($C_{6-10}$ aryl)oxycarbonyl group or a ($C_{7-10}$ aralkyl)oxycarbonyl group, (ix-7) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group. which may be substituted by halogen, $C_{1-4}$ alkyl group which may be substituted by halogen, and nitro, (ix-8) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group, (ix-9) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (ix-10) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (ix-11) an acyl group selected from the group consisting of formyl, a ($C_{1-6}$ alkyl)carbonyl, a ($C_{3-6}$ cycloalkyl)carbonyl, a ($C_{6-10}$ aryl)carbonyl, a ($C_{7-12}$ aralkyl)carbonyl, a ($C_{1-6}$ alkyl)sulfinyl, a ($C_{3-6}$ cycloalkyl)sulfinyl, a ($C_{6-10}$ aryl)sulfinyl, a ($C_{7-12}$ aralkyl)sulfinyl, a ($C_{1-6}$ alkyl)sulfonyl, a ($C_{3-6}$ cycloalkyl)sulfonyl, a ($C_{6-10}$ aryl)sulfonyl, a ($C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (ix-11) halogen, (ix-12) nitro, and (ix-13) cyano, (x) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 4 substituents selected from the group consisting of (x-1) a $C_{1-6}$ alkyl group which may be substituted by 1 to 3 substituents selected from the group consisting of halogen and a $C_{1-3}$ alkoxy group, (x-2) a $C_{1-6}$ alkoxy group which may be substituted by 1 to 3 substituents selected from the group consisting of halogen and $C_{1-3}$ alkoxy group, (x-3) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano, (x-4) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano, (x-5) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro, (x-6) a carboxyl group, a ($C_{1-6}$ alkoxy)carbonyl group, a ($C_{6-10}$ aryl)oxycarbonyl group or a ($C_{7-10}$ aralkyl)oxycarbonyl group, (x-7) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, (x-8) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group, (x-9) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalky, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstitruted or substituted by 1 to 3 substituents selected from the group consisting of a $C_{1-4}$ alkoxy group, halogen, $C_{1-4}$ alkyl group and $C_{6-10}$ aryl group, (x-10) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (x-11) an acyl group selected from the group consisting of formyl, a ($C_{1-6}$ alkyl)carbonyl, a ($C_{3-6}$ cycloalkyl)carbonyl, a ($C_{6-10}$ aryl)carbonyl, a ($C_{7-12}$ aralkyl)carbonyl, a ($C_{1-6}$ alkyl)sulfinyl, a ($C_{3-6}$ cycloalkyl)sulfinyl, a ($C_{6-10}$ aryl)sulfinyl, a ($C_{7-12}$ aralkyl)sulfinyl, a ($C_{1-6}$ alkyl)sulfonyl, a ($C_{3-6}$ cycloalkyl)sulfonyl, a ($C_{6-10}$ aryl)sulfonyl, a ($C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (x-12) halogen,
(x-13) nitro, and
(x-14) cyano, (xi) an acyl group selected from the group consisting of formyl, a ($C_{1-6}$ alkyl)carbonyl, a ($C_{3-6}$ cycloalkyl)carbonyl, a ($C_{6-10}$ aryl)carbonyl, a ($C_{7-12}$ aralkyl)carbonyl, a ($C_{1-6}$ alkyl)sulfinyl, a ($C_{3-6}$ cycloalkyl)sulfinyl, a ($C_{6-10}$ aryl)sulfinyl, a ($C_{7-12}$ aralkyl)sulfinyl, a ($C_{1-6}$ alkyl)sulfonyl, a ($C_{3-6}$ cycloalkyl)sulfonyl, a ($C_{6-10}$ aryl)sulfonyl, a ($C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (xii) halogen,
(xiii) nitro, and
(xiv) cyano, (2) an optionally esterified carboxyl group represented by the formula: —COOR$^7$ wherein R$^7$ is (2-1) a hydrogen atom;
(2-2) a hydrocarbon group selected from the group consisting of:
  (a) an alkyl group having 1 to 10 carbon atoms,
  (b) an alkenyl group having 2 to 10 carbon atoms,
  (c) an alkynyl group having 2 to 10 carbon atoms,
  (d) a cycloalkyl group having 3 to 12 carbon atoms,
  (e) a cycloalkenyl group having 5 to 12 carbon atoms,
  (f) a cycloalkadienyl group having 5 to 12 carbon atoms,
  (g) a $C_{3-7}$ cycloalkyl-$C_{1-8}$ alkyl group,
  (h) a $C_{5-7}$ cycloalkenyl-$C_{1-8}$ alkyl group, and
  (i) an aryl group having 6 to 10 carbon atoms, each of which may have 1 to 3 substituents selected from the group consisting of:
    (i) a $C_{1-6}$ alkyl group which may be substituted by 1 to 3 substituents selected from the group consisting of halogen and a $C_{1-3}$ alkoxy group,
    (ii) a $C_{1-6}$ alkoxy group which may be substituted by 1 to 3 substituents selected from the group consisting of halogen and a $C_{1-3}$ alkoxy group,
    (iii) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano,
    (iv) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano,
    (v) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro,
    (vi) a carboxyl group, a ($C_{1-6}$ alkoxy)carbonyl group, a ($C_{6-10}$ aryl)oxycarbonyl group or a ($C_{7-10}$ aralkyl)oxycarbonyl group,
    (vii) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro,
    (viii) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group,
    (ix) a hydroxyl group. which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 4 substituents selected from the group consisting of
      (ix-1) a $C_{1-6}$ alkyl group which may be substituted by 1 to 3 substituents selected from the group consisting of halogen and a $C_{1-3}$ alkoxy group,
      (ix-2) a $C_{1-6}$ alkoxy group which may be substituted by 1 to 3 substituents selected from the group consisting of halogen and a $C_{1-3}$ alkoxy group,
      (ix-3) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano,
      (ix-4) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano,
      (ix-5) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro,
      (ix-6) a carboxyl group, a ($C_{1-6}$ alkoxy)carbonyl group, a ($C_{6-10}$ aryl)oxycarbonyl group or a ($C_{7-10}$ aralkyl)oxycarbonyl group,
      (ix-7) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, (ix-8) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group, (ix-9) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-2}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (ix-10) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{1-2}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (ix-11) an acyl group selected from the group consisting formyl, a $(C_{1-6}$ alkyl)carbonyl, a $(C_{3-6}$ cycloalkyl)carbonyl, a $(C_{6-10}$ aryl)carbonyl, a $(C_{7-12}$ aralkyl)carbonyl, a $(C_{1-6}$ alkyl)sulfinyl, a $(C_{3-6}$ cycloalkyl)sulfinyl, a $(C_{6-10}$ aryl)sulfinyl, a $(C_{7-12}$ aralkyl)sulfinyl, a $(C_{1-6}$ alkyl)sulfonyl, a $(C_{3-6}$ cycloalkyl)sulfonyl, a $(C_{6-10}$ aryl)sulfonyl, a $(C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (ix-12) halogen,
(ix-13) nitro, and
(ix-14) cyano, (x) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 4 substituents selected from the group consisting of (x-1) a $C_{1-6}$ alkyl group which may be substituted by 1 to 3 substituents selected from the group consisting of halogen and a $C_{1-3}$ alkoxy group, (x-2) a $C_{1-6}$ alkoxy group which may be substituted by 1 to 3 substituents selected from the group consisting of halogen and a $C_{1-3}$ alkoxy group, (x-3) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano, (x-4) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano, (x-5) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro, (x-6) a carboxyl group, a $(C_{1-6}$ alkoxy)carbonyl group, a $(C_{6-10}$ aryl)oxycarbonyl group or a $(C_{7-10}$ aralkyl)oxycarbonyl group, (x-7) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, (x-8) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group, (x-9) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (x-10) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (x-11) an acyl group selected from the group consisting of formyl, a ($C_{1-6}$ alkyl)carbonyl, a ($C_{3-6}$ cycloalkyl)carbonyl, a ($C_{6-10}$ aryl) carbonyl, a ($C_{7-12}$ aralkyl)carbonyl, a ($C_{1-6}$ alkyl)sulfinyl, a ($C_{3-6}$ cycloalkyl)sulfinyl, a ($C_{6-10}$ aryl)sulfinyl, a ($C_{7-12}$ aralkyl)sulfinyl, a ($C_{1-6}$ alkyl)sulfonyl, a ($C_{3-6}$ cycloalkyl) sulfonyl, a ($C_{6-10}$ aryl)sulfonyl, a ($C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (x-12) halogen, (x-13) nitro, and (x-14) cyano, (xi) an acyl group selected from the consisting of formyl, a ($C_{1-6}$ alkyl)carbonyl, a ($C_{3-6}$ cycloalkyl) carbonyl, a ($C_{6-10}$ aryl)carbonyl, a ($C_{7-12}$ aralkyl) carbonyl, a ($C_{1-6}$ alkyl)sulfinyl, a ($C_{3-6}$ cycloalkyl.)sulfinyl, a ($C_{6-10}$ aryl)sulfinyl, a ($C_{7-12}$ aralkyl)sulfinyl, a ($C_{1-6}$ alkyl)sulfonyl, a ($C_{3-6}$ cycloalkyl)sulfonyl, a ($C_{6-10}$ aryl)sulfonyl, a ($C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (xii) halogen, (xiii) nitro, and (xiv) cyano, or (2-3) a heterocyclic group which may be substituted by 1 to 4 substituents selected from the consisting of (i) a $C_{1-6}$ alkyl group which may be substituted by 1 to 3 substituents selected from the group consisting of halogen and a $C_{1-3}$ alkoxy group, (ii) a $C_{1-6}$ alkoxy group which may be substituted by 1 to 3 substituents selected from the group consisting of halogen and a $C_{1-3}$ alkoxy group, (iii) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano, (iv) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano, (v) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro, (vi) a carboxyl group, a $C_{1-6}$ alkoxy)carbonyl group, a ($C_{6-10}$ aryl)oxycarbonyl group or a ($C_{7-10}$ aralkyl) oxycarbonyl group, (vii) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, (viii) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group, (ix) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstitued or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 4 substituents selected from the group consisting of (ix-1) a $C_{1-6}$ alkyl group which may be substituted by 1 to 3 substituents selected from the group consisting of halogen and a $C_{1-3}$ alkoxy group, (ix-2) a $C_{1-6}$ alkoxy group which may be substituted by 1 to 3 substituents selected from the group consisting of halogen and a $C_{1-3}$ alkoxy group, (ix-3) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano, (ix-4) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano, (ix-5) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro, (ix-6) a carboxyl group, a ($C_{1-6}$ alkoxy)carbonyl group, a ($C_{6-10}$ aryl)oxycarbonyl group or a ($C_{7-10}$ aralkyl)oxycarbonyl group, (ix-7) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, (ix-8) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group, (ix-9) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (ix-10) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (ix-11) an acyl group selected from the group consisting of formyl, a $(C_{1-6}$ alkyl)carbonyl, a $(C_{3-6}$ cycloalkyl)carbonyl, a $(C_{6-10}$ aryl)carbonyl, a $(C_{7-12}$ aralkyl)carbonyl, a $(C_{1-6}$ alkyl)sulfinyl, a $(C_{3-6}$ cycloalkyl)sulfinyl, a $(C_{6-10}$ aryl)sulfinyl, a $(C_{7-12}$ aralkyl)sulfinyl, a $(C_{16}$ alkyl)sulfonyl, a $(C_{3-6}$ cycloalkyl)sulfonyl, a $(C_{6-10}$ aryl)sulfonyl, a $(C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (ix-12) halogen,
(ix-13) nitro, and
(ix-14) cyano, (x) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 4 substituents selected from the group consisting of (x-1) a $C_{1-6}$ alkyl group which may be substituted by 1 to 3 substituents selected from the group consisting of halogen and a $C_{1-3}$ alkoxy group, (x-2) a $C_{1-6}$ alkoxy group which may be substituted by 1 to 3 substituents selected from the group consisting of halogen and a $C_{1-3}$ alkoxy group, (x-3) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano, (x-4) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano, (x-5) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro, (x-6) a carboxyl group, a $(C_{1-6}$ alkoxy)carbonyl group, a $(C_{6-10}$ aryl)oxycarbonyl group or a $(C_{7-10}$ aralkyl)oxycarbonyl group, (x-7) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, (x-8) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group, (x-9) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (x-10) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, alhogen, $C_{1-4}$ alkyl group and $C_{6-10}$ aryl group, (x-11) an acyl group selected from the group consisting of formyl, a ($C_{1-6}$ alkyl)carbonyl, a ($C_{3-6}$ cycloalkyl)carbonyl, a ($C_{6-10}$ aryl)carbonyl, a ($C_{7-12}$ aralkyl)carbonyl, a ($C_{1-6}$ alkyl)sulfinyl, a ($C_{3-6}$ cycloalkyl)sulfinyl, a ($C_{6-10}$ aryl)sulfinyl, a ($C_{7-12}$ aralkyl)sulfinyl, a ($C_{1-6}$ alkyl)sulfonyl, a ($C_{3-6}$ cycloalkyl)sulfonyl, a ($C_{6-10}$ aryl)sulfonyl, a ($C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (x-12) halogen,
(x-13) nitro, and
(x-14) cyano, (xi) an acyl group selected from the group consisting of formyl, a ($C_{1-6}$ alkyl)carbonyl, a ($C_{3-6}$ cycloalkyl) carbonyl, a ($C_{6-10}$ aryl)carbonyl, a ($C_{7-12}$ aralkyl) carbonyl, a ($C_{1-6}$ alkyl)sulfinyl, a ($C_{3-6}$ cycloalkyl) sulfinyl, a ($C_{6-10}$ aryl)sulfinyl, a ($C_{7-12}$ aralkyl) sulfinyl, a ($C_{1-6}$ alkyl)sulfonyl, a ($C_{3-6}$ cycloalkyl) sulfonyl, a ($C_{6-10}$ aryl)sulfonyl, a ($C_{7-12}$ aralkyl) sulfonyl, each of said groups being unsubstituted or substituted by 1 to 5 substituents selected from the group consisting of halogen, a $C_{1-4}$ alkoxy group and a $C_{1-4}$ alkyl group, (xii) halogen,
(xiii) nitro, and
(xiv) cyano, and, (3) a hydrocarbon group selected from the group consisting of
(a) an alkyl group having 1 to 10 carbon atoms,
(b) an alkenyl group having 2 to 10 carbon atoms,
(c) an alkynyl group having 2 to 10 carbon atoms,
(d) a cycloalkyl group having 3 to 12 carbon atoms,
(e) a cycloalkenyl group having 5 to 12 carbon atoms,
(f) a cycloalkadienyl group having 5 to 12 carbon atoms,
(g) a $C_{3-7}$ cycloalkyl-$C_{1-8}$ alkyl group,
(h) a $C_{5-7}$ cycloalkenyl-$C_{1-8}$ alkyl group, and
(i) an aryl group having 6 to 10 carbon atoms, each of which may have 1 to 3 substituents selected from the group consisting of:
(i) a $C_{1-6}$ alkyl group which may be substituted by 1 to 3 substituents selected from the group consisting of halogen and a $C_{1-3}$ alkoxy group,
(ii) a $C_{1-6}$ alkoxy group which may be substituted by 1 to 3 substituents selected from the group consisting of halogen and a $C_{1-3}$ alkoxy group,
(iii) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano,
(iv) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano,
(v) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro,
(vi) a carboxyl group, a ($C_{1-6}$ alkoxy)carbonyl group, a ($C_{6-10}$ aryl)oxycarbonyl group or a ($C_{7-10}$ aralkyl) oxycarbonyl group,
(vii) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro,
(viii) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group,
(ix) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 4 substituents selected from the group consisting of
(ix-1) a $C_{1-6}$ alkyl group which may be substituted by 1 to 3 substituents selected from the group consisting of halogen and a $C_{1-3}$ alkoxy group,
(ix-2) a $C_{1-6}$ alkoxy group which may be substituted by 1 to 3 substituents selected from the group consisting of halogen and a $C_{1-3}$ alkoxy group,
(ix-3) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano,
(ix-4) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano,
(ix-5) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro,
(ix-6) a carboxyl group, a ($C_{1-6}$ alkoxy)carbonyl group, a ($C_{6-10}$ aryl)oxycarbonyl group or a ($C_{7-10}$ aralkyl)oxycarbonyl group,
(ix-7) a carbaomoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro,
(ix-8) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group,
(ix-9) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, a $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group,
(ix-10) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group,
(ix-11) an acyl group selected from the group consisting of formyl, a $(C_{1-6}$ alkyl)carbonyl, a $(C_{3-6}$ cycloalkyl)carbonyl, a $(C_{6-10}$ aryl)carbonyl, a $(C_{7-12}$ aralkyl)carbonyl, a $(C_{1-6}$ alkyl)sulfinyl, a $(C_{3-6}$ cycloalkyl)sulfinyl, a $(C_{6-10}$ alkyl)sulfinyl, a $(C_{7-12}$ aralkyl)sulfinyl, a $(C_{1-6}$ alkyl)sulfonyl, a $(C_{3-6}$ cycloalkyl)sulfonyl, a $(C_{6-10}$ aryl)sulfonyl, a $(C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group,
(ix-12) halogen,
(ix-13) nitro, and
(ix-14) cyano,
(x) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 4 substituents selected from the group consisting of
(x-1) a $C_{1-6}$ alkyl group which may be substituted by 1 to 3 substituents selected from the group consisting of halogen and a $C_{1-3}$ alkoxy group,
(x-2) a $C_{1-6}$ alkoxy group which may be substituted by 1 to 3 substituents selected from the group consisting of halogen and a $C_{1-3}$ alkoxy group,
(x-3) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano,
(x-4) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano,
(x-5) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro,
(x-6) a carboxyl group, a $(C_{1-6}$ alkoxy)carbonyl group, a $(C_{6-10}$ aryl)oxycarbonyl group or a $(C_{7-10}$ aralkyl)oxycarbonyl group,
(x-7) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro,
(x-8) an amino group which may be substituted by 1 or 2 substituents selected from the group consisting of a $C_6$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group,
(x-9) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group,
(x-10) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (x-11) an acyl group selected from the group consisting of formyl, a ($C_{1-6}$ alkyl)carbonyl, a ($C_{3-6}$ cycloalkyl)carbonyl, a ($C_{6-10}$ aryl)carbonyl, a ($C_{7-12}$ aralkyl)carbonyl, a ($C_{1-6}$ alkyl)sulfinyl, a ($C_{3-6}$ cycloalkyl)sulfinyl, a ($C_{6-10}$ aryl)sulfinyl, a ($C_{7-12}$ aralkyl)sulfinyl, a ($C_{1-6}$ alkyl)sulfonyl, a ($C_{3-6}$ cycloalkyl)sulfonyl, a ($C_{6-10}$ aryl)sulfonyl, a ($C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (x-12) halogen,
(x-13) nitro, and
(x-14) cyano, (xi) an acyl group selected from the group consisting of formyl, a ($C_{1-6}$ alkyl)carbonyl, a ($C_{3-6}$ cycloalkyl)carbonyl, a ($C_{6-10}$ aryl)carbonyl, a ($C_{7-12}$ aralkyl)carbonyl, a ($C_{1-6}$ alkyl)sulfinyl, a ($C_{3-6}$ cycloalkyl)sulfinyl, a ($C_{6-10}$ aryl)sulfinyl, a ($C_{7-12}$ aralkyl)sulfinyl, a ($C_{1-6}$ alkyl)sulfonyl, a ($C_{3-6}$ cycloalkyl)sulfonyl, a ($C_{6-10}$ aryl)sulfonyl, a ($C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (xii) halogen,
(xiii) nitro, and
(xiv) cyano.

5. The method according to claim 1, wherein R is an amino group which may be substituted by an acyl group.

6. The method according to claim 5, wherein the acyl group is a group represented by the formula:

—COR$^1$ wherein R$^1$ represents hydrogen, a hydrocarbon group which may be substituted or a heterocyclic group which may substituted.

7. The method according to claim 6, wherein R$^1$ is a furyl group or a thienyl group, each of which may be substituted.

8. The method according to claim 6, wherein R$^1$ is (a) a heterocyclic group which may be substituted (except excluding a furyl group which may be substituted and a pyridyl group which may be substituted and a 3-amino-2-oxo-1-azetidinyl group which may be substituted), (b) a hydrocarbon group substituted by a heterocyclic group which may be substituted (except excluding a hydrocarbon group substituted by a maleimido group which may be substituted), (c) a hydrocarbon group substituted by a substituted phenoxy group, (d) a hydrocarbon group substituted by a heterocyclic-thio group which may be substituted, or (e) an alkyl group substituted by an arylsulfonylamino group which may be substituted.

9. The method according to claim 6, wherein R$^1$ is a furyl group or a pyridyl group, each of which has 1 to 3 substituents selected from the group consisting of halogen, cyano, formyl, $C_{1-3}$ alkyl which may be substituted by halogen, $C_{1-3}$ alkoxy which may be substituted by halogen, ($C_{1-3}$ alkoxy)carbonyl which may be substituted by halogen and $C_{1-3}$ alkylsulfonyl which may be substituted by halogen.

10. The method according to claim 1, wherein R is —NHCOR$^1$ or —NHSO$_2$R$^3$ wherein each of R$^1$ and R$^3$ is
(1) a $C_{1-4}$ alkyl group,
(2) a $C_{2-4}$ alkenyl group,
(3) a $C_{6-10}$ aryl group or
(4) a aromatic heterocyclic group selected from the group consisting of furyl, benzofuranyl, thienyl, benzothienyl, indolyl, isoindolyl, pyrazinyl, pyridyl, pyrimidinyl, azolyl and fused azolyl, wherein each of said $C_{1-4}$ alkyl, $C_{2-4}$ alkenyl and $C_{6-10}$ aryl groups may be substituted by 1 to 3 substituents selected from the group consisting of
(a) a $C_{1-3}$ alkyl group which may be substituted by halogen,
(b) a $C_{1-3}$ alkoxy group,
(c) a $C_{6-10}$ aryl group which may be substituted by halogen, amino, nitro or cyano,
(d) a $C_{6-10}$ aryloxy group which may be substituted by $C_{1-3}$ alkoxy, halogen, nitro, cyano or amino,
(e) a heterocyclic group selected from thienyl, benzimidazolyl, benzoxazolyl and benzisoxazolyl, each of which may be substituted by halogen,
(f) an amino group which may be substituted by p-toluenesulfonyl,
(g) a hydroxyl group,
(h) a thiol group which may be substituted by a $C_{6-10}$ aryl group or a heterocyclic group selected from benzoxazolyl and benzothiazolyl, each of said aryl group and heterocyclic groups being unsubstituted or substituted by halogen or a $C_{1-3}$ alkoxy group,
(i) halogen,
(j) nitro, and
(k) cyano, and wherein said aromatic heterocyclic group may be substituted by 1 to 3 substituents selected from the group consisting of
(a) a $C_{1-3}$ alkyl group which may be substituted by halogen,
(b) a $C_{6-10}$ aryl group,
(c) a $C_{1-3}$ alkoxy group which may be substituted by halogen,
(d) halogen,
(e) nitro,
(f) cyano,
(g) a ($C_{1-6}$ alkyl)carbonyl group, and
(h) a ($C_{1-6}$ alkyl)sulfonyl group.

11. The use according to claim 1, wherein R is —NHCOR$^1$ or —NHSO$_2$R$^3$ wherein each of R$^1$ and R$^3$ is
(1) a $C_{1-4}$ alkyl group,
(2) a $C_{2-4}$ alkenyl group,
(3) a $C_{6-10}$ aryl group or
(4) a aromatic heterocyclic group selected from the group consisting of furyl, thienyl, indolyl, isoindolyl, pyrazinyl, pyridyl, pyrimidinyl, azolyl and fused azolyl, wherein each of said $C_{1-4}$ alkyl, $C_{2-4}$ alkenyl and $C_{6-10}$ aryl groups may be substituted by 1 to 3 substituents selected from the group consisting of
(a) a $C_{1-3}$ alkyl group which may be substituted by halogen,
(b) a $C_{1-3}$ alkoxy group,
(c) a $C_{6-10}$ aryl group which may be substituted by halogen,
(d) a $C_{6-10}$ aryloxy group which may be substituted by $C_{1-3}$ alkoxy, halogen or nitro,
(e) a heterocyclic group selected from thienyl, benzimidazolyl and benzoxazolyl, each of which may be substituted by halogen, (f) an amino group which may be substituted by p-toluenesulfonyl,
(g) a hydroxyl group,
(h) a thiol group which may be substituted by a heterocyclic group selected from benzoxazolyl and benzothiazolyl,
(i) halogen,
(j) nitro, and
(k) cyano, and
wherein said aromatic heterocyclic group may be substituted by 1 to 3 substituents selected from the group consisting of
(a) a $C_{1-3}$ alkyl group which may be substituted by halogen,
(b) a $C_{6-10}$ aryl group,
(c) a $C_{1-3}$ alkoxy group which may be substituted by halogen,
(d) halogen, and
(e) nitro.

12. A method of preventing recurrence of an ulcer in a mammal, which comprises administering to said mammal a compound represented by the formula:

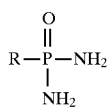

wherein R represents an amino group which may be substituted, or a pharmaceutically acceptable salt thereof, in combination with an antacid or an acid secretion inhibitor.

13. A combination preparation which contains a compound represented by the formula:

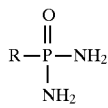

wherein R represents an amino group which may be substituted, or a pharmaceutically acceptable salt thereof, and an antacid or an acid secretion inhibitor.

14. A compound represented by the formula (IA):

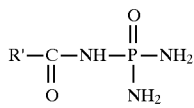

wherein R' represents (a) a heterocyclic group which may be substituted (except excluding a furyl group which may be substituted, a pyridyl group which may be substituted and a 3-amino-2-oxo-1-azetidinyl group which may be substituted), (b, a hydrocarbon group substituted by a heterocyclic group which may be substituted (except a excluding a hydrocarbon group substituted by a maleimido group which may be substituted), (c) a hydrocarbon group substituted by a substituted phenoxy group, (d) a hydrocarbon group substituted by a heterocyclic-thio group which may be substituted, or (e) an alkyl group substituted by an arylsulfonylamino group which may be substituted, or a salt thereof.

15. The compound according to claim 14, wherein R' is
(1) a heterocyclic group which may be substituted by 1 to 4 substituents selected from the group consisting of
(i) a $C_{1-6}$ alkyl group which may be substituted by 1 to 3 substituents selected from the group consisting of halogen and a $C_{1-3}$ alkoxy group, (ii) a $C_{1-6}$ alkoxy group which may be substituted by 1 to 3 substituents selected from the group consisting of halogen and a $C_{1-3}$ alkoxy group,
(iii) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano,
(iv) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano,
(v) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro,
(vi) a carboxyl group, a ($C_{1-6}$ alkoxy)carbonyl group, a ($C_{6-10}$ aryl)oxycarbonyl group or a ($C_{7-10}$ aralkyl) oxycarbonyl group,
(vii) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting oa halogen, a $C_{1-4}$ alkoxy group which may be substituted by halogen, $C_{1-4}$ alkyl group which may be substituted by halogen, and nitro,
(viii) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group,
(ix) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 4 substituents selected from the group consisting of
(ix-1) a $C_{1-6}$ alkyl group which may be substituted by 1 to 3 substituents selected from the group consisting of halogen and a $C_{1-3}$ alkoxy group,
(ix-2) a $C_{1-6}$ alkoxy group which may be substituted by 1 to 3 substituents selected from the group consisting of halogen and a $C_{1-3}$ alkoxy group,
(ix-3) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano,
(ix-4) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano,
(ix-5) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro,
(ix-6) a carboxyl group, a ($C_{1-6}$ alkoxy)carbonyl group, a ($C_{6-10}$ aryl)oxycarbonyl group or a ($C_{7-10}$ aralkyl)oxycarbonyl group,
(ix-7) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro,
(ix-8) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group,
(ix-9) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group,
(ix-10) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group,
(ix-11) an acyl group selected from the group consisting of formyl, a ($C_{1-6}$ alkyl)carbonyl, a ($C_{3-6}$ cycloalkyl)carbonyl, a ($C_{6-10}$ aryl)carbonyl, a ($C_{7-12}$ aralkyl)carbonyl, a ($C_{1-6}$ alkyl)sulfinyl, a ($C_{3-6}$ cycloalkyl)sulfinyl, a ($C_{6-10}$ aryl)sulfinyl, a ($C_{7-12}$ aralkyl)sulfinyl, a ($C_{1-6}$ alkyl)sulfonyl, a ($C_{3-6}$ cycloalkyl)sulfonyl, a ($C_{6-10}$ aryl)sulfonyl, a ($C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group,
(ix-12) halogen,
(ix-13) nitro, and
(ix-14) cyano,
(x) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 4 substituents selected from the group consisting of
(x-1) a $C_{1-6}$ alkyl group which may be substituted by 1 to 3 substituents selected from the group consisting of halogen and a $C_{1-3}$ alkoxy group,
(x-2) a $C_{1-6}$ alkoxy group which may be substituted by 1 to 3 substituents selected from the group consisting of halogen and a $C_{1-3}$ alkoxy group,
(x-3) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano,
(x-4) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano,
(x-5) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro,
(x-6) a carboxyl group, a ($C_{1-6}$ alkoxy)carbonyl group, a ($C_{6-10}$ aryl)oxycarbonyl group or a ($C_{7-10}$ aralkyl)oxycarbonyl group,
(x-7) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro,
(x-8) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group,
(x-9) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (x-10) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (x-11) an acyl group selected from the group consisting of formyl, a ($C_{1-6}$ alkyl)carbonyl, a ($C_{3-6}$ cycloalkyl)carbonyl, a ($C_{6-10}$ aryl)carbonyl, a ($C_{7-12}$ aralkyl)carbonyl, a ($C_{1-6}$ alkyl)sulfinyl, a ($C_{3-6}$ cycloalkyl)sulfinyl, a ($C_{6-10}$ aryl)sulfinyl, a ($C_{7-12}$ aralkyl)sulfinyl, a ($C_{1-6}$ alkyl)sulfonyl, a ($C_{3-6}$ cycloalkyl)sulfonyl, a ($C_{6-10}$ aryl)sulfonyl, a ($C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (x-12) halogen,
(x-13) nitro, and
(x-14) cyano, (xi) an acyl group selected from the group consisting of formyl, a ($C_{1-6}$ alkyl)carbonyl, a ($C_{3-6}$ cycloalkyl)carbonyl, a ($C_{6-10}$ aryl)carbonyl, a ($C_{7-12}$ aralkyl)carbonyl, a ($C_{1-6}$ alkyl)sulfinyl, a ($C_{3-6}$ cycloalkyl)sulfinyl, a ($C_{6-10}$ aryl)sulfinyl, a ($C_{7-12}$ aralkyl)sulfinyl, a ($C_{1-6}$ alkyl)sulfonyl, a ($C_{3-6}$ cycloalkyl)sulfonyl, a ($C_{6-10}$ aryl)sulfonyl, a ($C_{7-12}$ aralkyl)sulfonyl, each of said groups being unsubstituted or substituted by 1 to 5 substituents selected from the group consisting of halogen, a $C_{1-4}$ alkoxy group and a $C_{1-4}$ alkyl group, (xii) halogen,
(xiii) nitro, and
(xiv) cyano, (2) a hydrocarbon group selected from the group consisting of
(a) an alkyl group having 1 to 10 carbon atoms,
(b) an alkenyl group having 2 to 10 carbon atoms,
(c) an alkynyl group having 2 to 10 carbon atoms,
(d) a cycloalkyl group having 3 to 12 carbon atoms,
(e) a cycloalkenyl group having 5 to 12 carbon atoms,
(f) a cycloalkadienyl group having 5 to 12 carbon atoms,
(g) a $C_{3-7}$ cycloalkyl-$C_{1-8}$ alkyl group,
(h) a $C_{5-7}$ cycloalkenyl-$C_{1-8}$ alkyl group, and
(i) an aryl group having 6 to 10 carbon atoms, each of which is substituted by a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro, (3) a hydrocarbon group selected from the group consisting of
(a) an alkyl group having 1 to 10 carbon atoms,
(b) an alkenyl group having 2 to 10 carbon atoms,
(c) an alkynyl group having 2 to 10 carbon atoms,
(d) a cycloalkyl group having 3 to 12 carbon atoms,
(e) a cycloalkenyl group having 5 to 12 carbon atoms,
(f) a cycloalkadienyl group having 5 to 12 carbon atoms,
(g) a $C_{3-7}$ cycloalkyl-$C_{1-8}$ alkyl group,
(h) a $C_{5-7}$ cycloalkenyl-$C_{1-8}$ alkyl group, and
(i) an aryl group having 6 to 10 carbon atoms, each of which is substituted by a phenoxy group which is substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, (4) a hydrocarbon group selected from the group consisting of
(a) an alkyl group having 1 to 10 carbon atoms,
(b) an alkenyl group having 2 to 10 carbon atoms,
(c) an alkynyl group having 2 to 10 carbon atoms,
(d) a cycloalkyl group having 3 to 12 carbon atoms,
(e) a cycloalkenyl group having 5 to 12 carbon atoms,
(f) a cycloalkadienyl group having 5 to 12 carbon atoms,
(g) a $C_{3-7}$ cycloalkyl-$C_{1-8}$ alkyl group,
(h) a $C_{5-7}$ cycloalkenyl-$C_{1-8}$ alkyl group, and
(i) an aryl group having 6 to 10 carbon atoms, each of which is substituted by a thiol group which is substituted by a heterocyclic group which may be substituted by 1 to 4 substituents selected from the group consisting of
(i) a $C_{16}$ alkyl group which may be substituted by 1 to 3 substituents selected from the group consisting of halogen and a $C_{1-3}$ alkoxy group,
(ii) a $C_{1-6}$ alkoxy group which may be substituted by 1 to 3 substituents selected from the group consisting of halogen and a $C_{1-3}$ alkoxy group,
(iii) a $C_{6-14}$ aryl group which may be substituted by 1 to 5 substituents selected from the group consisting of a $C_{1-3}$ alkoxy group, halogen, a $C_{1-3}$ alkyl group, amino, nitro and cyano,
(iv) a $C_{3-7}$ cycloalkyl group or a $C_{3-6}$ cycloalkenyl group, each of which may be substituted by 1 to 5 substituents selected from the group consisting of a $C_{1-3}$ alkoxy group, halogen, a $C_{1-3}$ alkyl group, amino, nitro and cyano,
(v) a heterocyclic group which may be substituted by 1 to 3 substituents selected from the group consisting of a $C_{1-4}$ alkoxy group which may be substituted by halogen, halogen, a $C_{1-4}$ alkyl group which may be substituted by halogen, a $C_{6-10}$ aryl group, and nitro
(vi) a carboxyl group, a ($C_{1-6}$ alkoxy)carbonyl group, a ($C_{6-10}$ aryl)oxycarbonyl group or a ($C_{7-10}$ aralkyl) oxycarbonyl group,
(vii) a carbamoyl group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, (viii) an amino group which may be substituted by 1 or 2 substituents selected from the group consisting of a $C_{1-6}$ alkyl group, a $C_{3-6}$ cycloalkyl group, a $C_{6-10}$ aryl group, a $C_{7-12}$ aralkyl group and a $C_{6-10}$ arylsulfonyl group, each of said groups being unsubstituted or substituted by 1 to 5 substituents selected from the group consisting of halogen, a $C_{1-4}$ alkoxy group which may be substituted by halogen, $C_{1-4}$ alkyl group which may be substituted by halogen, and nitro, or a cyclic amino group, (ix) a hydroxyl group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (x) a thiol group which may be substituted by a $C_{1-6}$ alkyl group, a $C_{3-6}$ cycloalkyl group, a $C_{6-10}$ aryl group, a $C_{7-12}$ aralkyl group or a heterocyclic group, each of said $C_{1-6}$ alkyl, $C_{3-6}$ cycloalkyl, $C_{6-10}$ aryl and $C_{7-12}$ aralkyl groups being unsubstituted or substituted by 1 to 5 substituents selected from the group consisting of halogen, a $C_{1-4}$ alkoxy group which may be substituted by halogen, a $C_{1-4}$ alkyl group which may be substituted by halogen, nitro, amino and cyano, and said heterocyclic group being unsubstituted or substituted by 1 to 3 substituents selected from the group consisting of a $C_{1-4}$ alkoxy group, halogen, $C_{1-4}$ alkyl group and $C_{6-10}$ aryl group, (xi) an acyl group selected from the group consisting of formyl, a ($C_{1-6}$ alkyl)carbonyl, a ($C_{3-6}$ cycloalkyl) carbonyl, a ($C_{6-10}$ aryl)carbonyl, a ($C_{7-12}$ aralkyl) carbonyl, a ($C_{1-6}$ alkyl)sulfinyl, a ($C_{3-6}$ cycloalkyl) sulfinyl, a ($C_{6-10}$ aryl)sulfinyl, a ($C_{7-12}$ aralkyl) sulfinyl, a ($C_{1-6}$ alkyl)sulfonyl, a ($C_{3-6}$ cycloalkyl) sulfonyl, a ($C_{6-10}$ aryl)sulfonyl, a ($C_{7-12}$ aralkyl) sulfonyl, each of said groups being unsubstituted or substituted by 1 to 5 substituents selected from the group consisting of halogen, a $C_{1-4}$ alkoxy group and a $C_{1-4}$ alkyl group, (xii) halogen, (xiii) nitro, and (xiv) cyano, or (5) a $C_{1-10}$ alkyl group which is substituted by a $C_{6-10}$ arylsulfonylamino group which may be substituted by 1 to 5 substituents selected from the group consisting of halogen, $C_{1-4}$ alkoxy group and $C_{1-4}$ alkyl group.

16. The compound according to claim 14, wherein R' represents a thienyl group, an azolyl group, a fused thienyl group, a fused azolyl group or a fused furanyl group, each of which may be substituted.

17. The compound according to claim 14, wherein R' represents thienyl, oxazolyl, isoxazolyl, benzothienyl, benzofuranyl, benzoxazolyl or benzothiazolyl, each of which may have 1 to 3 substituents selected from the group consisting of $C_{1-3}$ alkyl which may be substituted by halogen, $C_{6-10}$ aryl, $C_{1-3}$ alkoxy which may be substituted by halogen, halogen and nitro.

18. The compound according to claim 14, wherein R' represents a hydrocarbon group substituted by thienyl, furyl, azolyl, fused thienyl, fused furanyl or fused azolyl, each of which may be substituted.

19. The compound according to claim 14, wherein R' represents a $C_{1-10}$ alkyl group or a $C_{2-10}$ alkenyl group, each of said groups being substituted by an aromatic heterocyclic group selected from thienyl, furyl, oxazolyl, isoxazolyl, benzothienyl, benzofuranyl, benzoxazolyl, benzisoxazolyl, benzothiazolyl and benzimidazolyl, each of which may have 1 to 3 substituents selected from the group consisting of $C_{1-3}$ alkyl which may be substituted by halogen, $C_{6-10}$ aryl, $C_{1-3}$ alkoxy which may be substituted by halogen, halogen and nitro.

20. The compound according to claim 14, wherein R' represents a hydrocarbon group substituted by phenoxy which is substituted by 1 to 3 substituents selected from the group consisting of a $C_{1-3}$ alkoxy group which may be substituted by halogen, nitro, halogen, cyano, amino and a $C_{1-3}$ alkyl group which may be substituted by halogen.

21. The compound according to claim 14, wherein R' represents a hydrocarbon group substituted by a thiol group which is substituted by thienyl, furyl, azolyl, fused thienyl, fused furyl or fused azolyl, each of which may be substituted.

22. The compound according to claim 14, wherein R' represents a $C_{1-10}$ alkyl group or a $C_{2-10}$ alkenyl group, each of said groups being substituted by a thiol group substituted by an aromatic heterocyclic group selected from thienyl, furyl, oxazolyl, isoxazolyl, benzothienyol, benzofuranyl, benzoxazolyl, benzisoxazolyl, benzothiazlyl and benzimidazolyl, each of which may have 1 to 3 substituents selected from $C_{1-3}$ alkyl which may be substituted by halogen, $C_{6-10}$ aryl, $C_{1-3}$ alkoxy which may be substituted by halogen, halogen and nitro.

23. The compound according to claim 14, wherein R' is (1) a heterocyclic group selected from the group consisting of thienyl, oxazolyl, isoxazolyl, benzothienyl, benzoxazolyl, benzothiazolyl and benzofuranyl, each of said groups being unsubstituted or substituted by 1 to 3 substituents selected from the group consisting of (a) a $C_{1-3}$ alkyl group which may be substituted by halogen, (b) a $C_{6-10}$ aryl group, (c) a $C_{1-3}$ alkoxy group which may be substituted by halogen, (d) halogen, (e) nitro, (f) cyano, (g) a ($C_{1-6}$ alkyl)carbonyl, and (h) a ($C_{1-6}$ alkyl)sulfonyl, (2) a hydrocarbon group selected from the group consisting of a $C_{1-10}$ alkyl group and a $C_{2-10}$ alkenyl group, each of said groups being substituted by an aromatic heterocyclic group selected from the group consisting of thienyl, furyl, oxazolyl, isoxazolyl, benzofuranyl, benzothienyl, benzoxazolyl, benzisoxazolyl, benzothiazolyl and benzimidazolyl, each of said aromatic heterocyclic groups being unsubstituted or substituted by 1 to 3 substituents selected from the group consisting of (a) a $C_{1-3}$ alkyl group which may be substituted by halogen, (b) a $C_{6-10}$ aryl group, (c) a $C_{1-3}$ alkoxy group which may be substituted by halogen, (d) halogen, and (e) nitro, and each of said $C_{1-10}$ alkyl and $C_{2-10}$ alkenyl groups being unsubstituted or substituted further by cyano, (3) a hydrocarbon group selected from the group consisting of a $C_{1-10}$ alkyl group and a $C_{2-10}$ alkenyl group, each of said groups being substituted by a phenoxy group which is substituted by 1 to 3 substituents selected from the group consisting of (a) a $C_{1-3}$ alkoxy group which may be substituted by halogen, (b) nitro, (c) halogen, (d) cyano, (e) amino, and (f) a $C_{1-3}$ alkyl group which may be substituted by halogen, (4) a hydrocarbon group selected from the group consisting of a $C_{1-10}$ alkyl group and a $C_{2-10}$ alkenyl group, each of said groups being substituted by a thiol group which is substituted by an aromatic heterocyclic group selected from the group consisting of thienyl, furyl, oxazolyl, isoxazolyl, benzothienyl, benzofuranyl, benzoxazolyl, benzisoxazolyl, benzothiazolyl and benzimidazolyl, each of said aromatic heterocyclic groups being unsubstituted or substituted by 1 to 3 substituents selected from the group consisting of (a) a $C_{1-3}$ alkyl group which may be substituted by halogen, (b) a $C_{6-10}$ aryl group, (c) a $C_{1-3}$ alkoxy group which may be substituted by halogen, (d) halogen, and (e) nitro, or (5) a $C_{1-10}$ alkyl group which is substituted by a $C_{6-10}$ arylsulfonylamino group which may be substituted by 1 to 3 substituents selected from the group consisting of halogen, $C_{1-4}$ alkoxy group which may be substituted by halogen, a $C_{1-4}$ alkyl group which may be substituted by halogen, and nitro.

24. The compound according to claim 14, wherein R' is (1) a heterocyclic group selected from the group consisting of thienyl, isoxazolyl, benzothienyl, benzoxazolyl, benzothiazolyl and benzofuranyl, each of said groups being unsubstituted or substituted by 1 to 3 substituents selected from the group consisting of (a) a $C_{1-3}$ alkyl group which may be substituted by halogen, (b) a $C_{6-10}$ aryl group, (c) a $C_{1-3}$ alkoxy group, (d) halogen, (e) nitro, (f) cyano, (g) a ($C_{1-6}$ alkyl)carbonyl, and (h) a ($C_{1-6}$ alkyl)sulfonyl, (2) a hydrocarbon group selected from the group consisting of a $C_{1-10}$ alkyl group and a $C_{2-10}$ alkenyl group, each of said groups being substituted by an aromatic heterocyclic group selected from the group consisting of thienyl, benzoxazolyl, benzisoxazolyl and benzimidazolyl, each of said aromatic heterocyclic groups being unsubstituted or substituted by 1 to 3 $C_{1-3}$ alkoxy groups, and each of said $C_{1-10}$ alkyl and $C_{2-10}$ alkenyl groups being unsubstituted or substituted further by cyano, (3) a $C_{1-10}$ alkyl group substituted by a phenoxy group which is substituted by 1 to 3 substituents selected from the group consisting of (a) a $C_{1-3}$ alkoxy group, (b) nitro, (c) halogen, (d) cyano, (e) amino, and (f) a $C_{1-3}$ alkyl group, (4) a $C_{1-10}$ alkyl group substituted by a thiol group which is substituted by an aromatic heterocyclic group selected from the group consisting of benzoxazolyl and benzothiazolyl, each of said aromatic heterocyclic groups being unsubstituted or substituted by halogen, or (5) a $C_{1-10}$ alkyl group which is substituted by a $C_{6-10}$ arylsulfonylamino group which may be substituted by 1 to 3 $C_{1-4}$ alkyl groups.

25. The compound according to claim 14, wherein R' is (1) a heterocyclic group selected from the group consisting of thienyl, oxazolyl, isoxazolyl, benzothienyl, benzoxazolyl, benzothiazolyl and benzofuranyl, each of said groups being unsubstituted or substituted by 1 to 3 substituents selected from the group consisting of (a) a $C_{1-3}$ alkyl group which may be substituted by halogen, (b) a $C_{6-10}$ aryl group, (c) a $C_{1-3}$ alkoxy group which may be substituted by halogen, (d) halogen, and (e) nitro, (2) a hydrocarbon group selected from the group consisting of a $C_{1-10}$ alkyl group and a $C_{2-10}$ alkenyl group, each of said groups being substituted by an aromatic heterocyclic group selected from the group consisting of thienyl, furyl, oxazolyl, isoxazolyl, benzofuranyl, benzothienyl, benzoxazolyl, benzisoxazolyl, benzothiazolyl and benzimidazolyl, each of said aromatic heterocyclic groups being unsubstituted or substituted by 1 to 3 substituents selected from the group consisting of (a) a $C_{1-3}$ alkyl group which may be substituted by halogen, (b) a $C_{6-10}$ aryl group, (c) a $C_{1-3}$ alkoxy group which may be substituted by halogen, (d) halogen, and (e) nitro, (3) a hydrocarbon group selected from the group consisting of a $C_{1-10}$ alkyl group and a $C_{2-10}$ alkenyl group, each of said groups being substituted by a phenoxy group which is substituted by 1 to 3 substituents selected from the group consisting of (a) a $C_{1-3}$ alkoxy group which may be substituted by halogen, (b) nitro, and (c) halogen, (4) a hydrocarbon group selected from the group consisting of a $C_{1-10}$ alkyl group and a $C_{2-10}$ alkenyl group, each of said groups being substituted by a thiol group which is substituted by an aromatic heterocyclic group selected from the group consisting of thienyl, furyl, oxazolyl, isoxazolyl, benzothienyl, benzofuranyl, benzoxazolyl, benzisoxazolyl, benzothiazolyl and benzimidazolyl, each of said aromatic heterocyclic groups being unsubstituted or substituted by (a) a $C_{1-3}$ alkyl, (b) a $C_{6-10}$ aryl group, (c) a $C_{1-3}$ alkoxy group, (d) halogen, and (e) nitro, or (5) a $C_{1-10}$ alkyl group which is substituted by a $C_{6-10}$ arylsulfonylamino group which may be substituted by 1 to 3 substituents selected from halogen atom, a $C_{1-4}$ alkoxy group which may be substituted by halogen, a $C_{1-4}$ alkyl group which may be substituted by halogen, and nitro group.

26. The compound according to claim 14, which is N-(diaminophosphinyl)-3-thiophenecarboxamide.

27. The compound according to claim 14, which is N-(diaminophosphinyl)-5-methyl-2-thiophenecarboxamide.

28. The compound according to claim 14, which is N-(diaminophosphinyl)-3-methyl-2-thiophenecarboxamide.

29. A compound represented by the formula (IA'):

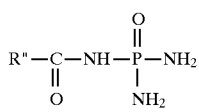

wherein R" represents a furyl group or a pyridyl group, each of which has 1 to 3 substituents selected from the group consisting of halogen, cyano, formyl, $C_{1-3}$ alkyl which may be substituted by halogen, $C_{1-3}$ alkoxy which may be substituted by halogen, ($C_{1-3}$ alkoxy)carbonyl which may be substituted by halogen and $C_{1-3}$ alkylsulfonyl which may be substituted by halogen, or a salt thereof.

30. The compound according to claim 29, wherein R" represents a furyl group which is substituted by 1 to 3 substituents selected from halogen and a $C_{1-3}$ alkyl group which may be substituted by halogen.

31. The compound according to claim 29, wherein R" represents a furyl group substituted by halogen.

32. The compound according to claim 29, which is N-(diaminophosphinyl)-5-bromo-3-furancarboxamide.

33. The compound according to claim 29, which is N-(diaminophosphinyl)-2-methyl-3-furancarboxamide.

34. A pharmaceutical composition which comprises the compound as claimed in claim 14 and a pharmaceutically acceptable carrier.

35. A pharmaceutical composition which comprises the compound as claimed in claim 14, an antacid or an acid secretion inhibitor, and a pharmaceutically acceptable carrier.

36. A pharmaceutical composition which comprises the compound as claimed in claim 29 and a pharmaceutically acceptable carrier.

37. A pharmaceutical composition which comprises the compound as claimed in claim 29, an antacid or an acid secretion inhibitor, and a pharmaceutically acceptable carrier.

38. A process for producing a compound of the formula:

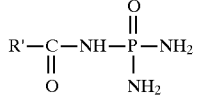

wherein R' represents (a) a heterocyclic group which may be substituted (except excluding a furyl group which may be substituted, a pyridyl group which may be substituted and a 3-amino-2-oxo-1-azetidinyl group which may be substituted), (b) a hydrocarbon group substituted by a heterocyclic group which may be substituted (except excluding a hydrocarbon group substituted by a maleimido group which may be substituted), (c) a hydrocarbon group substituted by a substituted phenoxy group, (d) a hydrocarbon group substituted by a heterocyclic-thio group which may be substituted, or (e) an alkyl group substituted by an arylsulfonylamino group which may be substituted, or a salt thereof, which comprises reacting a compound of the formula:

wherein R' is as defined above, or a salt thereof, with ammonia.

39. The process according to claim 38, wherein the compound of the formula (IIIA) is obtained by (a) reacting a compound of the formula:

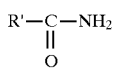

wherein R' is as defined in claim 38, or a salt thereof, with phosphorus pentachloride and then reacting the resulting compound or a salt thereof with formic acid, or (b) reacting a compound of the formula:

wherein R' is as defined in claim 38, or a salt thereof, with phosphorus oxychloride

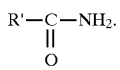

40. A process for producing a compound of the formula:

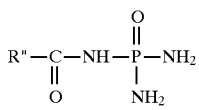

wherein R" represents a furyl group or a pyridyl group, each of which has 1 to 3 substituents selected from the group consisting of halogen, cyano, formyl, $C_{1-3}$ alkyl which may be substituted by halogen, $C_{1-3}$ alkoxy which may be substituted by halogen, ($C_{1-3}$ alkoxy)carbonyl which may be substituted by halogen and $C_{1-3}$ alkylsulfonyl which may be substituted by halogen, or a salt thereof, which comprises reacting a compound of the formula:

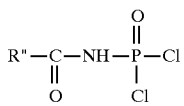

wherein R" is as defined above, or a salt thereof, with ammonia.

41. The process according to claim 40, wherein the compound of the formula (IIIA') is obtained by (a) reacting a compound of the formula:

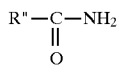

wherein R" is as defined in claim 40, or a salt thereof, with phosphorus pentachloride and then reacting the resulting compound or a salt thereof with formic acid, or (b) reacting a compound of the formula:

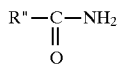

wherein R" is as defined in claim 40, or a salt thereof, with phosphorus oxychloride.

42. An anti-*Helicobacter pylori* agent which comprises a compound represented by the formula:

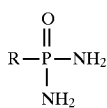

wherein R represents an amino group which may be substituted, or a pharmaceutically acceptable salt thereof, and an antacid or an acid secretion inhibitor.

43. The compound according to claim 14, wherein R' is a thienyl group which may be substituted by 1 to 3 substituents selected from a $C_{1-3}$ alkyl group which may be substituted by halogen, a $C_{1-3}$ alkoxy group, a halogen atom, a nitro group, a cyano group, a ($C_{1-6}$ alkyl)carbonyl group and a ($C_{1-6}$ alkyl)sulfonyl group.

44. The compound according to claim 14, wherein R' is a thienyl group which may be substituted by a $C_{1-3}$ alkyl group.

\* \* \* \* \*

UNITED STATES PATENT AND TRADEMARK OFFICE
CERTIFICATE OF CORRECTION

PATENT NO.   : 5,840,917
DATED        : November 24, 1998
INVENTOR(S)  : Satoru OI et al.

It is certified that error appears in the above-indentified patent and that said Letters Patent is hereby corrected as shown below:

In claim 11, on line 1, the word "use" should read -- method --.

Signed and Sealed this

Thirtieth Day of March, 1999

Attest:

Attesting Officer

Q. TODD DICKINSON

Acting Commissioner of Patents and Trademarks